US008962265B2

(12) United States Patent
Sullivan, Jr. et al.

(10) Patent No.: US 8,962,265 B2
(45) Date of Patent: Feb. 24, 2015

(54) MUTANT PARASITES FOR USE AS VACCINES AND PLATFORMS FOR SCREENING FOR COMPOUNDS

(75) Inventors: William J. Sullivan, Jr., Carmel, IN (US); Ronald C. Wek, Indianapolis, IN (US)

(73) Assignee: Indiana University Research and Technology Corp., Indianapolis, IN (US)

( * ) Notice: Subject to any disclaimer, the term of this patent is extended or adjusted under 35 U.S.C. 154(b) by 0 days.

(21) Appl. No.: 13/702,030

(22) PCT Filed: Jun. 6, 2011

(86) PCT No.: PCT/US2011/039345
§ 371 (c)(1),
(2), (4) Date: Feb. 15, 2013

(87) PCT Pub. No.: WO2011/153552
PCT Pub. Date: Dec. 8, 2011

(65) Prior Publication Data

US 2013/0142829 A1 Jun. 6, 2013

Related U.S. Application Data

(60) Provisional application No. 61/351,389, filed on Jun. 4, 2010.

(51) Int. Cl.

| | |
|---|---|
| ***G01N 33/573*** | (2006.01) |
| ***C12Q 1/48*** | (2006.01) |
| ***C12Q 1/00*** | (2006.01) |
| ***A61K 39/015*** | (2006.01) |
| ***A61K 39/00*** | (2006.01) |
| ***A61K 39/002*** | (2006.01) |
| ***A61K 39/012*** | (2006.01) |
| ***G01N 33/569*** | (2006.01) |

(52) U.S. Cl.
CPC .............. *G01N 33/573* (2013.01); *C12Q 1/485* (2013.01); *G01N 33/56905* (2013.01); *A61K 39/00* (2013.01); *G01N 2333/445* (2013.01); *G01N 2333/45* (2013.01); *G01N 2500/04* (2013.01)
USPC .......... 435/7.4; 435/4; 424/272.1; 424/265.1; 424/273.1

(58) Field of Classification Search
CPC .......... G01N 2500/00; G01N 2500/04; G01N 33/573; G01N 2333/445; G01N 2333/45; G01N 33/56905; C07K 14/45; C12Q 2600/136; C12Q 1/485; C12Q 1/00; C12N 9/00; C12N 9/12
See application file for complete search history.

(56) References Cited

PUBLICATIONS

Narasimhan et al., The Journal of Biological Chemistry, 2008; 283(24): 16591-16601.*
Moerke et al., Cell, 2007; 128: 257-267.*
Sullivan, W.J. Jr. et al., "Parasite-specific eIF2 (eukaryotic initiation factor-2) kinase required for stress-induced translation control," Biochem. J., Mar. 1, 2004, pp. 523-531, vol. 380.
Joyce, B.R. et al., "Phosphorylation of eukaryotic initiation factor-2α promotes the extracellular survival of obligate intracellular parasite *Toxoplasma gondii*," Proceedings of the National Academy of Sciences, Oct. 5, 2010, pp. 17200-17205, vol. 107, No. 40.
Konrad, C. et al., "A GCN2-Like Eukaryotic Initiation Factor 2 Kinase Increases the Viability of Extracellular *Toxoplasma gondii* Parasites," Eukaryotic Cell, Sep. 9, 2011 pp. 1403-1412, vol. 10, No. 11.

* cited by examiner

*Primary Examiner* — Gary Nickol
*Assistant Examiner* — Lakia Tongue
(74) *Attorney, Agent, or Firm* — Faegre Baker Daniels LLP

(57) ABSTRACT

Cloning and characterization of a TgIF2α kinase from *Toxoplasma gondii* designated TgIF2K-D illustrates that this protein is related to GCN2, an eIF2α kinase known to respond to nutrient starvation in other organisms. TgIF2K-D is present in the cytosol of both intra- and extracellular *Toxoplasma* and facilitates translational control through TgIF2α phosphorylation in extracellular parasites. Both a TgIF2K-D knockout parasite and a parasite harboring the TgIF2α mutant (S71A substitution) exhibited loss of eIF2α kinase activity which manifested itself as significant fitness defect. Accordingly, eIF2α phosphorylation and translational control are an important mechanism by which vulnerable extracellular parasites protect themselves which searching for a new host cell. TgIF2K-D is an excellent target for development of compounds and therapies that can be used to treat infections caused by *Toxoplasma* and other eukaryotic parasites, especially parasites that have high homology or identity to TgIF2K-D.

2 Claims, 37 Drawing Sheets

SEQ ID NO: 13, cDNA sequence for TgIF2K-D

[illegible]

FIG. 12A

SEQ ID NO: 13, cDNA sequence for TgIF2K-D

GCTGGCGTCGCGGATCAGGGCGCGCTGCACCCGAAGGCGAGACTCCAGAGGTTTTTAATCTGCGAGCCTGCCCGTG
GCTGCTCAGACTCAGTGTGTCTGGGTGCGGCTTCTGCCCTTTCTGGGGAAGAGAGCGAGGAAGAAGAGACAGAGGAG
AACGACCGGAAAGCCGAGAAGGAGTCCCGAAACTGCGGTCGCCTTCACGCTCGTCTCCAGAGCTCTCGCAGTCGCC
TCGCCCAGGGCCTCAATGCTGCTGCTGCGCCGTCCCCCTCCACGGAGCCCCCTGCGTCTGCCGTCTTGGACAAAGAA
CAAACGCATGCTTCTTGGACAGATCGGATTCCGACTCGGGAGCCTTTCTTGCACTCGTGCCTCCACCACAGCTGACA
TCTTCGCGCTCGACGGCCAAGGATCGTCTGGGCGTCTGTCTCCTTCCTCGACTCTCACGCCCTCCGGCCCCGTTTCC
GCGCCGAGCAGGTCTCCTGTCTCCTCGCCCCGCCGATGGACCGCGACGCAGGAGACGCGAGACGCCGGGCAACAG
CAGAGGCCGCCCTCTCTCAGCGGTGTCAGCTGTGCTCGGGGAGTGCGACGTGAGTGTGTACGCTATTTATTTCGA
GTCTGAGGAAACTCAGCGGTCGTTCTTCGCAGTCGTCGATGTGCTCCTGCCCAGAAATTACCCCGCAGGCCGCCGT
ACGTTGCAGTGGGTCTCTCTCACGCCGTCCCCGGAACGGAAGTCCAGAGGCTCTGCGGACTTGAGAGAAGAGTTCGA
GGCCTCCAAAGGCGAGGTTGTCTTGTACCGAGTCTGTCTCCAACTCCAGTCGTTCATGGCGGAGCTGTCGAGCACCT
CTTGCTTCAGCAATTTCTGGAGAAATGCATTCAAGGAGCGTCAGAGACGGCACTTGCTGCTGCGGAGCAGCATAT
GATTCACGGAGTCTGAAGGCTCGGCAAGGCCTTCTGTCGCATCCGTTCGGGCATTTGGCCGGCCGCCTCAAGACGA
GCGCGAGCCGCTCCCCTCGGTCTTCAGAGACGCGCCCACAGCTACCGCCCATCGCTGCAGTACTCCCCGGAGTGTCGC
CTGGGCCGCCGACGACGAGGCTTCGTTTTACTGGGAGGACGAGGCGGACGAAGAGTTTCTGACTTCCTTGATCTCGAA
GAGGACTATGTCGATATTCAGTCGAGCTTCTACGCCTCGCCCTCGAACTCGCGGAGACGGCGCTCGCACCGCGCTG
GATCTCTCAATTTCGGGCTGCGGCTCGCTGTCACGTCGCAGCCGTCTCGGATCTCGGCGCGCTTCGGCCTCGAGCTG
GAGCCCCAGAAAAAAATCAGAGGCGCCGCCGAGTCCCGCGGCGCCGACTCGGAGGTCCCAGCGGCCTCCAGGCGCTCTCG
GCGTCGTCGCAGGGGCGCGCGCTGCCCCAGTGAGGCTGTGCCAGACGAAAAGGGAGGCGGAGACAGCGAACCGGGG
GTGCTCGAGAAAGAAAGTGCGCAAGCGCTGTCGGGGCGGCGGGCGTTCCTCGTCCCCGCTCGCCGGCAAAACGCCGG
AGGCGAAGAAACAGAGCGACAGCGGTGCTGGAGCGGAAGCGGGTTCGGGGCGCTGGCTGCACGGGTGCCCGTGAC
GGCGCCGCGCTGGCGACGGGGAACAACGGCGCCCCGGAGCGGGCGTCTCCGAGAGCCTCTGCGTCGCGGGGCGCGGG
GCCGAGAGGAAAGGCGCCGCGGCGCAGGGAGTTTCCGATCGCTTCTCCTCAGCTCACAAGGACGACGAGTACAAAG
AGATTTCATTCAACTCGAGGTACTGGGCAGCGGCGAGCGGTACCGCATTGCTCTCGTTTACCACATCATCGACAAGC
ACAAGTACATCGTGAAGCAAATCTTCATTCCTGCGGTCCAGTGTCCTGTTGGCCGTCTCTCGCCAGGCACAGAAGC
TGGACGGAGACGCAAGCAACTTCAGGGCCTCGAACTCGTTGAAAGCGCTCTTCGTCAAGTGACGCTCCTCTCGCTC
TTAACATCCCTACATCATCGGTACCACCAAGCGTGGACGCAGTACCACACGGCGCTGCGCTCGCCGGCACCAGCGG
CGAAGGCGGGGACCCCCCCAACGCGATGCCTCTGTCGGATCTAGGCGACGCCCAGAGAGCGGCCAGGACCTTGCATT
GGAGTGTACGTACAGATGGAGTTCTGCGAGCGCAGTCTCGAAGACGAAATCGAGAAACGCACAGTGCTGCACTGGGA
CTCTCAGCAAATCTGGACGCTGTTCGACAGACGCTGGAAGCCTCGTGTACATACACGCAACCGGCTGTGTCACCTG
TCTCTGAAGCCGTCGAACGTATTTCTTGAGCCTGACGCTTACGGCTACAATGTCAAGCTGGGCGACTTCGGCTCACT
TCACTTTTTTCGATGTTCACAACGTGCACTCGCCCATTTCGCGACTCTACAGGGCGCGGAACTCCTCGGCGCAGCG
GACAGGAAATTCGCTTCTCTGACGATGCGGCGACGCAGACAAGGCGACAGGTACTCTCGGCGTCTCTTTGCGGAGA
TGTGGGTCGACACGAAATGTTCGGACGCTCCTGCAGTCGGATCGAGTTTTTAACTTCTCTCGTGAAAGAACGGAAT
CTGCAGCAGCTGAACGTCCTTCAGCGGCGGTCAAAATATCAAGCACCTGCTGTCTCCGAACCCTGGAGATCCTCCTT
CGTCAATGACTTTGCTGCAGTCTTCGCGGCTTCCACCAGCTGTCGAGGAGGATCTGTTCAAAGCCTTCTTCTTCGGC
TGCGTACGCAGTCCAGAGCGGCTCTGGGACACCGCCTCTTCGGGACTCTTCGCTCTCGCCTGCGAGCAGAAGAAAA
CAGATCCGCGGAAAAAAAATCTGGACAAAGGCCGAAGTCTCTCGCTTCCACCGCTCAGACGAAGGCCTGCAATCCCA
CACTCCACACGGAGGCGCCGGGCCTGGCAGGCGAAGTCCTCAAAATCTTTTTTCGTCGACAATTCGATTCTGCATCTG
CGACTCTCTCTTTAGTGATTTCCTTAGAAGATCAGCACGGCGCCCGAGCCTGAAATGCGGTGTCTCGTACAACGGTC
CCTTGCCGACTTCTTTGCTCGATGCGGCGCAGACGAAATTCAAATCCCTCTCGTTGTTCCCTGACGAAAGGCCTGGC
GAAATGGAAGAGGCCTTGAAACACTCACCGACGTATGCGTCGATTCCTCTCCGAGTCTCTGTCTCTCGCGGACCA
CAGAAATGTACTTCTGACTCTCCGCGGTTTCACGTCTGCGCTCTGTGCCTGCGGAGGCGGCGCGCTTGCCACAC
TCTCTCCACTCTGCGTCGCTCGCGCCATCTCGGGAGGCGGCTCTCCAGGCGCTGCTGTCTCCTGTCTCCTCGCGCCT
GTGACCTGTCCCTTCTGTGGGGAACTGTCCCTTCGGCTTCGTGTCTCCTCGCTCGTCGCTCTCGTCCGCCTCCTGC
TTTGCCCATGCTGCGCTCCTCTCGGCGCTGTGGGCAGAGCTTACGCTGGGTCCTCGAAGACTCAGACAGAGGAAAA
GAAAAACAGAAGACTCTGGAAATTTCGAGTGCAGGATGCGAATACCGACGCTTCTGCGTGGCGCATTGTTACACAGCT
CCAACGGTCTCGTTCCTCGGCGAGTAGGTCACCTCTTCCATACTTTTCGGCTGCTACCAGCTTCTCTTCCCTGCTG
GCCGCGAGCCGCCTTGTCCCTCCTCAACATCCCCGCTCTGTCGCAAATCCAGTAAGCCTCGCGCTGCGACGGGCAT
CTCCTCCTTCTCTTCGCCCACTCTTCTCTCCTTTCTCGCCGTCGTCACATCTGCGCTCTCGGCGGAGGAGCAGCGGA
CAGCTCTTTTAGAGGCTGAAGTTCTGTCGGTCTGCGGAGGCGGCGTGAGGACTGTGCAAGCGAGTCTCGGCCTCGCCT
TGGCTGGCGAGTCTCTTGGTCTCTCGGCAGCCTCTTGCCTGCAATTCTCAGAGAATCTTTCTTGGTCCGCTCTCAG
AGCTGCCGCCATGCAATGCGCTGCTCGGGCAAGTCGCACCGTCGGAGACGGCCAAGTGGCAAGAGACGCCCTTCAGAA
GGCTCTGGAGAGACTCGTCGATGTTCACTCTCGGCTCCACGGACGCATGCAGAGGACGCGGCCCCTCCAGACTGTG
TCTGCTTCTCGCCCACGGACCCTCGGGCCTGGTGTCTTCTGCTGCAGCTGCTGTCGTCTTCGTCGCTCGCTCTCGG
CGGCGCATGCCAGCCCGGAGGTGACGCGGGCAGAGACGCCGAAAGGCGGTAGAGACAGGTCACTCGCAGCGAAGAA
GCGCAAGACAAGGGAGGCAGCCGCTGCCGAGCAGTCGCTGGCCGACGCCTTCCTCGCAGAGCGAGGTCGGGAGACATCT

FIG. 12B

SEQ ID NO: 13, cDNA sequence for TgIF2K-D

[illegible] (SEQ ID NO: 13)

FIG. 12C (SEQ ID NO:26) TgIF2K-D -------ADIFPLDAQGSSGRLSPSSTLTPSGPVSAPSRSPVSSPSPDGT----
- ATQETRDAGATAEAALSQRCQLCSG 912

(SEQ ID NO:27) NcIF2K-D --------------------------------ASSSASRSPVSSPAPDGPPA
SCLAAQETR-- GERDPEIPRPRCQLCLG 970

(SEQ ID NO:28) Pf14_0264 MDNDNNKRKKTKKKKVRNVNNKNSNENKKKGIQENQDEQNY
TEQYADQIEEEILALHNIF EPMYVDNPGHVKKSDLPKDLM 80

(SEQ ID NO:29) MmGCN2 ----------------------MAGGRGASGRGRAEPQESYSQRQDHEE
QALEAIYGSDFQDLRPDARGRVRE------- 51

(SEQ ID NO:30) DmGCN2 ---------------------MAD----------EKAKESFRERQAQELEVIKS
IFGCQDVEDLRPQANPSLWK------- 42

(SEQ ID NO:31) ScGCN2 ------------------------------MSLSHLTLDQVYEIQCN
ELEAIRSIYMDDFT DETKRKSSWDKQ------- 43

TgIF2K-D -------------ECDVECVR----------YLFR-VLSETQRAFFAVVDVLLPRNYPAGPPYVAVGL
SHAVPRTEVQRELR 970
NcIF2K-D -------------DCDVECVR----------YLFR-VLSETQQAFFAIVDVLLPRNYPAAPPYVAVGLSAAVP
REELEQERN 1028
Pf14_0264 KRNEYIKNSKDLSENHIVDINDEINKNTCLTFSMFENIDNIMEKYKVTFMYEKIYPYSYPNVVIHMN
TKLNEEQKNDVTL 160
MmGCN2 -------------PPEDNLVL----------YPQG--LAGEKVYVQVELQVKCPPTYPDVVPELSLK
NAKGLSNESVNLLKS 108
DmGCN2 -------------PTDIRIQL----------TPLRDSSNGLETYVCTKEHVTCPSKYPKLPPKISLE
ESKGKSDQLLEAARN 101
ScGCN2 -------------PQEIFEI----------TERS--VDKEPVESSITIHFAMTPMYPYTAPEIEFR
NVQNVMDSQLQMLKS 99

TgIF2K-D DLREEFEASKGEVVLYRLCLQLQSFMAELSSTSCFSNLWEEMHFKERQRRHLLLREQ---HMIHQSLKA
RQGLLSHPF-- 1045
NcIF2K-D SLREEYEASRGEVVLYRLCLQLQSFMAELSSTLCFSNLWEEMHFKERQRRHFLLREQ---HMIHRNMKA
RQGLLSHPFGP 1105
Pf14_0264 NIRKICAKNYCRITLEEKCLFINEYENKIFNN-DEQNLWEEMNYRIDDTSFKKDRDNEIYNDL
HNEIEDGKKLDNYKNVQ 239
MmGCN2 HLKELAKKQCGEVMIFELAHHVQSFLSEHNKPPPKS-FHEEMLERQAQEKQQRLLEA---RRKEEQE-QRE-
ILHEIQRR 182
DmGCN2 QLQAQSQELRGEVCIYELAQTVQAFLLEHNKPPKGS-FYDQMLQ-DRQKRDQELQQI---QRQRESL-
QRQTLIDEVERR 175
ScGCN2 EFKKIHNTSRGQEIIFEITSFTQEKLDEFQNVVNTQSLEDDRLQRIKETKEQLEKEE---REKQQETIKKR---
SDEQRR 173

FIG. 15

```
(SEQ ID NO:32)     TgIF2K-D     --LDYSLPQVVVVTAQSAKQLPLGFSLVCRLLRRGIRAELRVTPV
VETSYFQRLLRR--SRRILYHVQIQHHRASVAAHATLT- 2513
(SEQ ID NO:33)     NcIF2K-D     --DEAALPQVVVVTAQSAKHLPLGFSLVCKLLRRCVRAELRVSP
VVETSYFQRLLRR--SRRILYHVQIQHHRASVSSHAAI-- 2739
(SEQ ID NO:34)     Cmu_027700   --LQSCYPKVVVVVTQKNKLQLLVLSLARQLWLNGIRCEYRLAPVQ
YLSIFVDKLKKGTLVELLVVVMKTNKPTTNSLYNASNI 1300
(SEQ ID NO:35)     PF14_0264    LLIDFHSPSVVITAKAYKLLMYAFSLYNSLIQNGIKCECRITPLM
ETSKFEKSLLK--YKNINIHVQINQKISSSTSINIEDY 2300
(SEQ ID NO:36)     Pb_101620    -
FIDFHSPSVVITTKAYKLLVYAFSLYNSLIQNNIKCECNISPLIFTLKFEQNLLK-YNHINMHVQINHKVNSN
PTV-CSDY 1892
(SEQ ID NO:37)     PkH_113740
MHIDFHSPSVVITTKAYKLLVYAFSLYNNLIQNGIKCECKISPLVETSKFEQGLLK-YSDINIHVQIIQKVNSNT
FLNIEDY 2053
(SEQ ID NO:38)     Pvx_085120   --
IDFHSPSVVITTKAYKLLVYAFSLYNSLIQNGIKCECKISPLVETSKFEQGLLK-YGDINIHVQITQKVNSNTSL
NIEDY 2219
```

MUTANT PARASITES FOR USE AS VACCINES AND PLATFORMS FOR SCREENING FOR COMPOUNDS

CROSS-REFERENCES TO RELATED APPLICATIONS

This application is a National Stage filing of International Application Serial No. PCT/US2011/039345, filed Jun. 6, 2011, which claims the benefit of U.S. Provisional No. 61/351,389 filed Jun. 4, 2010, the disclosures of which are expressly incorporated herein by reference.

STATEMENT OF GOVERNMENTAL RIGHTS

This invention was made with government support under A1084031 and GM049164 awarded by the National Institutes of Health. The government has certain rights in the invention.

FIELD OF THE INVENTION

Aspects of the invention relate to selecting for and using novel strains of *Toxoplasma* parasites that include nonphosphorylatable TgIF2α and TgIF2α and homologous proteins to identify compounds that can be used to treat and/or control infections caused by organisms such as *Toxoplasma gondii*.

BACKGROUND

Parasites that have adapted to live and replicate within another cell benefit from abundant resources, protection from host immunity, and shelter from therapeutic agents. As the demands of the parasites exceed what the host cell can supply, the parasites must find a new host cell, a journey that can leave them vulnerable to nutrient deprivation and environmental stresses. Protozoa in the phylum Apicomplexa are parasites that require a eukaryotic host cell in order to replicate. *Toxoplasma gondii* is one such obligate intracellular parasite, capable of using virtually all warm-blooded vertebrates as host organisms (Hill et al., 2005). Acute *Toxoplasma* infection can cause spontaneous abortion or congenital birth defects, as well as severe disease in immunocompromised patients. This disease is widespread in the developing world and poses a significant risk to both humans and animals.

Currently, there is no effective vaccine for treating humans and only some partially effective vaccines available to treat animals. Current treatments consist of anti-folates that are problematic due to toxicity issues; therefore there is an urgent need to develop novel therapies to treat this parasitic infection. There is a dearth of effective treatments for infected humans and animals. Accordingly, there is a pressing need for compounds to vaccinate vulnerable populations and to treat infected individuals. Some aspects of the instant invention seek to address these needs.

SUMMARY

Some embodiments of the invention include methods of identifying a compound, comprising the steps of: providing at least one translation initiation factor that is phosphorylated by a kinase and identified in a singled celled eukaryotic parasite. In some methods the factor and its kinase are found in a single celled parasite selected from the genera consisting of *Toxoplasma, Plasmodium*, and *Cryptosporidium*. In some embodiments the translation initiation factor is phosphorylated by an eIF2α kinase selected from the group consisting of: TgIF2K-A, TgIF2K-B, TgIF2K-C, and TgIF2K-D.

In some embodiments the eIF2α kinase that serves as the target for the compound search has greater than or equal to about 90 percent homology to TgIF2K-D identified in the parasite *Toxoplasma gondii*. In some embodiment the target has about 95 percent homology to TgIF2K-D. In some embodiments the target has about 85 percent or greater identity to TgIF2K-D. In some embodiments the target has about 95 percent or greater identity to TgIF2K-D. In still other embodiments, the target has about 85 percent or greater identity to TgIF2K-D as identified in *Toxoplasma gondii*. And in still other embodiments, the target has about 95 percent or greater identity to TgIF2K-D identified in *Toxoplasma gondii*. In yet more embodiments the target kinase is TgIF2K-D identified in *Toxoplasma gondii*.

In some embodiments compounds are screened for their ability to bind to either the translation initiation factor for example a protein with at least 90 percent homology to the translation initiation factor TgIF2α identified in the parasite *Toxoplasma gondii*. In some embodiments the target is a protein having at least 90 percent homology to the translation initiation factor TgIF2α identified in *Toxoplasma gondii*. In some embodiments the target has at least 95 percent homology to TgIF2α identified in *Toxoplasma gondii*. In some embodiments the target has between 80 to 95 percent identity to TgIF2α identified in *Toxoplasma gondii*.

Some aspects of the invention include methods for reducing the infectivity of a singled celled eukaryotic parasite, comprising the steps of: contacting a single celled eukaryotic parasite with at least one compound that interferes with the activity of at least one eIF2α kinase associated with the parasite, or of genetically engineering a parasite to exhibit a reduction or a loss of activity caused by altering or knocking out at least one protein having eIF2α activity.

Still other embodiments include methods for reducing the infectivity of a single celled eukaryotic parasite, comprising the steps of: providing a single celled eukaryotic parasite, wherein the parasite includes at least one eIF2α kinase and at least one translation initiation factor, wherein the at least one kinase phosphorylates the at least one translation factor; and contacting the parasite with at least one compound that interferes with or eliminates the phosphorylation of the translational initiation factor.

In some embodiments a compound acts by interfering or preventing the phosphorylation of at least one translation initiation factor such as TgIF2α identified in *Toxoplasma gondii*. In some embodiments the translation initiation factor that binds to the compounds has between 75 to 95 percent identity to TgIF2α identified in *Toxoplasma gondii*. In some embodiments the phosphroylated translation initiation factor has at least 90 to 95 percent homology to TgIF2α identified in *Toxoplasma gondii*.

In some embodiments translation initiation is reduced by altering the activity of at least one eIF2α kinase associated with the parasite. In some embodiments the compounds act by biding to, and interfering with, at least one kinase selected from the groups consisting of: TgIF2K-A, TgIF2K-B, TgIF2K-C, and TgIF2K-D.

In some embodiments the compounds act by binding to at least one kinase having at least 90 percent homology to TgIF2K-D identified in the parasite *Toxoplasma gondii*.

In some embodiments the eIF2α kinase that binds to the compound has greater than or equal to about 90 percent homology to TgIF2K-D identified in the parasite *Toxoplasma gondii*. In some embodiment the target has about 95 percent homology to TgIF2K-D. In some embodiments the target has about 85 or greater identity to TgIF2K-D. In some embodiments the kinase that binds to the inhibitor has about 95 percent or greater identity to TgIF2K-D. In still other embodiments, the kinase has about 85 percent or greater identity to TgIF2K-D as identified in *Toxoplasma gondii*. And in still other embodiments the kinase has about 95 percent or greater identity to TgIF2K-D identified in *Toxoplasma gondii*. In yet more embodiments the target kinase is the same TgIF2K-D identified in *Toxoplasma gondii*.

In some embodiments of the invention the parasitic infection that is treated by interfering with the translation initiation factor is selected the genera consisting of; *Toxoplasma, Plasmodium* and *Cryptosporidium*. In some embodiments the compound acts by reducing or eliminating the activity of at least one protein that has at least 90 percent homology to TgIF2α identified in *Toxoplasma gondii*.

Some aspects of the invention provide methods for vaccinating a patient, comprising the steps of: providing a mutant of a single celled organism selected from a group of parasites consisting of *Toxoplasma, Plasmodium*, and *Cryptosporidium*, wherein said mutant is deficient in eIF2α kinase activity; and contacting a mammal with said mutant form. In some embodiments the parasite is *Toxoplasma gondii*. In some embodiments the mutant eIF2α kinase has greater than or equal to about 95 percent homology to at least one kinase selected from the group consisting of TgIF2K-A, TgIF2K-B, TgIF2K-C, and TgIF2K-D. In some embodiments the mutant parasite lacks virtually all TgIF2K-D activity.

In some embodiments the parasite used is either alive or killed in the vaccine and includes an eIF2α kinase having greater than or equal to about 75 percent identity to TgIF2K-D; in some embodiments it has about 85 percent identity to TgIF2K-D and in some embodiments it is TgIF2K-D. In some embodiments the organism is a knockout of TgIF2K-D or of a similar protein having at least 90 percent homology or at least 75 percent identity to TgIF2K-D identified in *Toxoplasma gondii*.

In some embodiments that parasite used is either alive or killed in the vaccine and includes a translation factor that cannot be phosphorylated by wild type kinase having greater than or equal to about 85 percent identity to TgIF2α-S71A. In some embodiments it has about 85 percent identity to TgIF2α-S71A, while in other embodiments the translation factor has greater than 90 or 95 percent identify to TgIF2α-S71A. In some embodiments the patient that is either vaccinated against or treated for an infection caused by a single celled eukaryotic parasite is an animal selected from the group of animals consisting of: humans, ovines, felines, and bovines. While seeking a new host cell, obligate intracellular parasites, such as the protozoan *Toxoplasma gondii*, must be able to endure the extracellular environment. The mechanisms *Toxoplasma* utilizes to remain viable while deprived of a host cell are not well understood. Phosphorylation of eukaryotic initiation factor-2 alpha is a well conserved stress response. A *Toxoplasma* harbouring a point mutation (S71A) in eIF2α cannot be phosphorylation, as in the wild-type, was generated. Experiments with the mutant organism demonstrate that TgIF2α phosphorylation is critical for parasite viability as TgIF2α-S71A mutants are ill-equipped to cope with life outside the host cell. For example organisms bearing the TgIF2α-S71A mutation demonstrate a significant delay in the onset of acute toxoplasmosis in vivo. These results indicate that the phosphorylation of TgIF2α plays a crucial role during the lytic cycle of these organisms. Phosphorylation of TgIF2α may help to ameliorating some of the stress imposed on the parasite when it is exposed to the extracellular environment while it searches for a new host cell to invade.

Some aspects of the invention include, mutant eukaryotic single cell parasites, comprising a mutant form of a translation factor, wherein the mutant form of the translation factor includes at least one amino acid substitution, wherein the amino acid substitution results in a form of TgIF2 having a different phosphorylation pattern than a wild type isoform of the translation factor, wherein the translation factor is TgIF2. In some embodiments, the parasite is *Toxoplasma*, for example, *Toxoplasma gondii*. In some embodiments, the parasite is selected from the group consisting of *Plasmodium* and *Cryptosporidium*. In some embodiments, a mutation in the parasite's translation factor reduces the parasite's ability to exist outside of a host cell and decreases the virulence of the parasite in the mouse model of infection. In some embodiments, a mutation is in the translation factor TgIF2, referred to as TgIF2α-S71A. In some of these mutants, the single cell eukaryotic parasite harbouring the mutant form of the translation factor TgIF2 is similar to a parasite harbouring wild type TgIF2 in motility, invasion, replication, or egress but not its ability to survive outside of a host cell.

Still other aspects of the invention include methods for vaccinating a patient, comprising the steps of: providing a mutant form of a single cell eukaryotic parasite according to claim 1; supplying a mammal; and contacting the mammal with said mutant from of a single cell eukaryotic parasite. In some embodiments, the mammal is selected from the group consisting of: ovines, felines, and bovines and some embodiments the mammal is a human. In some embodiments, the single cell eukaryotic parasite is *Toxoplasma gondii*.

Still other aspects of the invention include methods for controlling a single celled eukaryotic parasite, comprising the steps of: identifying a single celled eukaryotic parasite, wherein the parasite has a translation complex and the translation complex has a wild type phosphorylation pattern; and altering the phosphorylation pattern of the translation complex in the single celled eukaryotic parasite. In some embodiments, the single eukaryotic parasite to be altered or controlled is selected from the group consisting of: *Toxoplasma, Plasmodium*, and *Cryptosporidium*. In some embodiments, altering the parasite includes introducing a change into the genome of the parasite. In still other embodiments, altering the parasite may include providing at least one compound that interferes with the phosphorylation pattern of at least one component of the translation complex, e.g. contacting at least one component of the translation complex with a compound that inhibits either phosphorylation or de-phosphorylation. In some embodiments the compound is salubrinal.

BRIEF DESCRIPTION OF THE SEQUENCES

SEQ. ID NO. 1 provides primer 5' S71A for+NotI.

SEQ. ID NO. 2 provides primer 5' S71A rev+BamHI.

SEQ. ID NO. 3 provides primer 3' S71A for+BclI.

SEQ. ID NO. 4 provides primer 3' S71A rev+BclI.

SEQ. ID NO. 5 provides primer TgIF2α S71A quikchange 1F.

SEQ. ID NO. 6 provides primer TgIF2α S71A quikchange 1R.

SEQ. ID NO. 7 provides primer S71A screen for.

SEQ. ID NO. 8 provides primer S71A screen rev.

SEQ. ID NO. 9 provides primer TgIF2α Taqman for.

SEQ. ID NO. 10 provides primer TgIF2α Taqman rev.

SEQ. ID NO. 11 provides primer FAM-WT TgIF2α.

SEQ. ID NO. 12 provides primer VIC-TgIF2α-S71A.

SEQ. ID NO. 13 provides the cDNA sequence for TgIF2KD.

SEQ. ID NO. 14 provides an alignment of TgIF2K-D protein kinase domain with other eIF2α kinases.

SEQ. ID NO. 15 provides an alignment of TgIF2K-C protein kinase domain with other eIF2α kinases.

SEQ. ID NO. 16 provides an alignment of NcIF2K-D protein kinase domain with other eIF2α kinases.

SEQ. ID NO. 17 provides an alignment of PfeIk1 protein kinase domain with other eIF2α kinases.

SEQ. ID NO. 18 provides an alignment of Pf14__0264 protein kinase domain with other eIF2α kinases.

SEQ. ID NO. 19 provides an alignment of PbeIK1 protein kinase domain with other eIF2α kinases.

SEQ. ID NO. 20 provides an alignment of TbeIF2K1 protein kinase domain with other eIF2α kinases.

SEQ. ID NO. 21 provides an alignment of AtGCN2 protein kinase domain with other eIF2α kinases.

SEQ. ID NO. 22 provides an alignment of DmGCN2 protein kinase domain with other eIF2α kinases.

SEQ. ID NO. 23 provides an alignment of ScGCN2 protein kinase domain with other eIF2α kinases.

SEQ. ID NO. 24 provides an alignment of MmGCN2 protein kinase domain with other eIF2α kinases.

SEQ. ID NO. 25 provides an alignment of HsGCN2 protein kinase domain with other eIF2α kinases.

SEQ. ID NO. 26 provides an alignment of TgIF2K-D with RWD domains from other GCN2 protein kinases.

SEQ. ID NO. 27 provides an alignment of NcIF2K-D with RWD domains from other GCN2 protein kinases.

SEQ. ID NO. 28 provides an alignment of Pf14__0264 with RWD domains from other GCN2 protein kinases.

SEQ. ID NO. 29 provides an alignment of MmGCN2 with RWD domains from other GCN2 protein kinases.

SEQ. ID NO. 30 provides an alignment of DmGCN2 with RWD domains from other GCN2 protein kinases.

SEQ. ID NO. 31 provides an alignment of ScGCN2 with RWD domains from other GCN2 protein kinases.

SEQ. ID NO. 32 provides an alignment of the C-terminal homology region of TgIF2K-D with other predicted GCN2-like protein kinases from parasites.

SEQ. ID NO. 33 provides an alignment of the C-terminal homology region of NcIF2K-D with other predicted GCN2-like protein kinases from parasites.

SEQ. ID NO. 34 provides an alignment of the C-terminal homology region of Cmu__027700 with other predicted GCN2-like protein kinases from parasites.

SEQ. ID NO. 35 provides an alignment of the C-terminal homology region of PF14__0264 with other predicted GCN2-like protein kinases from parasites.

SEQ. ID NO. 36 provides an alignment of the C-terminal homology region of Pb__101620 with other predicted GCN2-like protein kinases from parasites.

SEQ. ID NO. 37 provides an alignment of the C-terminal homology region of PkH__113740 with other predicted GCN2-like protein kinases from parasites.

SEQ. ID NO. 38 provides an alignment of the C-terminal homology region of Pvx__085120 with other predicted GCN2-like protein kinases from parasites.

SEQ. ID NO. 39 provides the TgIF2K-D primer 1.

SEQ. ID NO. 40 provides the TgIF2K-D primer 2.

SEQ. ID NO. 41 provides the TgIF2K-D primer 3.

SEQ. ID NO. 42 provides the TgIF2K-D primer 4.

SEQ. ID NO. 43 provides the TgIF2K-D primer 5.

SEQ. ID NO. 44 provides the TgIF2K-D primer 6.

SEQ. ID NO. 45 provides the TgIF2K-D primer 7.

SEQ. ID NO. 46 provides the TgIF2K-D primer 8.

SEQ. ID NO. 47 provides the TgIF2K-D primer 9.

SEQ. ID NO. 48 provides the TgIF2K-D primer 10.

SEQ. ID NO. 49 provides the TgIF2K-D primer 11.

SEQ. ID NO. 50 provides the TgIF2K-D primer 12.

SEQ. ID NO. 51 provides the TgIF2K-D primer 13.

SEQ. ID NO. 52 provides the TgIF2K-D primer 14.

SEQ. ID NO. 53 provides the TgIF2K-D primer 15.

SEQ. ID NO. 54 provides the TgIF2K-D primer 16.

SEQ. ID NO. 55 provides the TgIF2K-D primer 17.

SEQ. ID NO. 56 provides the TgIF2K-D primer 18.

SEQ. ID NO. 57 provides the TgIF2K-D primer 19.

SEQ. ID NO. 58 provides the TgIF2K-D primer 20.

SEQ. ID NO. 59 provides the TgIF2K-D primer 21.

SEQ. ID NO. 60 provides the TgIF2K-D primer 21N.

SEQ. ID NO. 61 provides the TgIF2K-D primer 22.

SEQ. ID NO. 62 provides the TgIF2K-D primer 22N.

SEQ. ID NO. 63 provides the TgIF2K-D primer 23.

SEQ. ID NO. 64 provides the TgIF2K-D primer 23N.

SEQ. ID NO. 65 provides the TgIF2K-D primer 24.

SEQ. ID NO. 66 provides the TgIF2K-D primer 25.

SEQ. ID NO. 67 provides the TgIF2K-D primer 26.

SEQ. ID NO. 68 provides the TgIF2K-D primer 27.

SEQ. ID NO. 69 provides the TgIF2K-D primer 28.

SEQ. ID NO. 70 provides the TgIF2K-D primer 29.

BRIEF DESCRIPTION OF THE FIGURES

FIGS. 12A-C show the cDNA sequence for TgIF2K-D.

FIG. 15. Alignment of TgIF2K-D with RWD domains from other GCN2 protein kinases.

FIG. 16. Alignment of the C-terminal homology region of TgIF2K-D with other predicted GCN2-like protein kinases from parasites.

DESCRIPTION

Figure 1A:
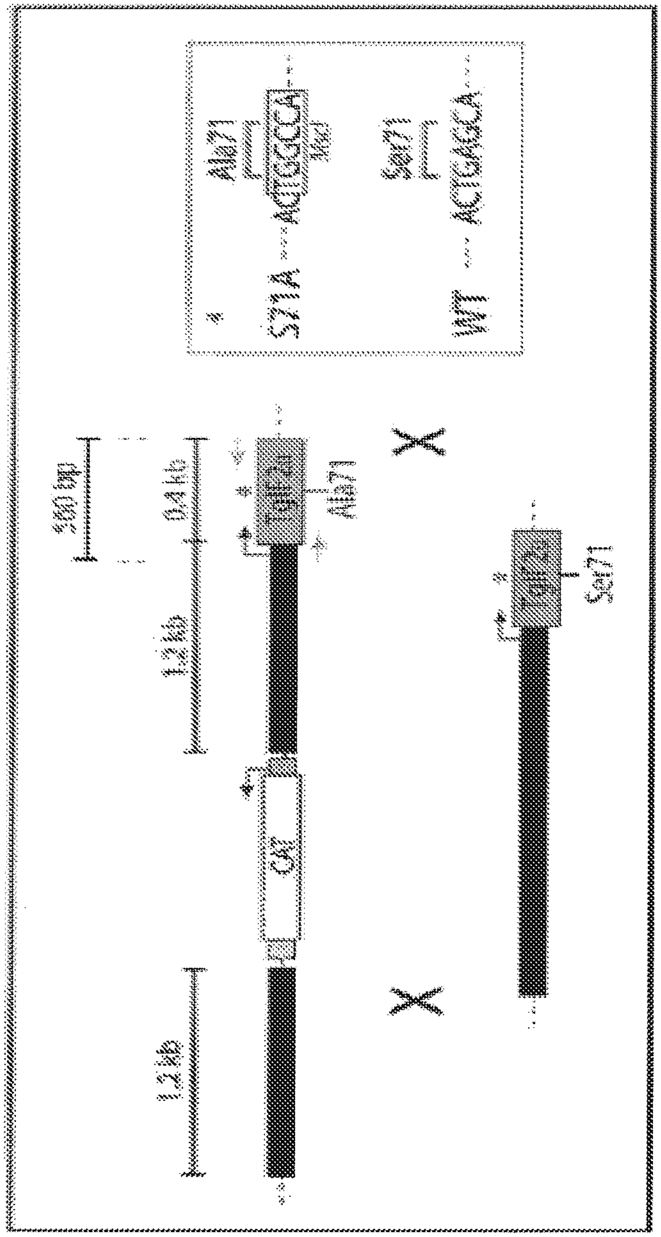
FIG. 1A. Diagram depicting the relevant portion of the TgIF2α genomic locus and the TgIF2α-S71A allelic replacement vector.

For the purposes of promoting an understanding of the principles of the novel technology, reference will now be made to the preferred embodiments thereof, and specific language will be used to describe the same. It will nevertheless be understood that no limitation of the scope of the novel technology is thereby intended; such alterations, modifications, and further applications of the principles of the novel technology being contemplated as would normally occur to one skilled in the art to which the novel technology relates are within the scope of the claimed invention.

Unless clearly stated or implied otherwise the term "about" as used herein means plus or minus 10 percent. For example, the term about 1.0 encompasses a range of values from 0.9 to 1.1.

The lytic cycle of *Toxoplasma* tachyzoites can be described as comprising three discrete stages: adherence to a host cell, invasion, replication, exit from host cell (egress), and movement to a new host cell (Black and Boothroyd, 2000). Tachyzoites remain viable for only a limited time outside of the host cell; the ability of freshly egressed parasites to infect a new host cell monolayer drops significantly between 6-12 hrs of exposure to the extracellular environment (Khan et al., 2009). The mechanisms that the parasite may invoke in order to cope with the extracellular environment while it searches for a new host cell are not well known.

One well characterized stress response pathway conserved in many eukaryotic cells types involves translational control by virtue of the phosphorylation of the alpha subunit of eukaryotic initiation factor-2 (eIF2α) (Sonenberg and Hinnebusch, 2009; Wek et al., 2006). The protein eIF2-GTP escorts Met-$tRNA_i$ to the translational machinery for eventual placement into the P-site of ribosomes (Sonenberg and Hinnebusch, 2009); however, in many organisms when it is phosphorylated at a regulatory serine (serine-51), eIF2 becomes an inhibitor of its guanine nucleotide exchange factor, eIF2B. Consequently, global translation initiation is reduced when eIF2α is phosphorylated which, in turn decrease the synthesis of the current proteome. Globally decreasing the amount of protein synthesised by the cell enables the cell to conserve energy and it may aid the cell in reprogramming its gene translation pattern as necessary to address the conditions that are stressing the cell (Wek and Cavener, 2007a). Four eIF2 kinases have been identified in mammals that phosphorylate eIF2α in response to stress (Wek and Cavener, 2007b; Wek et al., 2006): HRI (EIF2KA1), which responds to heme-deficiency and oxidation stress; PKR (EIF2KA2), which is involved in anti-viral defences; PEK/PERK (EIF2KA3), which is activated by endoplasmic reticulum (ER) stress; and GCN2 (EIF2KA4), which responds to nutrient deprivation. An eIF2α orthologue, as well as four TgIF2α kinases (TgIF2K-A through -D) were identified in *Toxoplasma* (TgIF2α). (Narasimhan et al., 2008a; Sullivan Jr. et al., 2004a). While TgIF2K-C and -D are most closely related to GCN2, TgIF2K-A in the parasite is localized to its ER where it likely mediates the activation of the unfolded protein response (UPR) analogous to PEK/PERK (Narasimhan et al., 2008a). TgIF2K-B is a novel eIF2 kinase that is not compartmentalized and likely responds to cytoplasmic stresses. Homologues of GCN2 (PfeIK1) and TgIF2K-A (PfPK4) have also been described in *Plasmodium* (malarial) parasites (Fennell et al., 2009; Mohrle et al., 1997).

The importance of eIF2α phosphorylation in general and gene-specific translation in the adaptive processes to stress have been determined in yeast and in some mammalian systems by allelic gene replacement involving, for example, the substitution of alanine for the serine-51 the site of phosphorylation in eIF2α (S51A) (Dever et al., 1992; Hinnebusch, 2005; Scheuner et al., 2001; Schroder and Kaufman, 2005b). As disclosed herein, a mutant parasite incapable of phosphorylating eIF2α was engineered by substituting alanine for the regulatory serine (Ser-71) in TgIF2α and characterized. TgIF2α-S71A mutant parasites have decreased viability in vitro and are less virulent in a mouse model of infection. The underlying mechanism for the growth defect does not appear to involve parasite attachment, invasion, replication, egress, or motility, but rather it is due to the impaired ability of the parasites to manage the stress caused by their exposure to the extracellular environment. These results provide significant new insights into how intracellular parasites survive while they attempt to locate a new host cell.

Generation of Mutant *Toxoplasma* Incapable of Phosphorylating TgIF2α

The *Toxoplasma* eIF2α orthologue (TgIF2α), possesses a conserved regulatory serine residue (Ser-71) that is phosphorylated during cellular stress (Sullivan Jr. et al., 2004b was previously characterized). In order to access the impact of TgIF2α phosphorylation in *Toxoplasma* tachyzoites, a mutant parasite line in which the Ser-71 residue of TgIF2α was changed to alanine was generated. The TgIF2α-S71A mutation was created by allelic replacement using homologous recombination in RHΔKu80 parasites (Fox et al., 2009; Huynh and Carruthers, 2009). Referring now to FIG. 1A, the dark grey box denotes the beginning of the TgIF2α genomic locus and the black box represents ~2.4 kb of upstream sequence. The serine-71 codon (AGC) was mutated to an alanine codon (GCC) which created a unique MscI restriction site within the mutant allele. RHΔKu80 parasites were transfected with a 'knock-in' construct that included a point mutation encoding the S71A substitution along with a mini-gene that encoded chloramphenicol resistance. The point mutation generated a unique MscI restriction site in the TgIF2α genomic locus, which was used as a means to select for true allelic replacements among the chloramphenicol-resistant clones. Screening was performed by amplifying a fragment of the first exon in the TgIF2α genomic locus and cutting the amplicon with MscI.

Figure 1B:
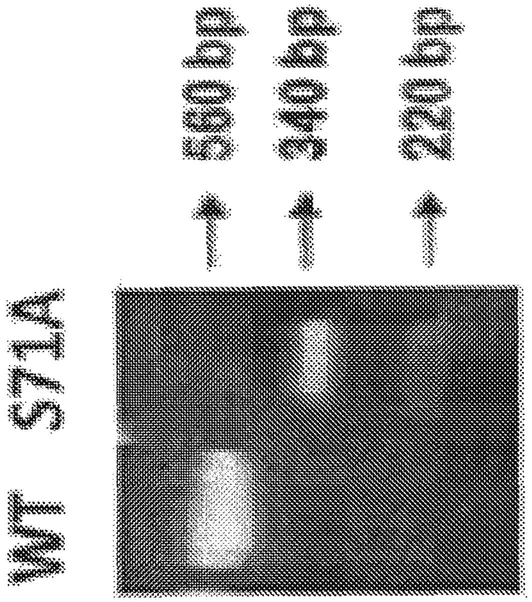
FIG. 1B. Agarose gel showing wild type and S71A alleles measured in mutation.

Referring now to FIG. 1B, the first exon of the TgIF2α gene was amplified from WT and TgIF2α-S71A parasites (PCR primers shown in grey in FIG. 1A). The resulting PCR product was digested with MscI and resolved on 1% agarose gel. In a true allelic replacement, two products (340 and 220 bp) would be visualized instead of one (560 bp). The MscI-digested PCR product from parental RHΔKu80 parasites (hereafter referred to as "wild-type" (WT)) yields a single DNA fragment of 560 bp; however, two fragments of 340 and 220 bp are produced after allelic replacement. Two independent clones containing the S71A knock-in within the endogenous TgIF2α genomic locus were identified, and both exhibited similar phenotypic properties as described below.

Figure 1C:
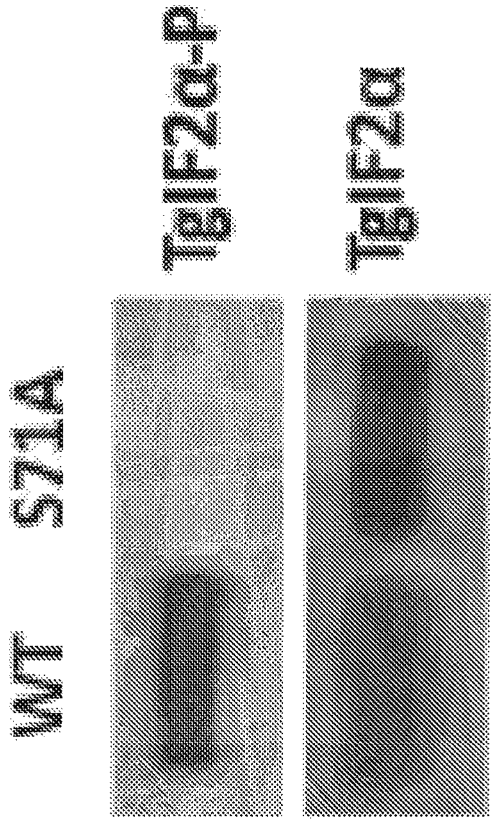
FIG. 1C. Western blot of WT and S71A lysates showing that S71A cannot be phosphorylated.

In order to confirm that the TgIF2α-S71A clone could not be phosphorylated under normal physiological condition, a Western blot of lysates from parasites treated with the ionophore A23187 was carried out using antisera that specifically recognizes TgIF2α which is phosphorylated at ser-71 or total TgIF2α protein (Narasimhan et al., 2008b; Sullivan Jr. et al., 2004b). Referring now to FIG. 1C, equal amounts of protein lysates from WT or TgIF2α-S71A tachyzoites were resolved on a 4-12% polyacrylamide gel and transferred to a membrane for immunoblotting with antibody that specifically recognizes TgIF2α phosphorylated at ser-71 (TgIF2α-P) or total TgIF2α protein. The ionophore A23187 produces ER stress, and consistent with a previous study, this ionophore is a potent inducer of TgIF2α phosphorylation in wild-type parasites (Narasimhan et al., 2008b). By comparison, phosphorylation is absent in the TgIF2α-S71A mutant parasites that have been exposed to the ionophore A23187 (FIG. 1C). These results confirm that a mutant version of *Toxoplasma* that cannot phosphorylate eIF2α was created.

TgIF2α-S71A Parasites Exhibit Reduced Growth In Vitro

Figure 2A:
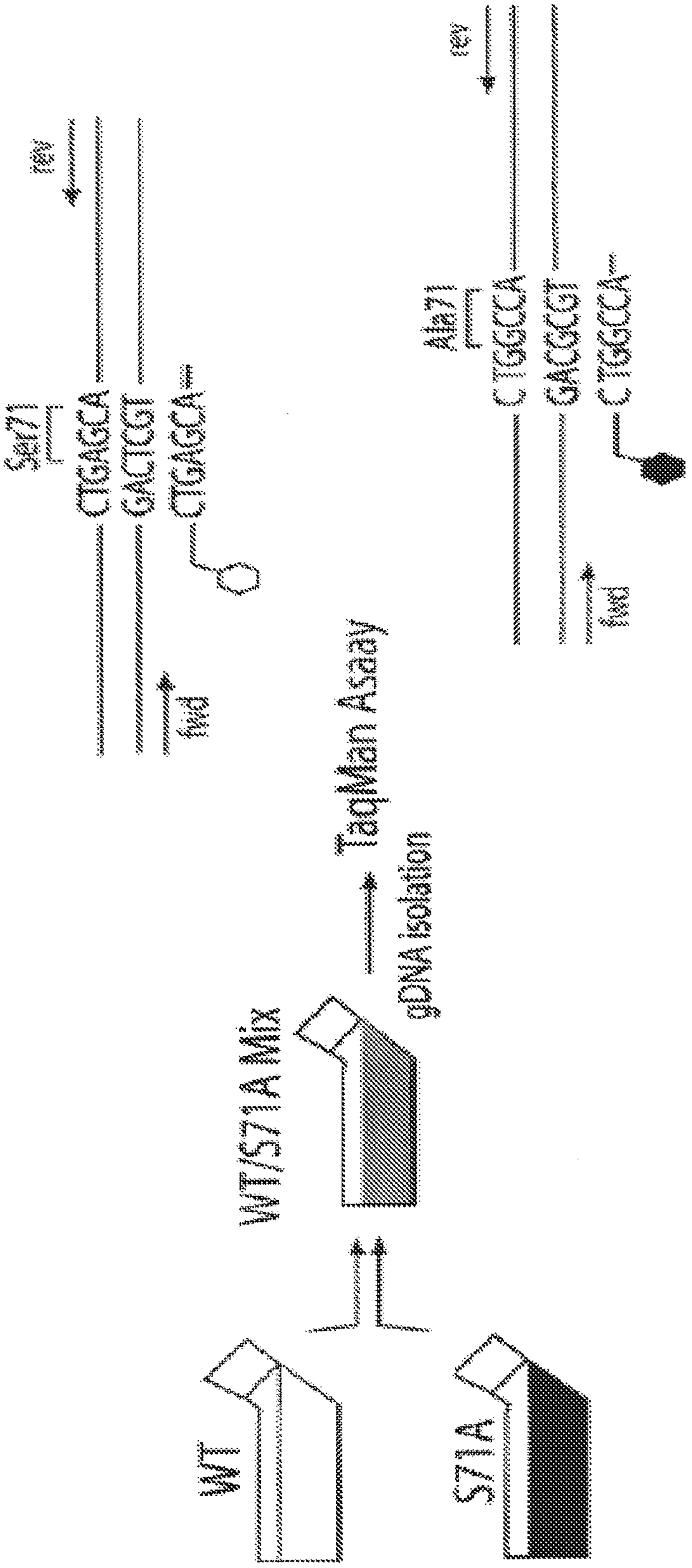
FIG. 2A. Diagram of parasite fitness assay.

Observational analysis suggests that the TgIF2α-S71A parasites take longer to lyse monolayers of host cells than do wild-type parasites. In order to directly assess whether the mutant parasites were less fit for survival than were the comparable to wild-type organisms, "head-to-head" competition assays were carried out (Fohl and Roos, 2003). Referring now to FIG. 2A, equal numbers of WT and TgIF2α-S71A parasites (shown as white and black, respectively) were grown in mixed culture in a T25-flask (gray). Every three days the parasites were removed from the host cells by physically scraping the monolayer. Recovered parasites were then passed onto a fresh monolayer. On the day of passage, a sample was collected for genomic DNA (gDNA) isolation. The gDNA was used as a template for a TaqMan-based fitness assay designed to distinguish WT and mutant parasites. This assay used two probes, WT-TgIF2α-FAM (shown in white) was used to detect the WT allele, while S71A-TgIF2α-VIC (shown in black) was used to identify the mutant (S71A) allele. The S71A mutants were created according to the methods disclosed herein. An essentially equal number of wild-type and TgIF2α-S71A parasites were inoculated into the same culture flask. The standard comparative fitness assay was modified in order to take advantage of TaqMan probes and real-time PCR as a means of distinguish between the wild-type (WT-TgIF2α-FAM) and mutant (S71A-TgIF2α-VIC) alleles of the TgIF2α gene.

Figure 2B:
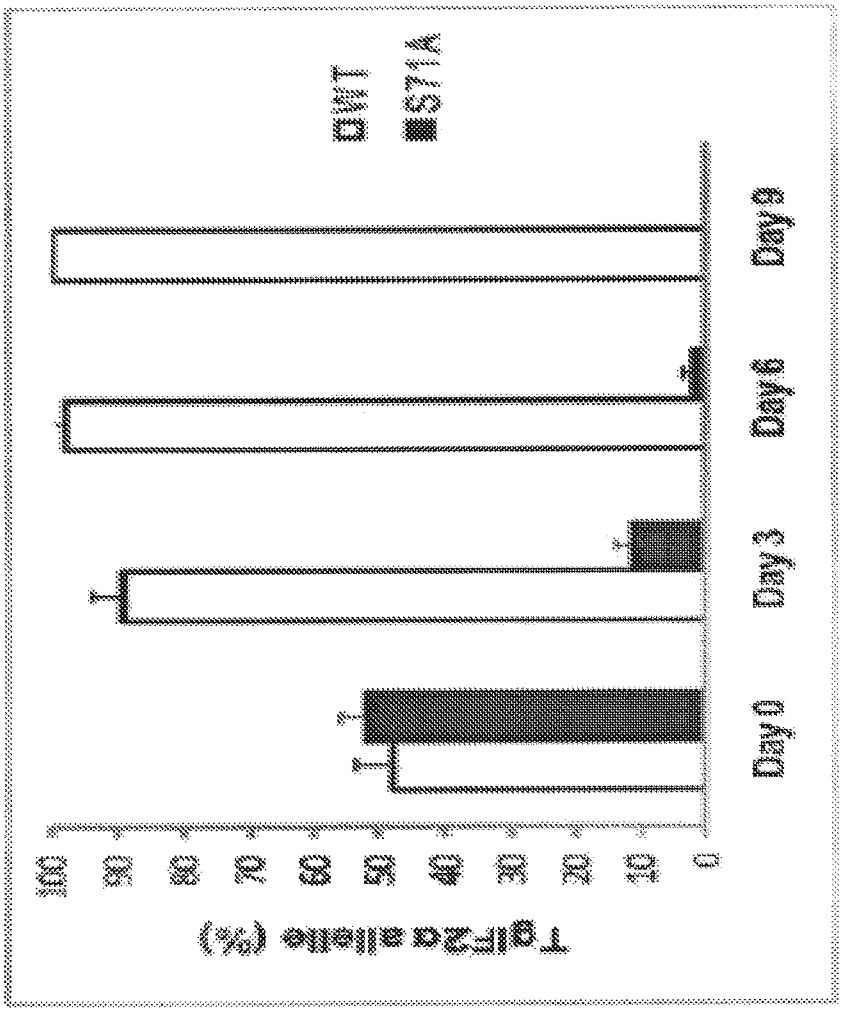
FIG. 2B. Bar graph of the percentage of WT and S71A parasites in co-culture at days 0, 3, 6 and 9.

Referring now to FIG. 2B, the percentage of the WT and S71A mutant allele was determined using SDS software version 1.2.1 (Applied Biosystems) and plotted for each day sampled (white bars, WT; black bars, S71A). C $10^4$ parasites were cultured in 12-well plates that had confluent HFF monolayers. The percentage of host cell lysis was evaluated at days 5, 6, and 7 respectively by washing each well with PBS buffer and staining the remaining host cells with Coomassie Brilliant Blue. A digital image of each well was recorded and analyzed using Alpha Innotech software to determine the percent of the monolayer disrupted by either WT or TgIF2α-S71A mutant parasites, represented respectively by either white or black bars. Genomic DNA was collected and examined at the time of inoculation (day 0), and then sampled again every three days. At day 0, the PCR analysis showed that equal numbers of TgIF2α-S71A and wild-type parasites were present in the mixed culture. However, by day three the mutants were significantly outgrown by the wild-type organisms. And by day nine, TgIF2α-S71A mutant parasites could no longer be detected in the culture.

Figure 2C:
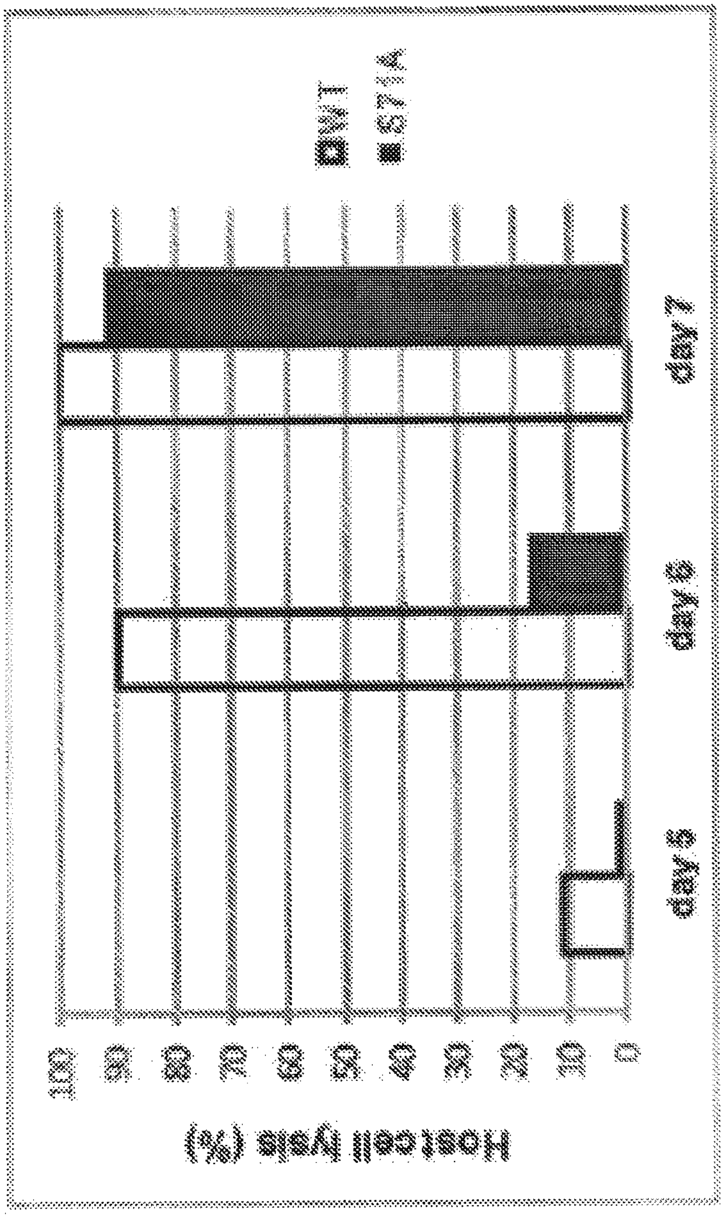
FIG. 2C shows a bar graph for host cell lysis (%) at days 5, 6, and 7.

Referring now to FIG. 2C, WT and S71A mutant parasites were allowed to adhere/invade a monolayer of HFF cells for 30 min. Adhered (extracellular) parasites were visualized with a mouse anti-Sag1 immune sera (green parasites). Following permeabilization, both intracellular (invaded) and extracellular parasites were visualized with a rabbit anti-Sag1 antibody (red parasites). In the merged image, adhered parasites appear yellow and invaded parasites are red. The number of adhered (yellow) and invaded (red) parasites per microscope field were plotted for both WT and S71A parasites (bottom panel). A standard parasite growth assay that examined the extent of host cell monolayer disruption over time was also performed. Six days after inoculation about 90% of wild-type parasites lyse out of the host cell monolayer but in the same six day period an equal number of TgIF2α-S71A parasites had only destroyed ~18% of the host cells in the monolayer. It took the mutant parasites until day to destroyed ~90% of the host cell monolayer, a full 24 hours slower than wild-type parasites. Together, these results indicate that TgIF2α phosphorylation is important in order for *Toxoplasma* tachyzoites to progress normally through host cell cultures.

Figure 3:
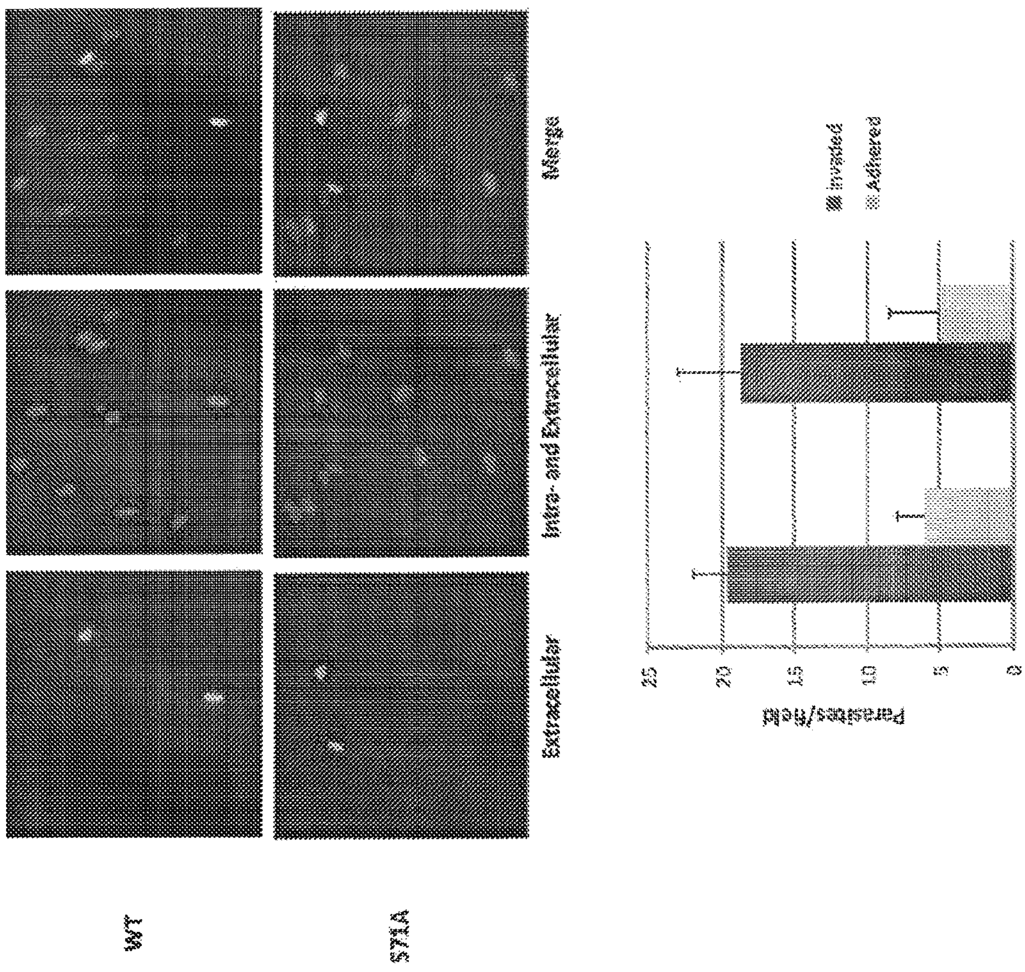
FIG. 3. Results of attachment and invasion assays run on WT and S71A parasites.

TgIF2α-S71A Parasites are Defective in Adapting to the Extracellular Environment In order to try and identify the cause of the growth retardation in the TgIF2α-S71A mutant, each step in the tachyzoite lytic cycle was examined. Referring now to FIG. 3, WT and S71A mutant parasites were allowed to adhere/invade a monolayer of HFF cells for 30 min. Adhered (extracellular) parasites were visualized with a mouse anti-Sag1 immune sera (green parasites). Following permeabilization, both intracellular (invaded) and extracellular parasites were visualized with a rabbit anti-Sag1 antibody (red parasites). In the merged image, adhered parasites appear yellow and invaded parasites are red. The number of adhered (yellow) and invaded (red) parasites per microscope field were plotted for both WT and S71A parasites (bottom panel). Using a standard red/green attachment and invasion assay, no detected difference was observed in the ability of TgIF2α-S71A mutants to adhere or penetrate host cells.

Figure 4A:
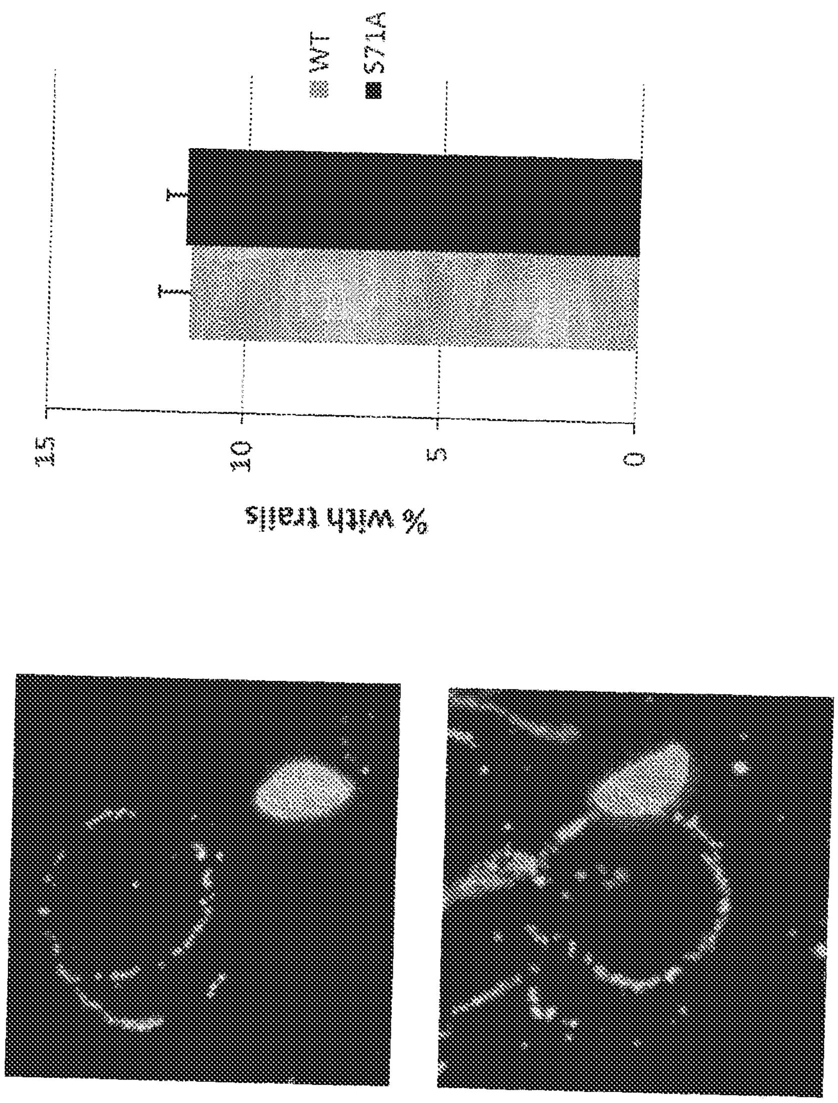
FIG. 4A. Photo micrograph of trails measured with WT and S71A mutants (right); graph of the percentage of parasites with trails (left).
Figure 4B:
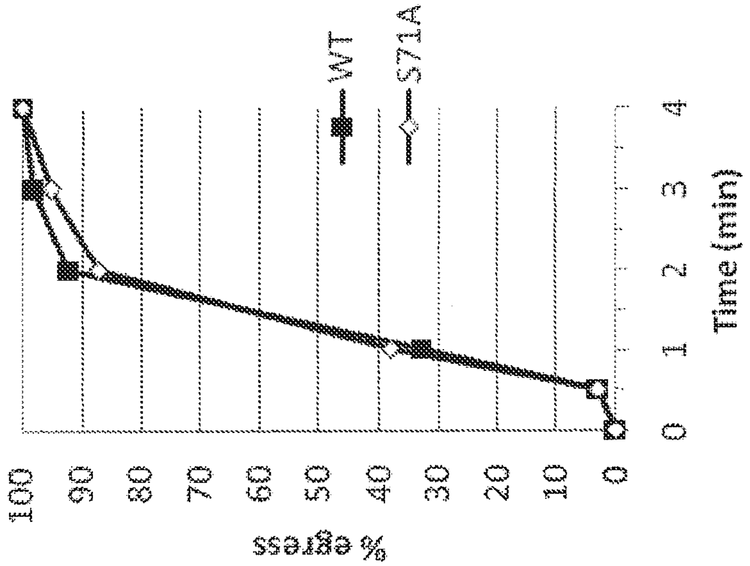
FIG. 4B. Graph of % egress versus time (mins.) for both wild type and S71A parasites.

Referring now to FIG. 4A, the WT and S71A mutant parasites were allowed to adhere and glide along a glass coverslip for 30 min. The parasites and surface protein 'trails' were detected with mouse anti-Sag1. The percentage of parasites with 'trails' was plotted for both WT parasites (grey bar) and the S71A mutant (black bar). No defect in gliding motility was found nor was any detected. Referring now to FIG. 4B, WT and S71A parasites were cultured overnight in a monolayer of HFF cells. In order to induce egress, the infected monolayers were exposed to 2 μM for A23187 for 0, 0.5, 1, 2, 3, or 4 min. Following each time interval a sample was taken and the parasites in the samples were fixed with cold methanol. Finally, using the parasite counts that were obtained the percentage of egress was calculated for the WT (black boxes) and S71A parasites (white circles).

The ability of TgIF2α-S71A parasites to exit from host cells upon ionophore-induced egress was not compromised. With no measurable defects in their ability to either enter or exit host cells, two not mutually exclusive possibilities remain which may help to explain why WT parasites overgrow TgIF2α-S71A parasites, there are: 1) the TgIF2α-S71A mutants are be defective in asexual replication, and 2) exposure to the extracellular environment produces a stress that TgIF2α-S71A mutants are ill-equipped to withstand. In order to test these possibilities, two independent types of parasite growth measurements were carried out: plaque assays and doubling assays. In order to obtain a homogenous population of parasites that had nominal exposure to the extracellular environment, intracellular parasites were physically separated from their host cells.

Figure 5A:
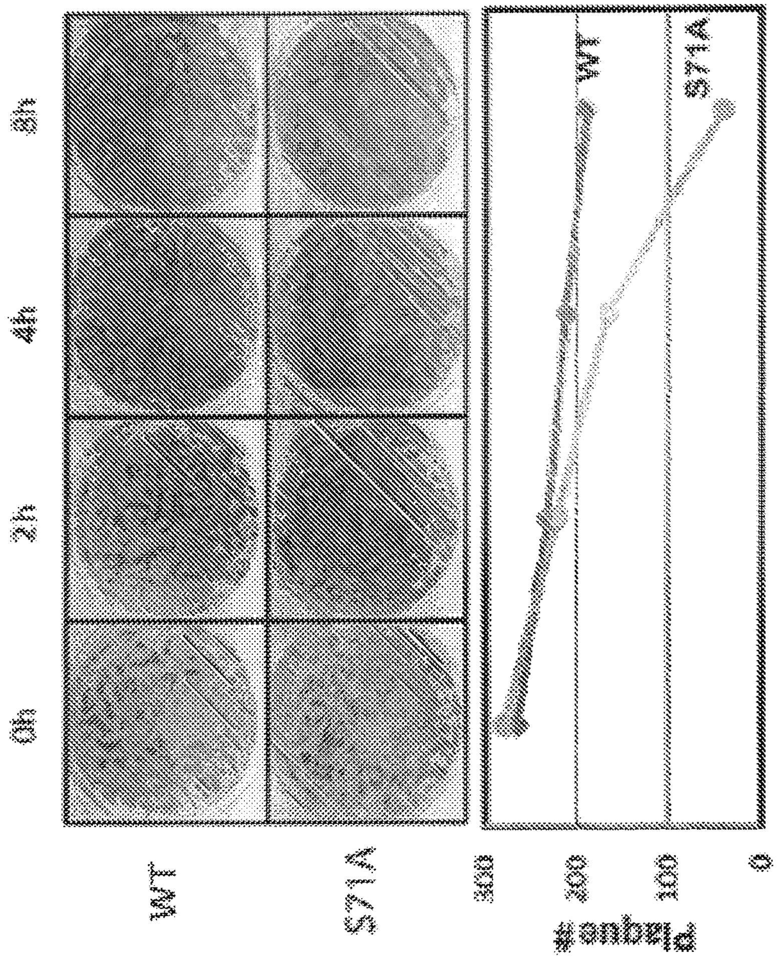
FIG. 5A. Coomassie Brilliant Blue Stained plaques created with either wild type or S71A parasites (Top); measured 8, 16, 24 and 32 hrs. post inoculation (bottom).

Referring now to FIG. 5A, intracellular WT and TgIF2α-S71A parasites were physically removed from host cells and then incubated without host cells in DMEM plus 1% FBS at 37° C. in 5% $CO_2$ for 0, 2, 4, or 8 hr. Following each time point, $5\times10^2$ parasites were passed onto a fresh HFF monolayer in a 12-well plate. Upon plaque formation, each well was washed with PBS and stained with Coomassie Brilliant Blue (upper panel). The number of plaques formed by the WT (diamonds) or TgIF2α-S71A mutants (squares) were counted using Alpha Innotech imaging software and plotted on a line graph (lower panel). The freed tachyzoites were immediately passed onto a fresh HFF monolayer (0 h), or deprived of host cells by incubating in extracellular medium for 2, 4, or 8 hr. Without appreciable exposure to the extracellular environment consisting of DMEM plus 1% FBS (0 hr), wild-type and TgIF2α-S71A mutants formed a near identical number of plaques, suggesting that the inability to phosphorylate TgIF2α has no appreciable impact on parasite replication. However, TgIF2α-S71A mutants were much more sensitive to being deprived of their host cells. Compared to wild-type, TgIF2α-S71A mutants showed a significant reduction in plaque numbers following an 8 hour exposure to the extracellular environment.

Figure 5B:
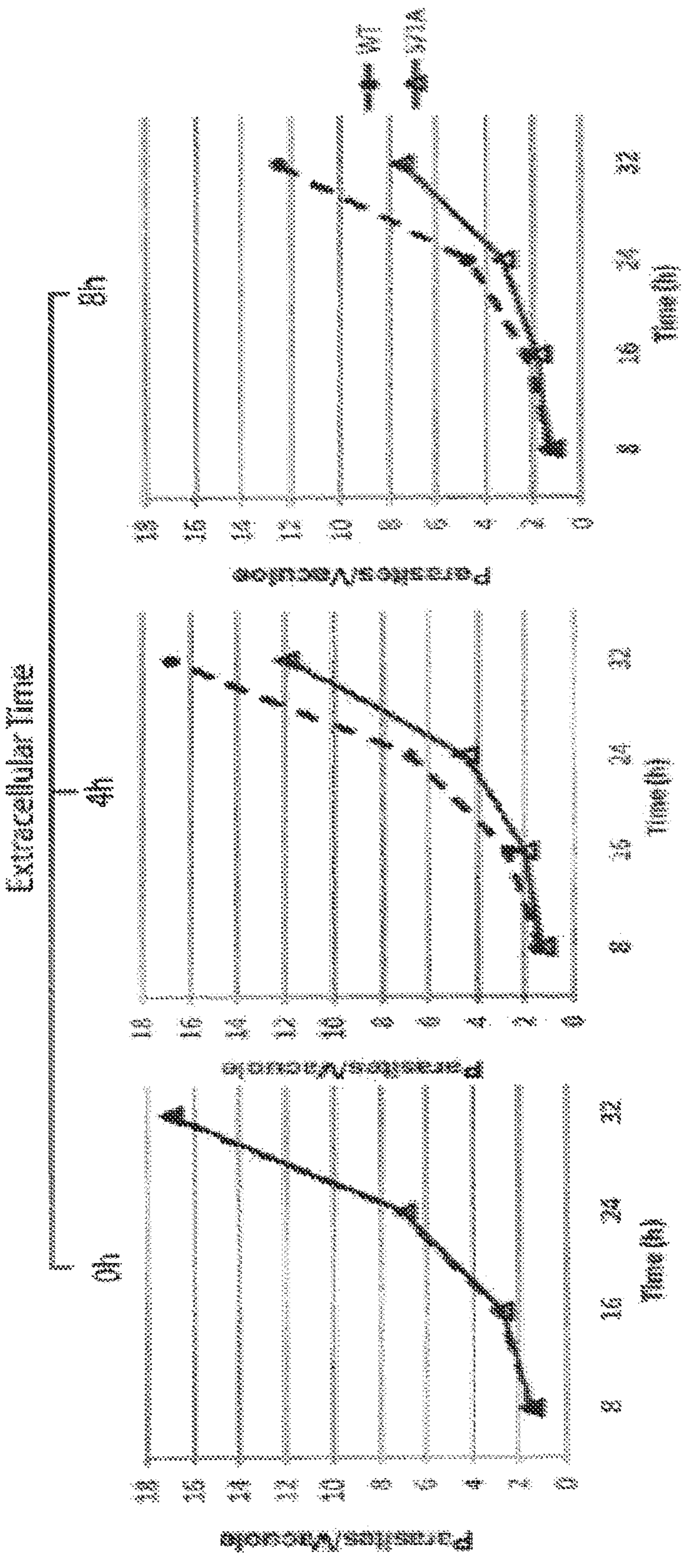
FIG. 5B. Graph of parasites/vacuole measured for both WT and S71A parasites at three different times.

Referring now to FIG. 5B, using the same method above, WT and TgIF2α-S71A mutants were deprived of host cells for 0, 4, or 8 hours and then allowed to infect a fresh HFF monolayer. *Toxoplasma* growth was quantitated using a standard parasite doubling assay. The average number of parasites/vacuole is displayed for each counting period (8, 16, 24, and 32 hours post-inoculation). Next the doubling time of wild-type and TgIF2α-S71A mutant parasites was measured. The parasites were immediately passed into fresh host monolayers (0 hours of extracellular exposure). Both grew at a similar rate during the 32 hour time course. As observed in the plaque assay, the inability to phosphorylate TgIF2α compromises the ability of the parasite to recover from the stress of the extracellular exposure. Wild-type parasites deprived of host cells for 8 hours have an average number of 12 parasites/vacuole 32 hours post-inoculation, whereas TgIF2α-S71A mutants only achieve an average of 7 parasites per vacuole.

Figure 5C:
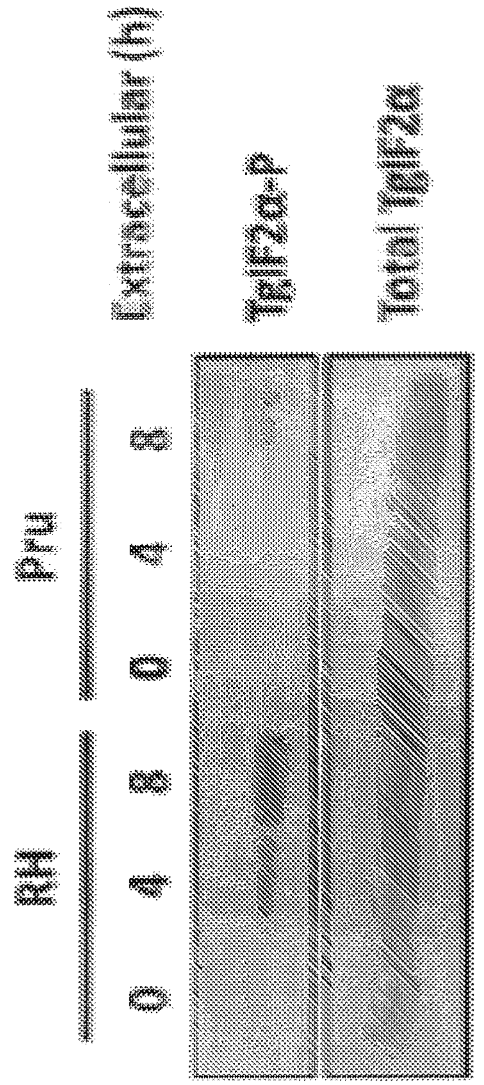
FIG. 5C. Western blot of lysates.

These studies suggest that following egress, TgIF2α becomes phosphorylated in order to help the parasite\ cope with the extracellular environment until it invades a new host cell. Referring now to FIG. 5C, protein lysates were generated from RH and Pru parasites deprived of the host cell for 0, 4, or 8-hr. A Western blot was carried out using equal amounts of protein lysate with antibodies that specifically recognize phosphorylated TgIF2α or total TgIF2α protein. Consistent with this idea, it was found that phosphorylation of TgIF2α increases during increased exposure to the extracellular environment. Interestingly, TgIF2α phosphorylation was more significantly induced in type I (RH) parasites compared to a type II (Pru) strain following exposure to the extracellular environment.

Translation by Incubating Extracellular Wild-Type and TgIF2α-S71A Tachyzoites in Medium Containing [$^{35}$S] Met/Cys Radiolabel.

Figure 5D:
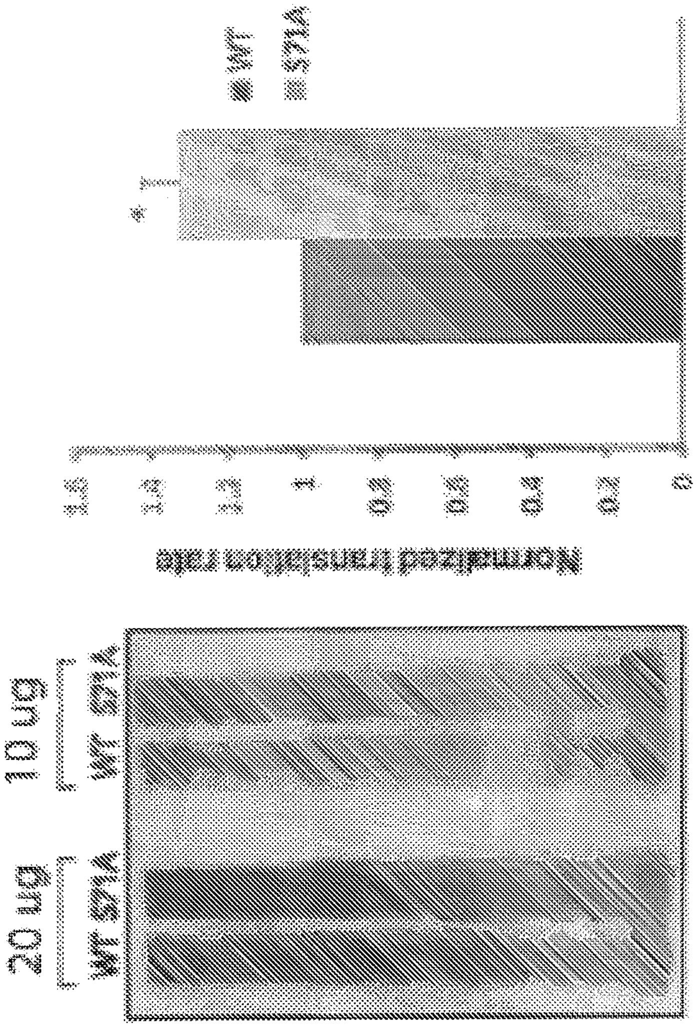
FIG. 5D. SDS-PAGE autoradiograph [$^{35}$S]met/cys. translation rates.

Referring now to FIG. 5D, Extracellular WT or TgIF2α-S71A tachyzoites were incubated in the presence of [$^{35}$S] Met/Cys for 30 min at 37° C. with 5% $CO_2$. Radiolabeled proteins were resolved on SDS-PAGE for autoradiography. Asterisks (*) denotes P-value $<0.05$. Radiolabeled parasite proteins were then resolved by SDS-PAGE and visualized by autoradiography. Wild-type parasites had lower levels of radiolabeled protein than did mutant parasites that harboured mutant TgIF2α-S71A. It is noted that this translation measurement was carried out in parasites cultured in the extracellular medium in the absence of an added stressing agent. This finding suggests that extracellular *Toxoplasma* tachyzoites experience a stress that elicits translational control. Parasites that have the TgIF2α-S71A mutant form of the protein are unable to readily reduce the rate at which they produce protein when stressed by exposure to the extracellular environment and this renders them less fit than parasites that have the wild type form of this protein.

Reduced Virulence of TgIF2α-S71A Parasites In Vivo

Since *Toxoplasma* that are incapable of phosphorylating eIF2α exhibit reduced fitness in vitro, the TgIF2α-S71A mutant was tested to determine if it had decreased virulence in vivo. In order to test this idea, 10 or 100 wild-type or TgIF2α-S71A mutant parasites were injected into female BALB/c mice immediately after the organisms egressed from human cell hosts. In this model for acute toxoplasmosis, hypervirulent RH strain *Toxoplasma* typically produces a moribund mouse within 7 days (168 hr). In this study, mice infected with 10 wild-type parasites become moribund at 167 hr, but mice infected with 10 TgIF2α-S71A parasites showed a 28 hour delay, not becoming moribund until 195 hours (Table I). The same delay in the course of infection occurred with a dosage of 100 parasites (Table I), leading the conclusion that TgIF2α phosphorylation and translation control enhances the virulence of *Toxoplasma* in vivo.

TABLE 1

| GROUP | SURVIVAL TIME, hr |
|---|---|
| WT (10 parasites) | 167 |
| S71A (10 parasites) | 195 |
| WT (100 parasites) | 147 |
| S71A (100 parasites) | 174 |

Characterization of the GCN2-Like Kinase TgIF2K-D

Figure 12A:
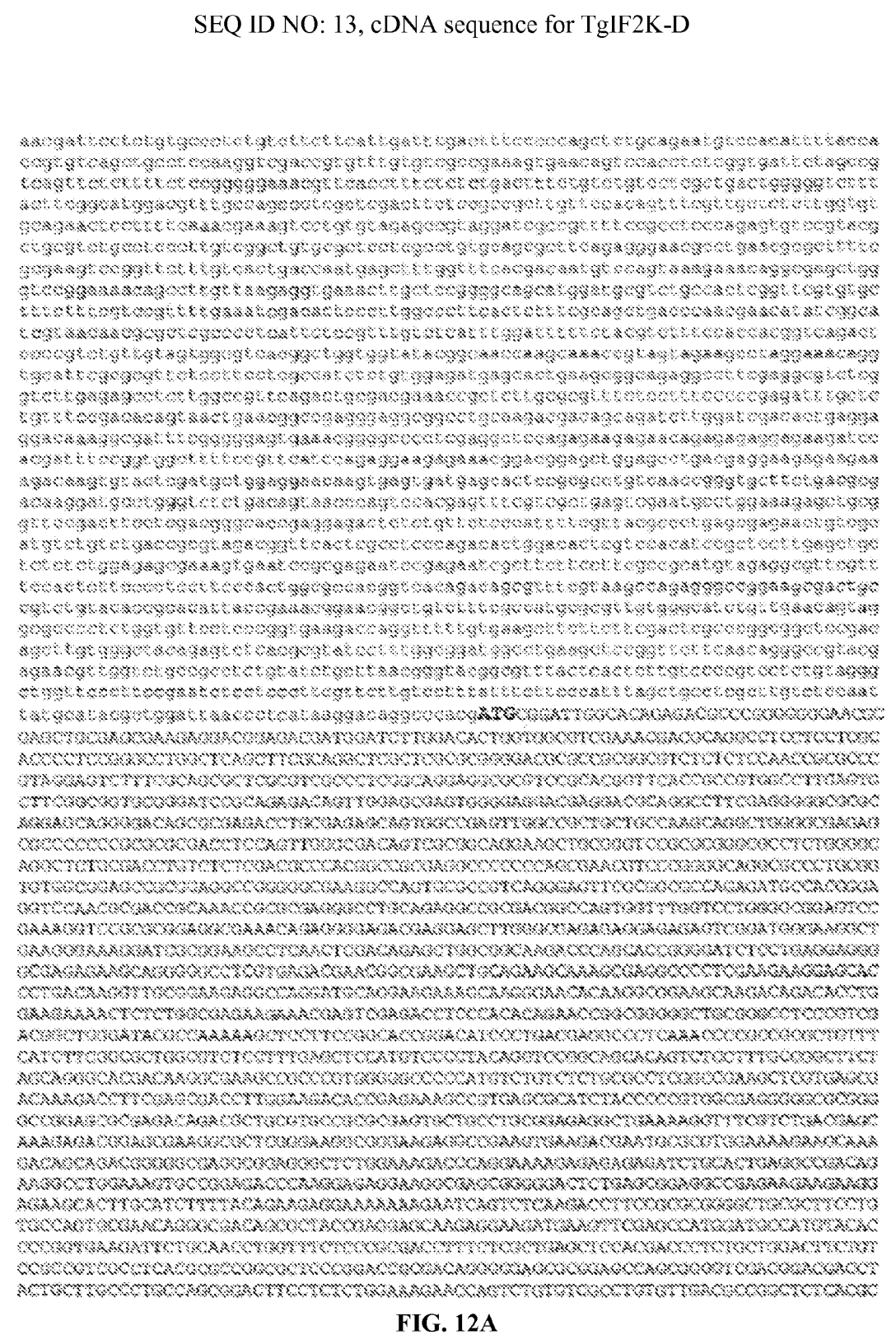

The predicted gene TgME49_119610 (ToxoDB.org) was previously designated TgIF2K-D and is suggested to be an orthologue of GCN2 (24), the eIF2α kinase that is well-documented as a responder to nutrient starvation stress in other species, RT-PCR was sued to identify and characterize the full-length TgIF2K-D cDNA. This analysis revealed a predicted TgIF2K-D product consisting of 2,729 amino acid residues (GenBank JF827031), which modifies the predicted sequence for TgME49_119610 due to a discrepancy at the exon3/intron3 boundary. Referring now to FIG. 12, TgIF2K-D cDNA contains an open reading frame (upper case letters) of 8,190 nucleotides and a 5'- and 3'-UTR (lower case letters) of 2,151 and 1,000 nucleotides, respectively. Start and stop codons are indicated by bold letters. The in-frame stop codon upstream of the start codon is underlined. The predicted start codon for the TgIF2K-D ORF matches the consensus sequence for translation initiation in *Toxoplasma* (35) and is preceded by an in-frame stop codon. RACE analyses indicated a 5'-untranslated region (UTR) of 2,151-bp, which is consistent with the transcriptional start site (TSS) derived from the Full-parasites database and ChIP-Chip data available in the ToxoDB, and a 3'UTR of 1,000 bp.

Figure 13:
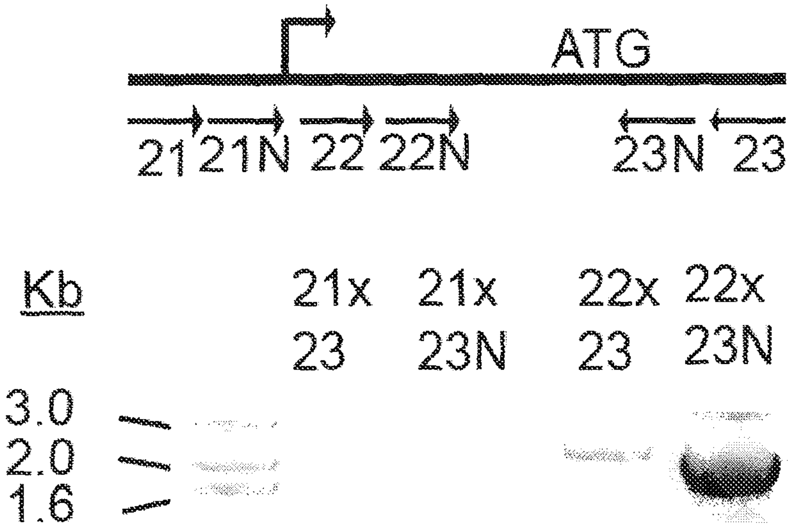
FIG. 13. Oligionucleotides used to determine the state site of the TgIF2K-D gene.

Referring now to FIG. 13, the 5'-UTR was further validated by RT-PCR using primers flanking the TSS. RT-PCR analysis to delineate the transcriptional start site of the TgIF2K-D gene. Oligonucleotide primers complementary to sequences upstream (#21) and downstream (#22) of the transcriptional start site (arrow), as well as downstream of the start codon (#23) were designed to verify the 5'-end of the TgIF2K-D mRNA as determined by 5'RACE. PCR assays were carried out using oligonucleotides primers #21 and #23, or #22 and #23. These PCRs were then nested with oligonucleotides #21N and #23N, or #22N and #23N, respectively. PCR products were analyzed by electrophoresis using an agarose gel. Sizes of DNA markers are indicated in kilobases (kb).

Figure 14A:
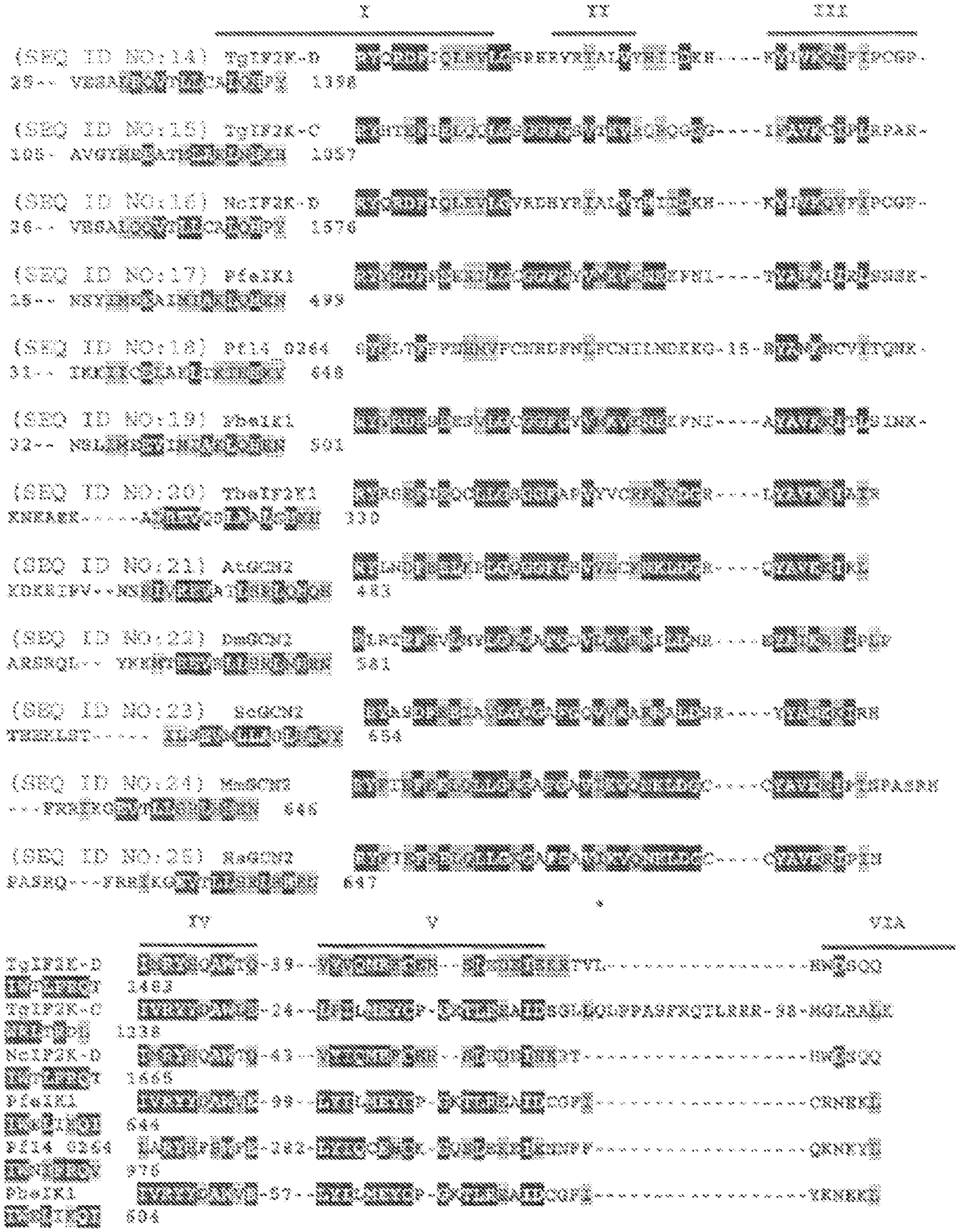
FIGS. 14A-C show the alignment of TgIF2K-D protein kinase domain with other eIF2α kinases.
Figure 14B:
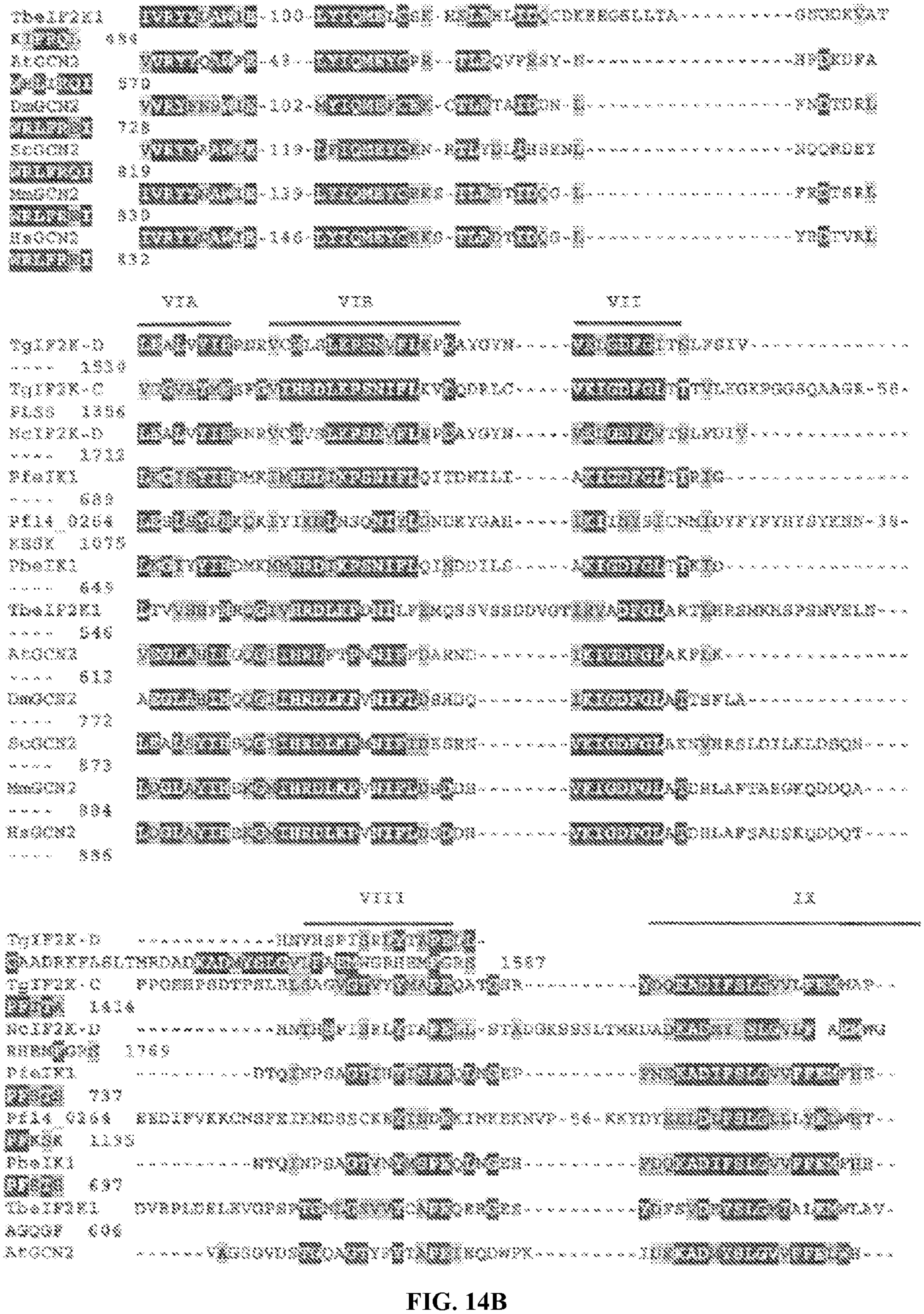
Figure 14C:
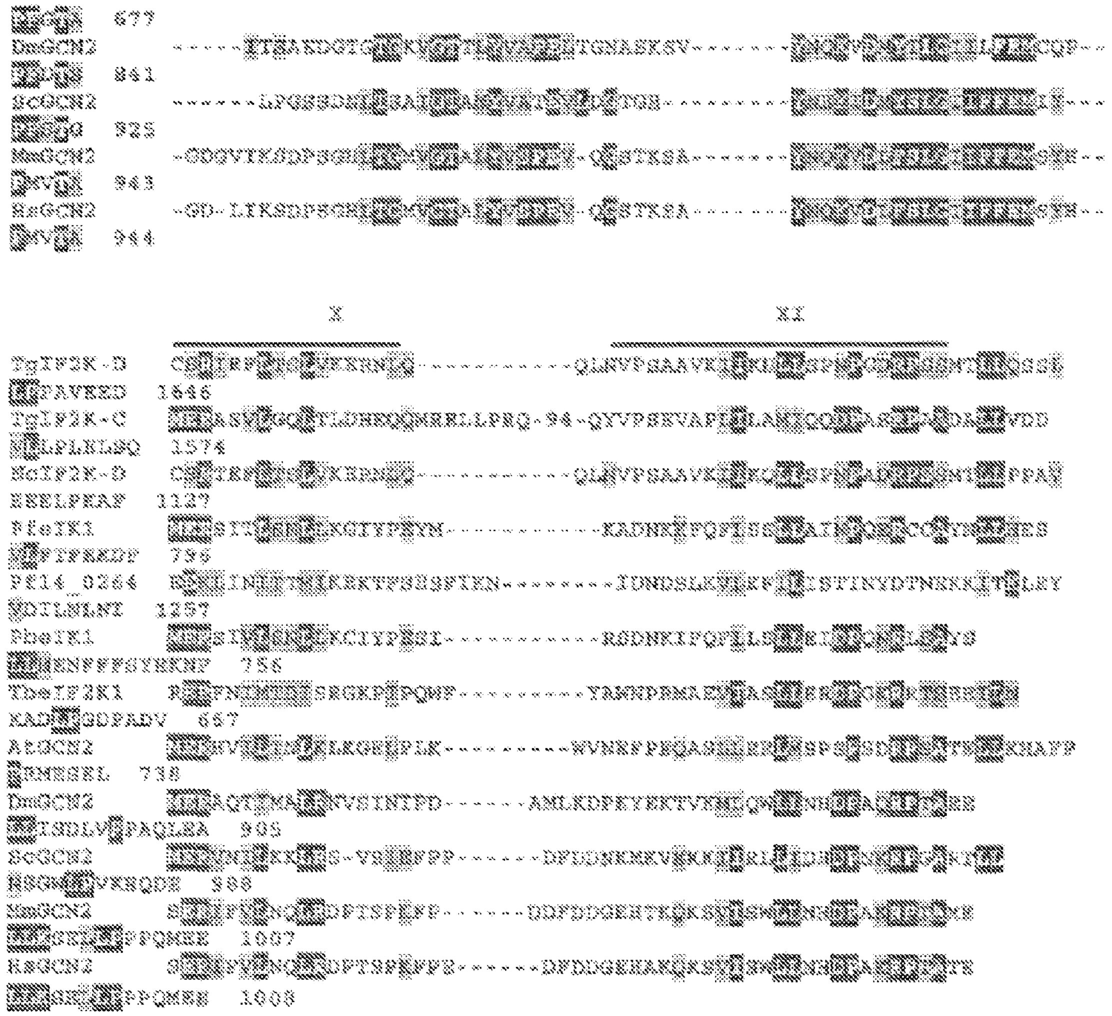

Referring now to FIG. 14, alignment of TgIF2K-D protein kinase domain with other eIF2α kinases. The TgIF2K-D protein kinase domain comprises 12 regions indicated by solid bars and roman numbers (I-XII), including an insert between motifs IV and V that is characteristic of eIF2α kinases. This insert, as well as other sequences that would create gaps in the alignment, were replaced by the number of omitted amino acid residues. Sequence identities shared among the eIF2α kinases are highlighted in black, while gray indicates residues with similar chemical properties. The invariant lysine residue located in the active site is marked by an asterisk. Numbers on the right indicate the residue position in the following GCN2-related sequences: Tg: *Toxoplasma gondii*, Nc: *Neospora caninum*, Pf: *Plasmodium falciparum*, Pb: *Plasmodium berghei*, Tb: *Trypanosoma brucei*, At: *Arabidopsis thaliana*, Dm: *Drosophila melanogaster*, Sc: *Saccharomyces cerevisiae*, Mm: *Mus musculus*, Hs: *Homo sapiens*. An alignment between TgIF2K-D and the eIF2α kinases from multiple species was compiled using BLAST and CLUSTALW. TgIF2K-D (residues 1,318 to 1,630) has the central features characteristic of eIF2α kinases, including an insert between subdomains IV and V (FIG. 1 and S3). As judged by BLAST analyses, this portion of TgIF2K-D is most closely related to putative eIF2α kinases from parasites *Plasmodium falciparum* (AAN37036; 4e-14) and *Trypanosoma brucei* (XP 828792.1; 6e-10) followed by characterized GCN2 orthologues from *Arabidopsis thaliana* (CAD30860; 6e-32); *Drosophila melanogaster* (AAC13490; 8e-27); *Schizosaccharomyces pombe* (AAU11313; 2e-25); and *Saccharomyces cerevisiae* (AAA34636; 1e-22). Another hallmark feature of GCN2 is an RWD domain, which is present between residues ~800 and ~1,000 of TgIF2K-D, with a significance of 4e-6 as determined by the motif search program Pfam. Finn, R. D., J. Mistry, J. Tate, P. Coggill, A. Heger, J. E. Pollington, O. L. Gavin, P. Gunasekaran, G. Ceric, K. Forslund, L. Holm, E. L. Sonnhammer, S. R. Eddy, and A. Bateman. 2010.

Referring now to FIG. 15, the TgIF2K-D RWD domain contains the YPXXXP motif, indicated by the solid bar, which is conserved among RWD domains of GCN2-related protein kinases. Sequence identities shared among these eIF2α kinases are highlighted in black, while gray indicates residues with similar chemical properties. Numbers on the right indicate the residue position in the following GCN2-related sequences: Tg: *Toxoplasma gondii*, Nc: *Neospora caninum*, Pf: *Plasmodium falciparum*, Dm: *Drosophila melanogaster*, Mm: *Mus musculus*, Sc: *Saccharomyces cerevisiae*. The Pfam protein families database. Nucleic acids research 38:D211-222. The RWD in Gcn2 from *S. cerevisiae* was reported to directly bind to the activator protein GCN1, and residue changes in Gcn2 that blocked this binding, or abolition of the Gcn2/Gcn1 association by Gcn1 binding with another RWD-containing protein Yih1, blocked Gcn2 phosphorylation of eIF2α in yeast depleted for amino acids. *Toxoplasma* also has a predicted GCN1 orthologue (TGME49_031480) and a Yih1-related protein (TGME49_112350), supporting the idea that this network functions to regulate a GCN2-related eIF2α kinase in this parasite.

The sequences of the histidyl-tRNA synthetase (HisRS) domain, which stimulates eIF2α kinase activity by binding to uncharged tRNAs accumulating during nutrient deprivation (13), appears to be less well conserved in the protozoan GCN2-like kinases. Analysis of the sequences flanking the C-terminal end of the protein kinase domain (residues 1,750-2,360) identified the PRGGRVY[2299] sequence as the closest match to the Histidine B sequence (AAGGRYD), which is characteristic for the HisRS-related domains. Sood, R., A. C. Porter, D. Olsen, D. R. Cavener, and R. C. Wek. 2000. *A mammalian homologue of GCN2 protein kinase important for translational control by phosphorylation of eukaryotic initiation factor-2a. Genetics* 154:787-801. This weaker conservation of the HisRS-related sequences is a feature shared with other GCN2-related protein kinases from apicomplexans, including *P. falciparum*. TgIF2K-D also lacks the pseudokinase domain found in mammalian and yeast GCN2s, which is thought to contribute to the eIF2α kinase activity. The C-terminus of Gcn2 is important for dimerization and ribosome association and this region in TgIF2K-D (residues 2,436-2,499) is rich in hydrophobic and basic residues, which are suggested to contribute to these regulatory processes in this eIF2α kinase.

Figure 6:
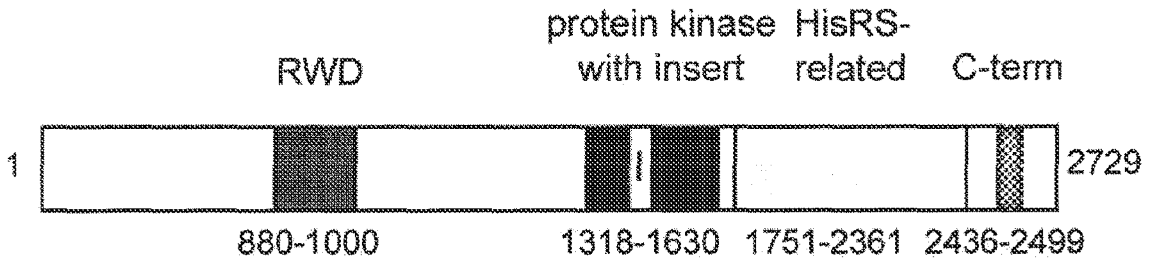
FIG. 6. The domain structure of TgIF2K-D.

Referring now to FIG. 16, alignment of the C-terminal homology region of TgIF2K-D with other predicted GCN2-like protein kinases from parasites. Sequence identities shared among the C-terminal homology regions of the GCN2-like protein kinases are highlighted in black. Gray highlights indicate residues with similar chemical properties. Numbers on the right indicate the residue position in the following GCN2-related sequences: Tg: *Toxoplasma gondii*, Nc: *Neospora caninum*, Pf: *Plasmodium falciparum*, Pb: *Plasmodium berghei*, PkH: *Plasmodium knowlesi* and Pvx: *Plasmodium vivax*. Numbers listed on the left of the sequences indicate the GeneID from the corresponding databases. Interestingly, this region shares sequence identity with GCN2-like kinases encoded in apicomplexans *Neospora caninum* (NCLIV_010550, 3e-30), *Cryptosporidium muris* (CMU_027700; 0.011), *Plasmodium falciparum* (PF14 0264; 9e-08), *Plasmodium berghei* (PBANKA_101620, 4.8e-08), *Plasmodium knowlesi* (PKH_113740, 1.1e-07)

and *Plasmodium vivax* (PVX_085120; 2e-07) Designated herein as the conserved region as the C-terminal homology (CTH) region (FIG. 6).

Referring now to FIG. 6, TgIF2K-D contains a protein kinase domain (black boxes) with an insert (I) characteristic of eIF2α kinases, and signature regulatory regions including the RWD domain (dark gray) and a proposed HisRS-related region (light gray). The conserved C-terminal homology (CTH) domain is denoted with a mottled box. The numbers below the diagram demarcate the amino acid residues for each of the domains of TgIF2K-D. Based on the presence of sequences related to the eIF2 kinases juxtaposed to the signature RWD domain, a putative Histidine B-like sequence, and a C-terminus rich in hydrophobic and basic residues, the TgIF2K-D is suggested to be a parasite orthologue of GCN2.

TgIF2K-D is Expressed in Intra- and Extracellular Parasites

Figure 7A:
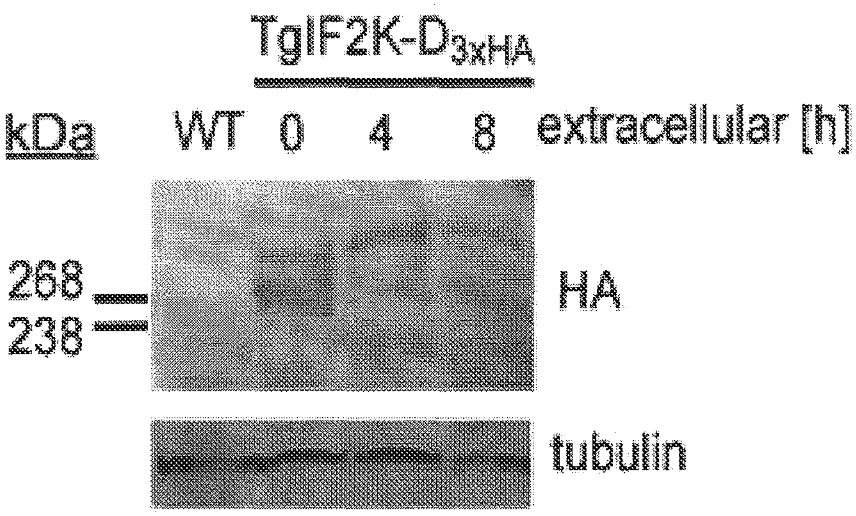
FIG. 7A. TgIF2K-$D_{3\times HA}$ protein was detected by western blotting by probing parasite lysates with anti-HA antibody.
Figure 7B:
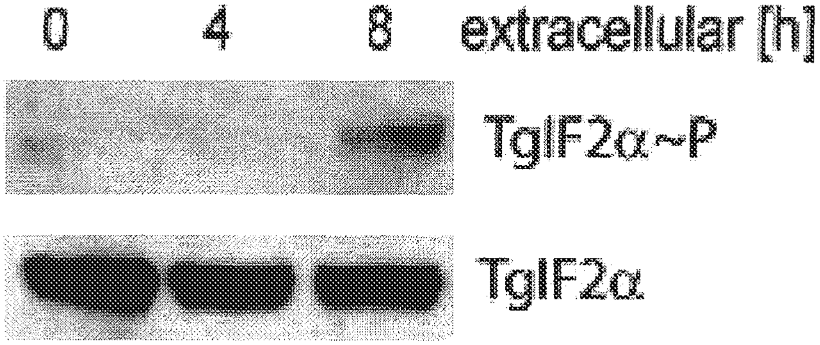
FIG. 7B. Western blot of TgIF2K-$D_{3\times HA}$ parasites with antibodies specific for total TgIF2α or phosphorylated TgIF2α (TgIF2α~P) during 0, 4, or 8 hours extracellular stress.

Using RHΔKu80 parasites engineered to have greater frequencies of homologous recombination TgIF2K-D was tagged with three HA epitopes (3×HA) at the C-terminus. Immunoblot analyses of total protein lysate using anti-HA antibody identified three clustered protein bands with a molecular weight similar to the deduced 289 kDa for TgIF2K-D (FIG. 7A). These proteins were not present in parental parasites referred to as wild-type, WT. Referring now to FIG. 7A, the faster migrating TgIF2K-$D_{3\times HA}$ variants diminished when parasites were subjected to extracellular stress for 4 or 8 hours. Samples were normalized in the immunoblot analysis using antibody specific for *Toxoplasma* tubulin. Referring now to FIGS. 7A and 7B, it was also observed that upon extracellular incubation for up to 8 hours, a condition that induces high levels of TgIF2α phosphorylation the levels of the faster migrating TgIF2K-$D_{3\times HA}$ variants diminished while the slower migrating protein increased. The difference between these variants of TgIF2K-D may be attributable to post-translational modification(s), such as protein phosphorylation, or alternative mRNA splicing, which may contribute to TgIF2K-D activation by stress. While an alternative mRNA splice products were not detected during this analysis of the TgIF2K-D cDNAs, alternative mRNA splicing was reported in earlier studies of mammalian GCN2, although their biological significance has not been confirmed.

Figure 7C:
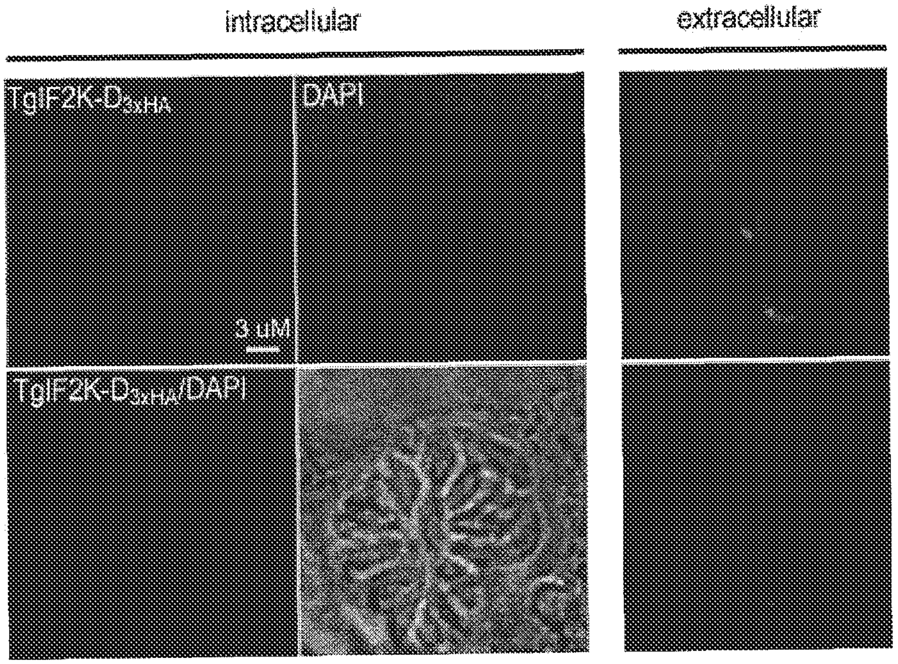
FIG. 7C. Immunofluorescence analysis using a rat monoclonal HA-antibody and an anti-rat Alexa488 conjugate (green) was performed to show localization of TgIF2K-$D_{3\times HA}$ protein in intra- and extracellular parasites.

Referring now to FIG. 7C, nuclear DNA was co-stained with 4,6-diamidino-2-phenylindole (DAPI, blue). TgIF2K-$D_{3\times HA}$ does not colocalize with nuclear DNA, indicating a cytoplasmic localization in the parasite. In order to identify the cellular location of TgIF2K-D, immunofluorescence microscopy was also carried out. The HA-tagged TgIF2K-D localized to the parasite cytosol in both intra- and extracellular parasites. A cytosolic localization is consistent with reports on GCN2 in other species. Wek, R. C., 2006.

Figure 17:
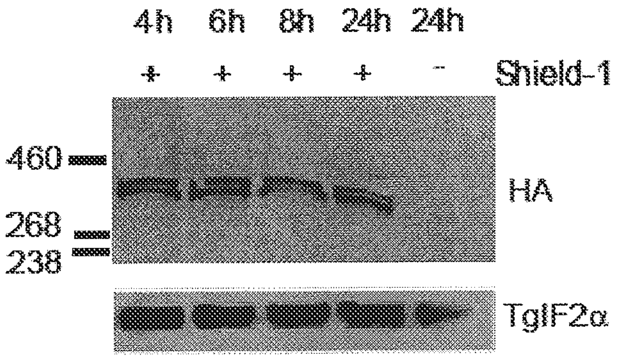
FIG. 17. SDS-PAGE and normalized for western blotting using a monoclonal anti-HA antibody.

TgIF2K-D Facilitates TgIF2α Phosphorylation and Translational Control in Extracellular Parasites Generation of a conditional TgIF2K-D knockdown. Extracellular stress is a potent inducer of TgIF2α phosphorylation and loss of translational control in the TgIF2α-S71A mutant reduced parasite viability. Joyce, B. R., 2010. In order to address whether TgIF2K-D is required to manage extracellular stress, knockdown and knockout parasite clones were generated in the RHΔKu80 background. Referring now to FIG. 17, a genetic fusion of a destabilization domain (DD) causes degradation of endogenously expressed TgIF2K-D. Cell culture medium was supplemented with 500 nM Shield-1 for up to 24 hours to stabilize TgIF2K-$D_{2\times DD}$. Vehicle was used a negative control. Equal amounts of protein lysate were resolved via SDS-PAGE and normalized for western blotting using a monoclonal anti-HA antibody. Levels of TgIF2α protein were probed as a loading control. The knockdown of TgIF2K-D involved an in frame-fusion of two HA tags and a 12 kDa destabilization domain (DD) at the C-terminus of the endogenous TgIF2K-D in the RHΔKu80 strain (Fig. S6). The parasite clone, designated TgIF2K-$D_{2\times DD}$, allowed tunable expression of the TgIF2K-D protein. In the absence of the stabilizing ligand Shield-1, DD-tagged proteins are rapidly degraded. TgIF2K-$D_{2\times DD}$ parasites cultured without Shield-1 had no detectable levels of TgIF2K-D protein as assayed by western blot analysis.

Figure 8A:
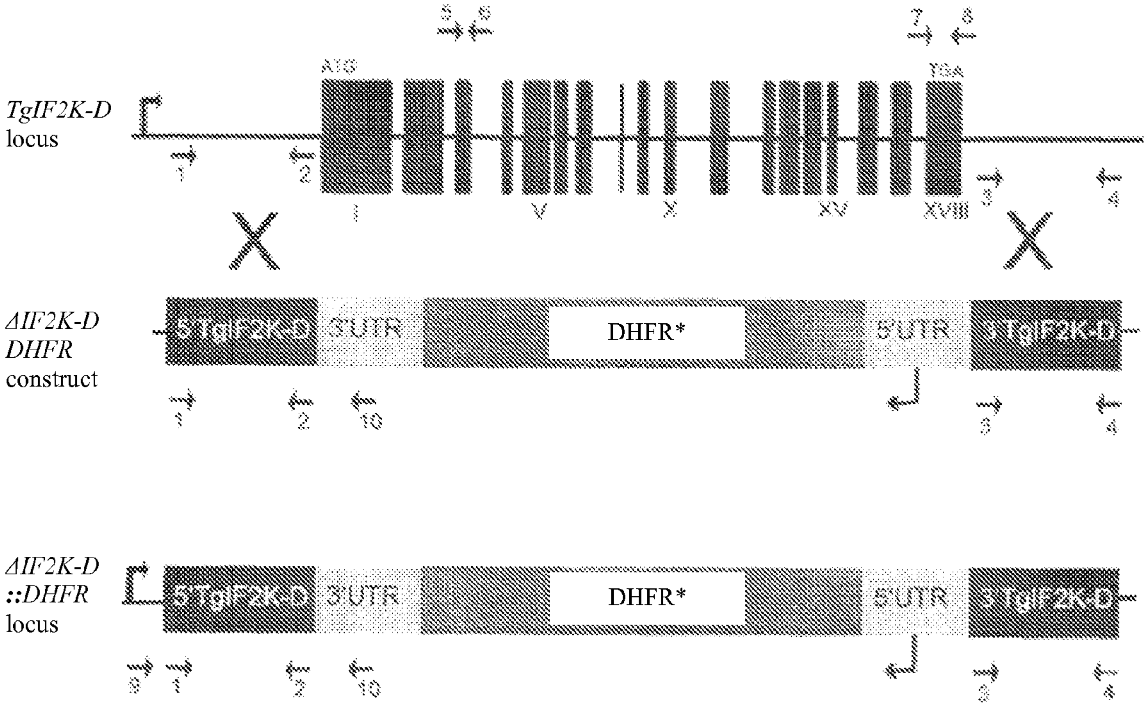
FIG. 8A. The TgIF2K-D genomic locus, depicted with 18 exons, was replaced by a minigene conferring resistance to pyrimethamine (DHFR*) using homologous recombination in ΔKu80 RH strain parasites.
Figure 8B:
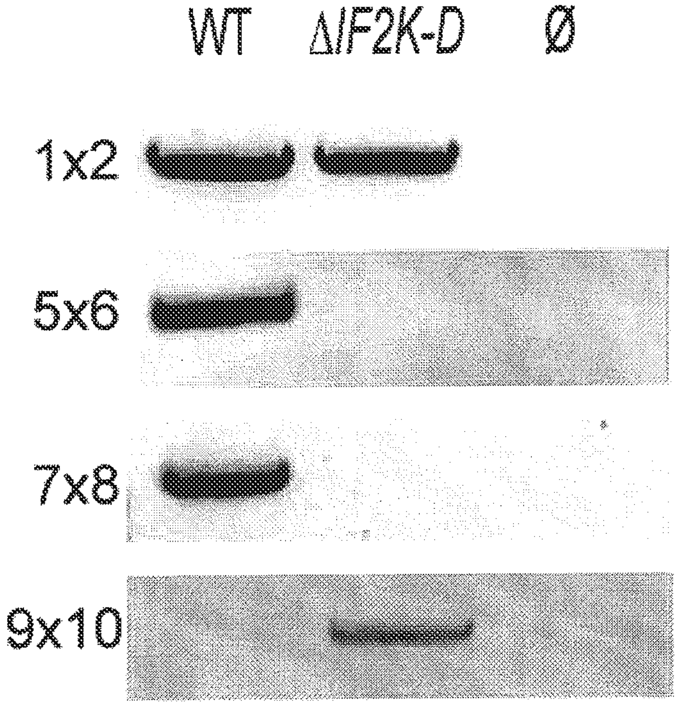
FIG. 8B. Genomic PCR assays used gDNA harvested from WT or ΔIF2K-D parasites and the indicated primers to validate replacement of the TgIF2K-D genomic locus.

Referring now to FIG. 8A, the numbered arrows indicate the positions of primers used to screen genomic DNA from transfected pyrimethamine-resistance clones and parental (WT) parasites. Primer sequences are listed in the 2. The knockout of TgIF2K-D eliminated the entire genomic locus through homologous recombination and allelic replacement with a modified DHFR-TS minigene, which confers resistance to pyrimethamine (FIG. 8A). The ΔIF2K-D was verified by PCR analyses of genomic DNA purified from pyrimethamine-resistant clones (FIG. 8B). In addition, total RNA from the parental strain and a ΔIF2K-D knockout clone was isolated for RT-PCR analysis of the TgIF2K-D transcript. This parasite clone represents the first knockout of an eIF2α kinase in *Toxoplasma*.

Figure 8C:
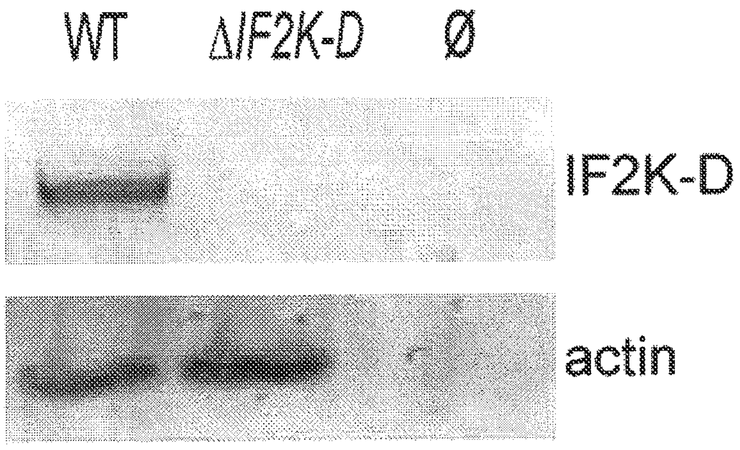
FIG. 8C. The absence of TgIF2K-D mRNA in the ΔIF2K-D parasites was confirmed by RT-PCR.

Referring now to FIG. 8C, the absence of TgIF2K-D mRNA in the ΔIF2K-D parasites was confirmed by RT-PCR analysis using primers upstream and downstream of the encoded protein kinase domain (primer #11 and #12). *Toxoplasma* actin mRNA was amplified as a positive control (primers #13 and #14). A no-template control (∅) was included in all PCRs. While TgIF2K-D mRNA was amplified from parental parasites, the corresponding transcript was not detected in ΔIF2K-D parasites.

| Oligonucleotide | # | 5'-3' sequence |
|---|---|---|
| (SEQ ID NO: 39) | 1 | GAAATAGCGGCCGCGTCACTGACCAATGAGCTTTGG |
| (SEQ ID NO: 40) | 2 | GAACAAACTAGTAGAACGAAGGGAGGAGAGTTCG |
| (SEQ ID NO: 41) | 3 | GTTCAAAAGCTTTGGAAGAGACCGACGCTGAACG |
| (SEQ ID NO: 42) | 4 | GTAGTTGGGCCCGCTTCGTTGAGTGATGTGAGACG |
| (SEQ ID NO: 43) | 5 | CTTCAGCAATTTGTGGGAGGAAATGC |
| (SEQ ID NO: 44) | 6 | GAGCGGCTCGTCGCTCGTCGTTGAGG |
| (SEQ ID NO: 45) | 7 | TCCTCCACTTCCAATTTTAGCGCGTCGGTCTCTTCCACCTCTGCCTGG |
| (SEQ ID NQ: 46) | 8 | TACTTCCAATCCAATTTAATGCATGTTCCGTAGGCGGTGATCCCTCGTGG |

-continued

| | | |
|---|---|---|
| (SEQ ID NO: 47) | 9 | CCACAGTTTCGTTGCTCTCTTGG |
| (SEQ ID NO: 48) | 10 | CTGTATGCCGCTAGAGTGCTGG |
| (SEQ ID NO: 49) | 11 | GAAACGGGATCCGCGAAGAAACAGAGCGACAGCGGTGCTGG |
| (SEQ ID NO: 50) | 12 | GCAGAGTCTAGATCACGCGGGAGAGTCAGAAGTACATTTCTGTGG |
| (SEQ ID NO: 51) | 13 | ACGTATGATGCGCGAGAAAA |
| (SEQ ID NO: 52) | 14 | GGGCGTTTCATGACCTAAA |
| (SEQ ID NO: 53) | 15 | GCTTAACGGGTACGGCGTTT |
| (SEQ ID NO: 54) | 16 | GCGGTTAATCCAGCGTATGC |
| (SEQ ID NO: 55) | 17 | CAGGGCCGTACGAGAACGT |
| (SEQ ID NO: 56) | 18 | GCCCACGACAGCAGACAACT |
| (SEQ ID NO: 57) | 19 | CACTCGGTTCGTGTGCTTTCT |
| (SEQ ID NO: 58) | 20 | CCGTCACGCCACTACAACAG |
| (SEQ ID NO: 59) | 21 | CTCTGCATGCAGCTGGTCGTTGG |
| (SEQ ID NO: 60) | 21N | GCAGCCGATTGATTTCATCGGATGG |
| (SEQ ID NO: 61) | 22 | CACCGTGTCAGCTGCCTCCAAGG |
| (SEQ ID NO: 62) | 22N | CTTTCTGTCTGTCCTCGCTGACTGG |
| (SEQ ID NO: 63) | 23 | CCACCAGTGTCCAAGATCCATCG |
| (SEQ ID NO: 64) | 23N | GATCCATCGTCTCCGTCCTCTTCG |
| (SEQ ID NO: 65) | 24 | CACTCGGTTCGTGTGCTTTCT |
| (SEQ ID NO: 66) | 25 | CCGTGACGCCACTACAACAG |
| (SEQ ID NO: 67) | 26 | GCTTAACGGGTACGGCGTTT |
| (SEQ ID NO: 68) | 27 | GCGGTTAATCCAGCGTATGC |
| (SEQ ID NO: 69) | 28 | CAGGGCCGTACGAGAACGT |
| (SEQ ID NO: 70) | 29 | GCCCACGACAGCAGACAACT |

Figure 9A:
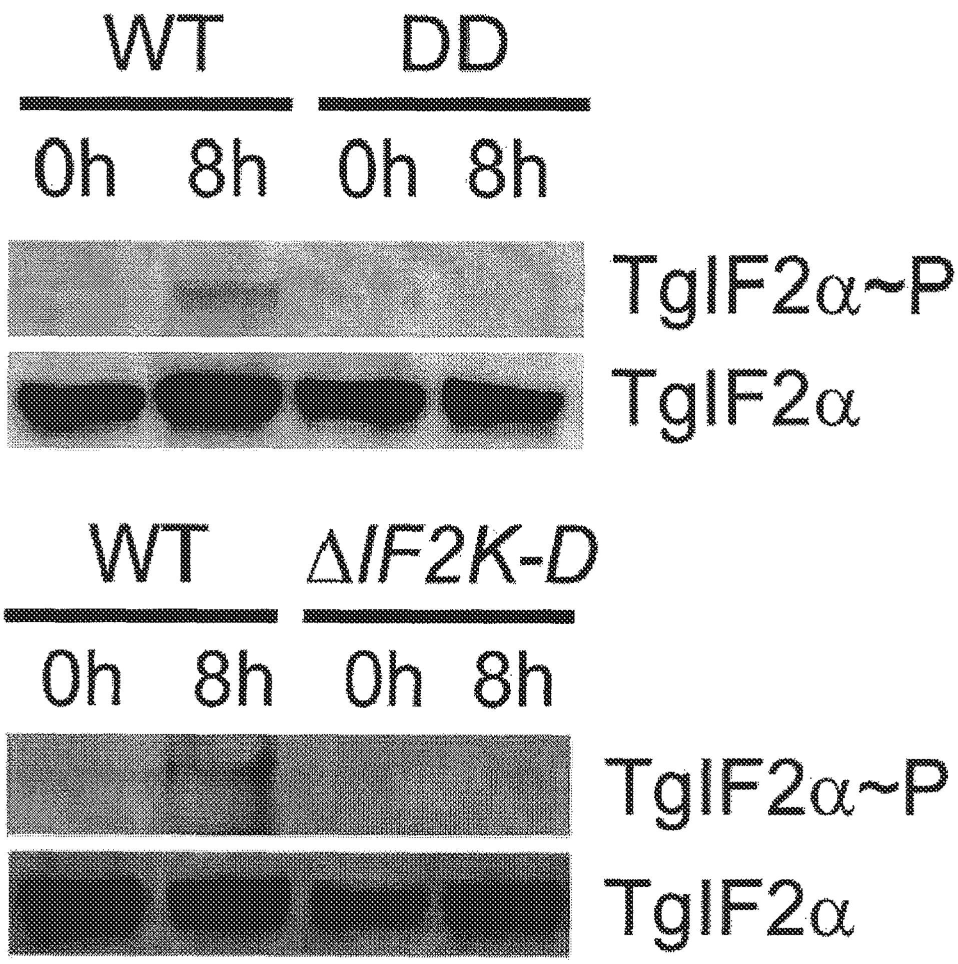
FIG. 9A. Wild-type (WT), TgIF2K-$D_{2\times DD}$ (DD), and ΔIF2K-D parasites were exposed for 0 or 8 hours (h) to the extracellular environment.
Figure 9B:
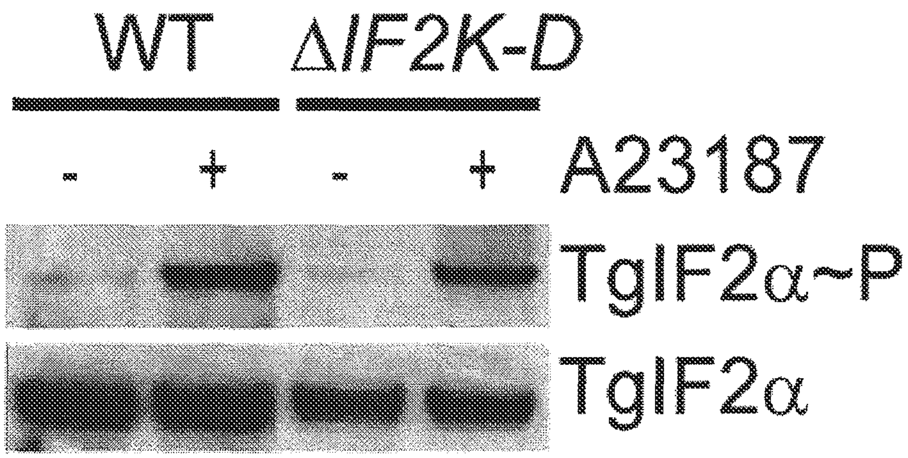
FIG. 9B. WT and ΔIF2K-D tachyzoites were treated with 5 μM calcium ionophore A23187 for 30 minutes and then analyzed for TgIF2α~P by immunoblotting.

Next addressed was whether TgIF2K-D is required for induced TgIF2α phosphorylation when the parasite is outside of the host cell. Referring now to FIG. 9A, TgIF2α phosphorylation was analyzed by separating cell lysates via denaturing SDS-PAGE, followed by western blotting using antibodies to total TgIF2α or phosphorylated TgIF2α (TgIF2α~P). Parental WT parasites showed robust TgIF2α phosphorylation after 8 hours of incubation in the extracellular environment. By comparison, there was minimal TgIF2α phosphorylation in the TgIF2K-$D_{2\times DD}$ knockdown or ΔIF2K-D knockout parasites following extracellular exposure. In order to test the specificity of TgIF2K-D in responding to extracellular stress, WT and ΔIF2K-D parasites were exposed to the calcium ionophore A23187, a known inducer of ER stress and TgIF2α phosphorylation. As shown in FIG. 9B, the ΔIF2K-D parasites were not defective for TgIF2α phosphorylation in response to ER stress. These results support the model that each TgIF2α kinase in *Toxoplasma* recognizes distinct stress arrangements, and TgIF2K-D is central for inducing TgIF2α phosphorylation when parasites are outside the host cell.

Figure 9C:
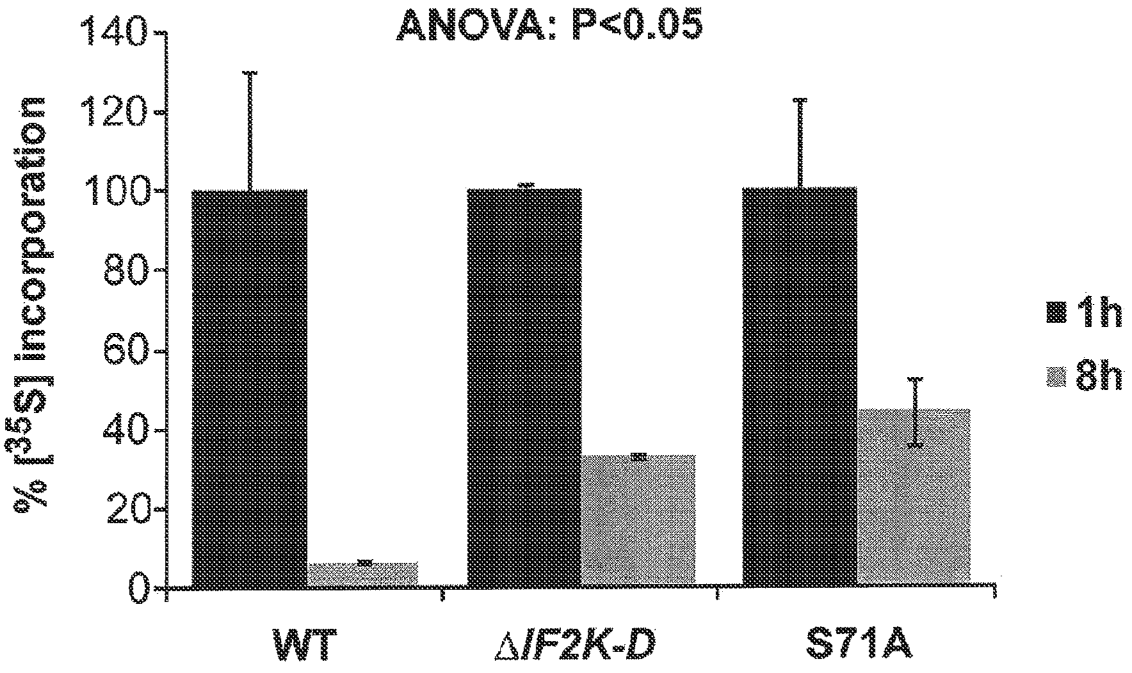
FIG. 9C. WT, TgIF2α-S71A and ΔIF2K-D were physically released from host cells and incubated for 1 or 8 h in DMEM culture medium.

Under stress conditions, eIF2α phosphorylation represses general translation as part of the cellular stress response. In order to compare translational control in WT versus ΔKF2K-D parasites, the incorporation of radiolabeled Cys/Met in parasites subjected to extracellular stress for 1 and 8 hours was measured. Referring now to FIG. 9C, one hour prior to harvesting, the parasites were incubated in the presence of [$^{35}$S]-Cys/Met. Lysates were prepared and equal amounts of protein were precipitated with TCA. Levels of incorporation of radiolabeled amino acids were determined via scintillation counting. Three experiments were performed and incorporation of the radiolabel is represented as a percentage of that measured for parasites subject to 1 h of stress. Error bars indicate the standard error and significance indicates $p<0.05$. Protein synthesis was repressed by greater than 90% in WT parasites subjected to 8 hours of extracellular stress; however, in the ΔIF2K-D and TgIF2α-S71A mutant parasites, protein synthesis was only diminished by about 40%. These data strongly suggest that TgIF2K-D is the primary eIF2α kinase that mediates translational control in response to extracellular stress.

Parasites Lacking TgIF2K-D Exhibit a Fitness Defect

TgIF2α-S71A mutants are outcompeted by wild-type parasites when placed in a "head-to-head" competition assay, as the mutant struggles to cope with the extracellular environment experienced while finding a new host cell. Given that ΔIF2K-D failed to phosphorylate TgIF2α in response to extracellular stress (FIG. 9A), ΔIF2K-D parasites were tested to determine if they too would be outcompeted by parental wild-type parasites using the head-to-head fitness assay.

Figure 10A:
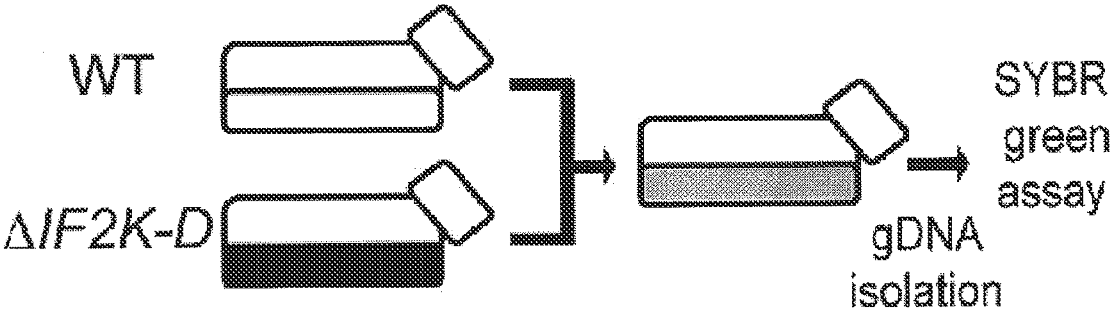
FIG. 10A. TgIF2K-D contributes to the fitness of *Toxoplasma* tachyzoites Schematic of the "head-to-head" fitness assay.
Figure 10B:
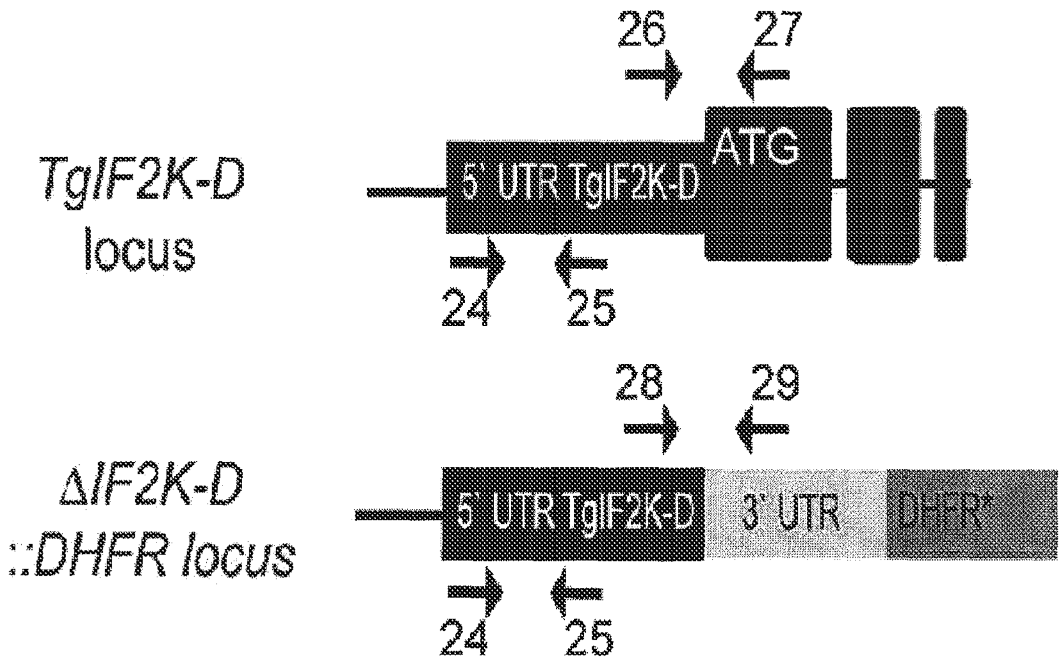
FIG. 10B. Map of primers (arrows) used to distinguish between wild-type (WT) and ΔIF2K-D parasites.
Figure 10C:
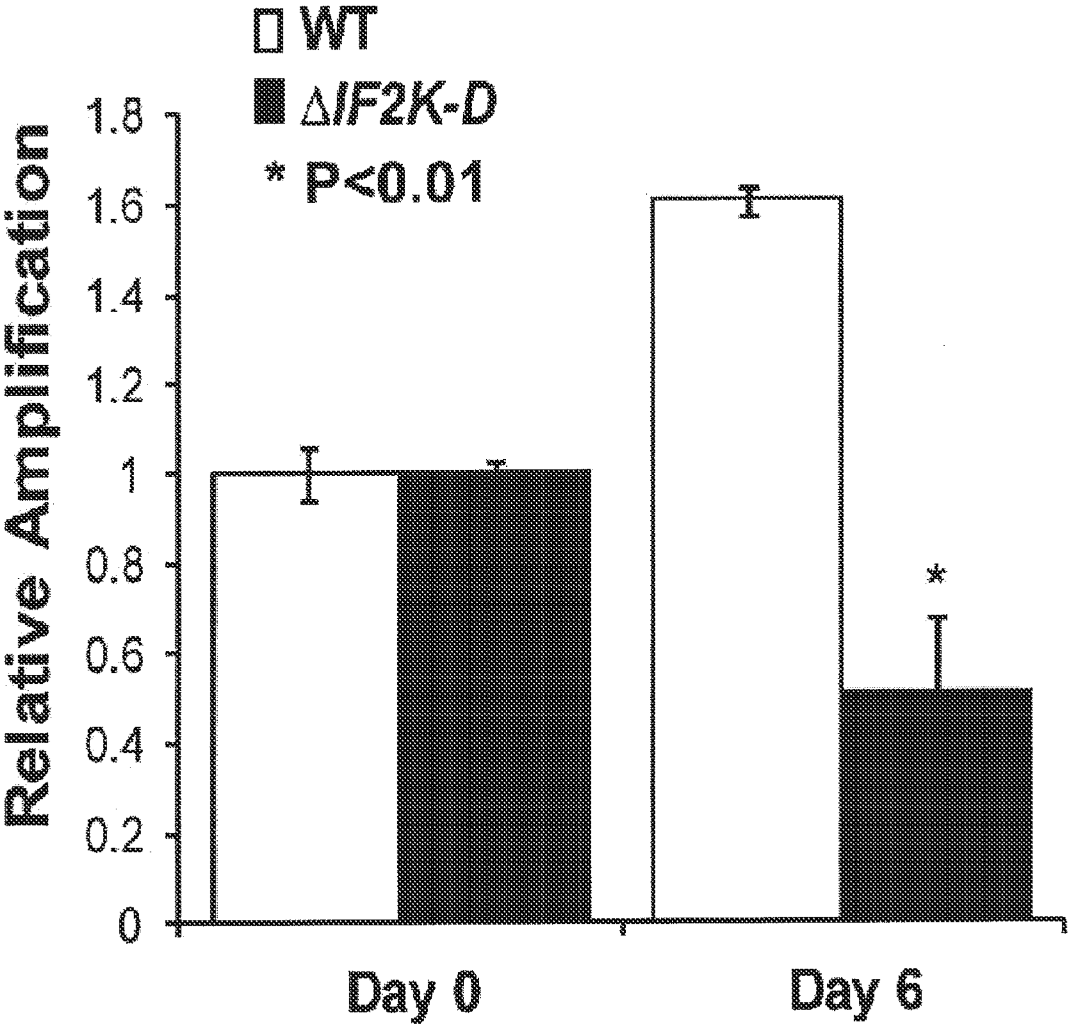
FIG. 10C is a bar graph showing parasites lacking TgIF2K-D exhibit reduced fitness in the parasite lytic cycle.

Equal numbers of WT and ΔIF2K-D parasites were premixed and transferred into the same culture flask containing a confluent monolayer of HFF cells (FIG. 10A). Samples were taken prior to infection and after day 6 for genomic DNA isolation. The relative amount of WT and ΔIF2K-D parasites was determined using a SYBR Green-based quantitative PCR assay and primers specific for WT or ΔIF2K-D parasites. Referring now to FIG. 10B, relative levels of WT and ΔIF2K-D parasites were determined using a SYBR green assay with primers #26 and #27, or #28 and #29, as indicated. Samples were normalized for the amplification of a DNA fragment encoding the 5'-UTR, which is conserved between WT and ΔIF2K-D (primers #24 and #25). Error bars indicate standard error and significance was determined using two-tailed Student's t-test, with $p<0.01$, as indicated by the asterisk. Primers that amplify DNA from both strains were used to ensure normalization between the samples. WT parasites outgrew the mutant parasites by day 6 (FIG. 10C), establishing that parasites lacking TgIF2K-D exhibit reduced fitness in the parasite lytic cycle.

TgIF2K-D Promotes the Viability of Extracellular Tachyzoites

Figure 11A:
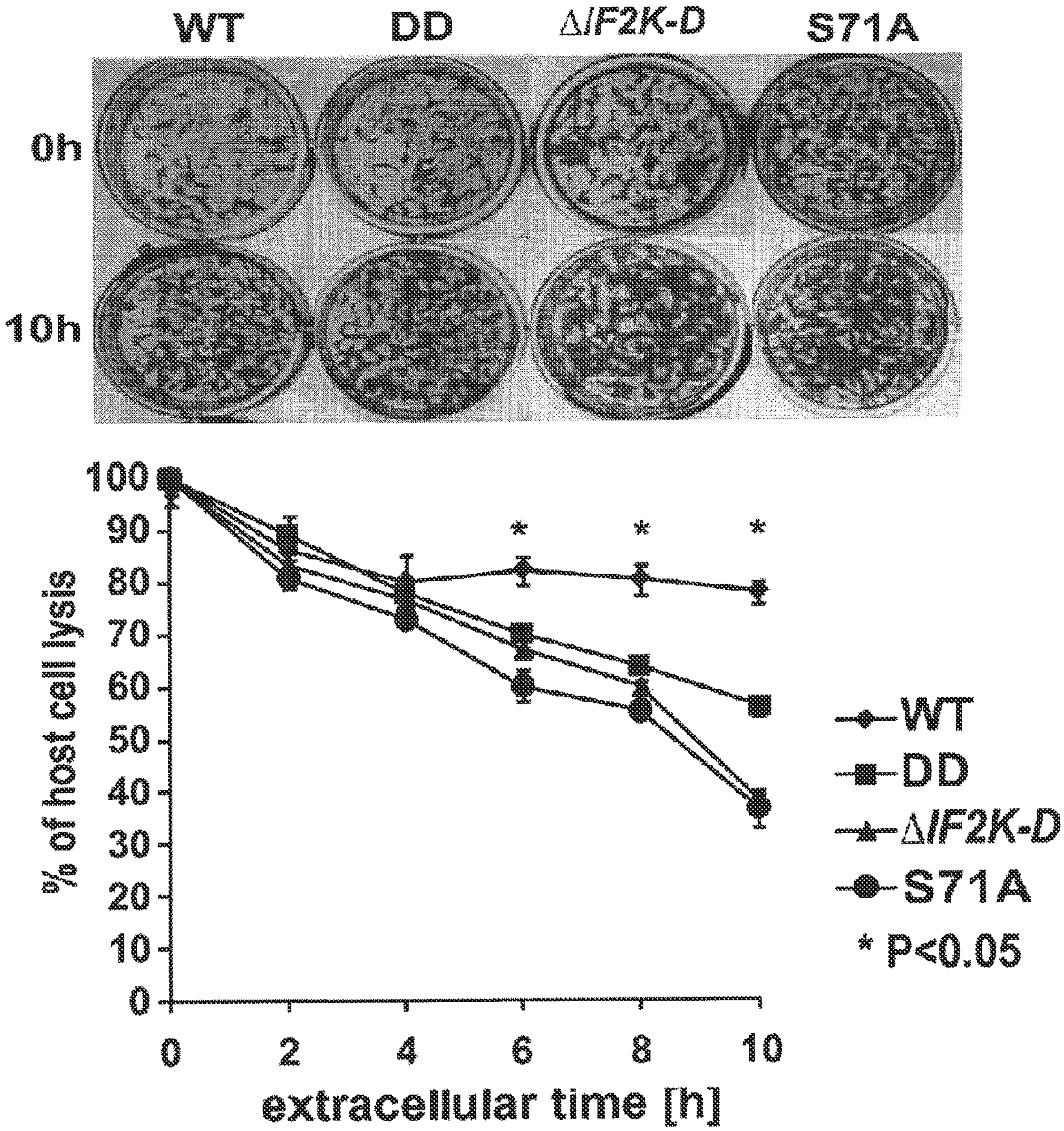
FIG. 11A. 500 wild-type (WT), TgIF2K-$D_{2\times DD}$ (DD), ΔIF2K-D, or TgIF2α-S71A (S71A) parasites physically released from host cells were incubated extracellularly in DMEM culture medium for the designated times before being allowed to infect HFF monolayers in 12-well plates.

These data suggest that parasites deficient for TgIF2K-D suffer a loss in viability due to an inability to respond appropriately to the extracellular stress experienced while outside host cells. To further address the role of TgIF2K-D in the extracellular stress response, WT and the different mutant parasites (TgIF2α-S71A, ΔIF2K-D, and TgIF2K-$D_{2\times DD}$ without Shield) were incubated outside of host cells in DMEM between 0 and 10 hours prior to applying them to a fresh host cell monolayer. After 7 days, the infected host cells were fixed and stained to determine the degree of host cell lysis. With increased periods of extracellular stress, ΔIF2K-D parasites showed sharply reduced infection and lysis of host cells that was similar to that measured for the TgIF2α-S71A mutants (FIG. 11A). This defect was more pronounced in the ΔIF2K-D parasites compared to the TgIF2K-$D_{2\times DD}$ knockdown, suggesting that there are residual levels of functional TgIF2K-D despite the absence of Shield.

Figure 11B:
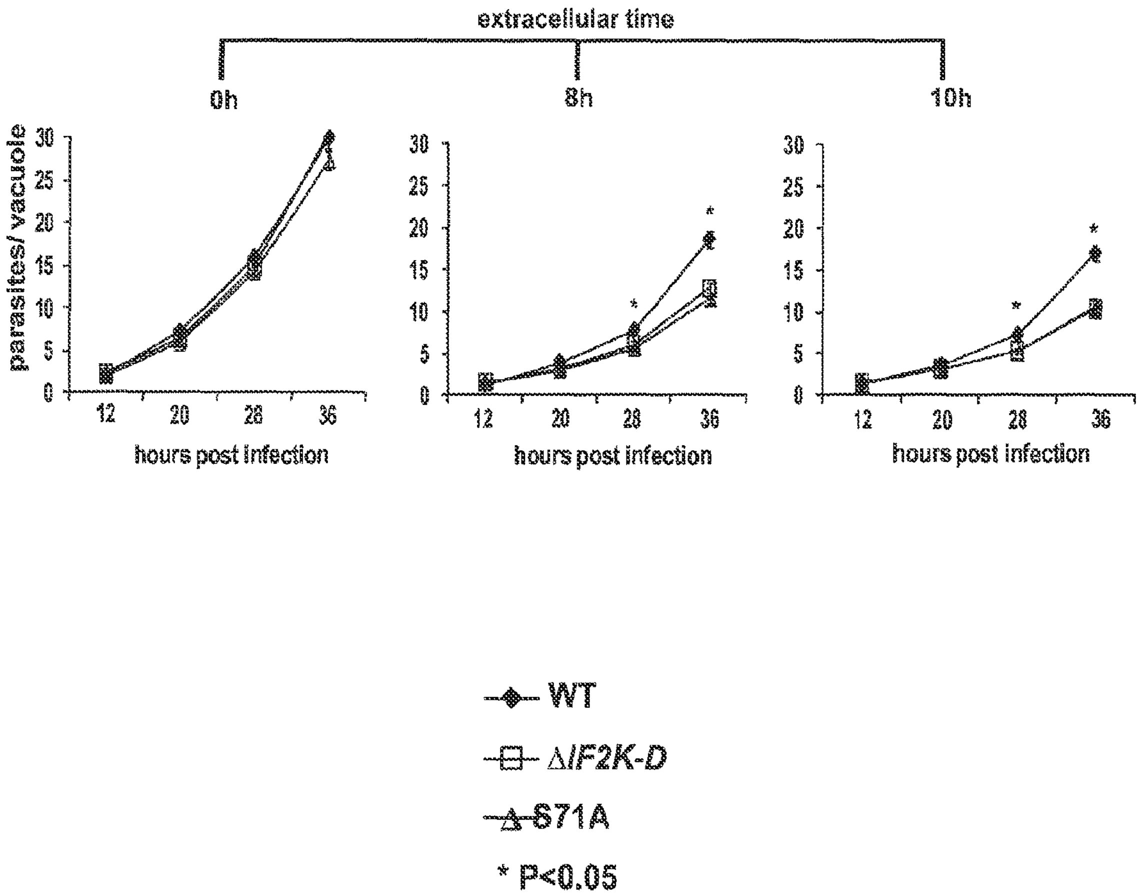
FIG. 11B provides graphs showing parasites/vacuole at hours post infection.

In order to further characterize the role of translational control in the resistance to extracellular stress the doubling rate of the ΔIF2K-D parasites was also measured. ΔIF2K-D parasites proliferated at a similar rate relative to WT when allowed to infect a new host cell monolayer immediately upon release from their initial host cells (FIG. 11B, 0 hr. extracellular stress). Still referring to FIG. 11B, consistent with the plaque assay, extracellular stress led to a significant reduction in the proliferation of ΔIF2K-D parasites. WT parasites subjected to extracellular stress for 10 hours grew to an average of ~17 parasites/vacuole, but ΔIF2K-D parasites only to ~10 parasites/vacuole. This reduction in doubling time was also observed when the TgIF2α-S71A mutants were subjected to extracellular stress prior to infection of the HFF cells. Collectively, these studies establish that TgIF2K-D is critical for promoting survival of extracellular tachyzoites through translational control mediated by the phosphorylation of TgIF2α.

Eukaryotic cells have evolved mechanisms to tolerate stresses encountered in their environments. A well characterized stress response pathway conserved from yeast to humans centers on the phosphorylation of eIF2α, which reduces translation initiation and provides the cell with time to reprogram its genome in order to address the new challenges caused by a change in conditions. This stress response has been found to be conserved in early-branching protozoa, including parasitic species such as the Apicomplexa and kinetoplastids (Mohrle et al., 1997; Moraes et al., 2007; Sullivan Jr. et al., 2004b).

As described herein, one function for eIF2α phosphorylation in the obligate intracellular protozoan, *Toxoplasma*, centers on the ability of the parasite to survive without the resources and shelter supplied by its host cell. Upon egress tachyzoites have evolved mechanisms to help them to survive in the extracellular environment long enough for them to invade a new host cell. This study shows that without eIF2α phosphorylation, tachyzoites have a diminished capacity to remain virulent when they are deprived of host cells. The decrease in virulence as a result of not being able to phosphorylate eIF2α is also seen when the mutant parasites are used in the mouse model of acute toxoplasmosis. These findings indicate that intracellular parasites are stressed when deprived of host cells, and that a key part of managing this "extracellular stress" involves translation control mediated by the phosphorylation of eIF2α.

There are four eIF2 kinases encoded in the *Toxoplasma* genome, designated TgIF2K-A through D. TgIF2K-A possesses a transmembrane domain and was found to be localized to the parasite ER (Narasimhan et al., 2008b). Upon treatment with ER stress agents, TgIF2K-A is released from its association with BiP, suggesting shared activation mechanisms with those described in yeast and mammals (Schroder and Kaufman, 2005a). TgIF2K-B is a cytosolic eIF2 kinase lacking homology to previously characterized eIF2 kinases (Narasimhan et al., 2008b). TgIF2K-C and -D are less well characterized, but resemble GCN2, an eIF2 kinase that is documented to respond to nutrient deficiency. The nature of the extracellular stress could be the absence of the host cell protecting or buffering the parasite from deficiencies in nutrients or metabolites, and/or a whole range of damaging environmental insults that confront the parasite when it is not in a host cell.

In other species, the phosphorylation of eIF2α causes a general depression in global protein synthesis, but a subset of mRNAs encoding master regulator transcription factors (such as yeast GCN4 or mammalian ATF4) are preferentially translated. Apicomplexa lack most conventional transcription factors conserved from yeast to mammals, but possess an expanded lineage of plant-like transcription factors with APETELA-2 domains, or ApiAP2 (Balaji et al., 2005). Whether ApiAP2 mRNAs are preferentially translated is not yet known, but the existence of DNA-binding transcription factors in *Toxoplasma* makes it likely that these primitive eukaryotes adhere to a similar stress response paradigm. Identification of the genes preferentially translated may provide more information explaining how TgIF2α phosphorylation enables parasites to survive while locating a new host cell.

In addition to the rapid proliferation of tachyzoites, pathogenesis of *Toxoplasma* also involves the ability of the tachyzoites to differentiate into bradyzoites. Bradyzoites form a tissue cyst that can remain in the host organism for life. During immunosuppressive conditions, the bradyzoites can reemerge as an acute tachyzoite infection. Consistent with their quiescent nature, latent bradyzoites maintain TgIF2α in its phosphorylated state, and it was suggested that this stress response may also function to lower protein synthesis in the dormant parasitic cyst (Narasimhan et al., 2008b). The TgIF2α-S71A mutant was created in the hypervirulent RH type I strain of *Toxoplasma*; a strain that is well suited for studies the proliferate stage of the parasite, this strain has largely lost its ability to develop into bradyzoites in vitro and in vivo (Khan et al., 2009). In order to further examine the role of TgIF2α phosphorylation in bradyzoites, it will be useful to generate the TgIF2α-S71A mutant in type II strain *Toxoplasma*. While type II strains grow more slowly and are less genetically amenable than type I strains there is every reason to believe that what is now known about TgIF2α phosphorylation in type I strains will be broadly applicable to type II strains of the parasite.

In addition to previous observations that phosphorylated TgIF2α accumulates in latent bradyzoites, data presented herein demonstrates that TgIF2α phosphorylation is also important during the tachyzoite lytic cycle, specifically during the critical time when the parasite is without a host cell. Therefore, pharmacological targeting of the TgIF2α stress response pathway promises to have multiple benefits in treating or perhaps preventing both acute and chronic forms of toxoplasmosis. It would be of great interest to assess if eIF2 phosphorylation and translation control also contribute to the survival of other intracellular pathogens during the times in their life cycle when they are outside of host cells.

The TgIF2K-D knockout showed reduced TgIF2α phosphorylation and translational control in response to extracellular stress, along with reduced viability when outside the host cell (FIGS. 9 and 11). This phenotype was also observed for the TgIF2α-S71A mutant, supporting the idea that induced TgIF2K-D phosphorylation of TgIF2α is central for *Toxoplasma* to persist in the extracellular environment (FIG. 11). Intracellular tachyzoites proliferate within a parasitophorous vacuole membrane that operates as a molecular sieve and regulates the acquisition of nutrients from the host cell. Upon exit from their host cell, the tachyzoites must find a new host cell in order to survive and replicate. The extracellular environment is likely to be reduced in essential nutrients that are available to the parasite, and/or the tachyzoites may not be equipped with the uptake mechanisms needed to acquire them. The data presented herein suggests that TgIF2α phosphorylation serves to protect the parasite during this period of vulnerability. One possible explanation for this observation is that global translation control enables the tachyzoites to conserve energy and nutrients, and may also induce preferential translation of key proteins required for extracellular survival (e.g. membrane transporters or a new array of metabolic enzymes). Such preferential translation of transcripts, such as ATF4 in mammals and Gcn4 in *S. cerevisiae*, during eIF2α phosphorylation are central for ameliorating nutrient stress. Wek, R. C., H. Y, 2006. The importance the parasite overcoming extracellular stress has significance in pathogenesis as demonstrated by our prior report that the TgIF2α-S71A mutant has reduced virulence when inoculated into mice. *Toxoplasma* strains differing in virulence are also suggested to differ in their ability to initiate translational control; hypervirulent strains are able to phosphorylate TgIF2α faster and more robustly than hypovirulent strains during extracellular stress.

The mechanisms employed by tachyzoites to overcome the dramatic changes in its extracellular environment are poorly understood, but have recently emerged as a new area of intensive research. Microarray analyses have revealed significant changes in the transcriptome between intra- and extracellular tachyzoites. Lescault, P. J., A. B. Thompson, V. Patil, D. Lirussi, A. Burton, J. Margarit, J. Bond, and M. Matrajt. 2010. *Genomic data reveal Toxoplasma gondii differentiation mutants are also impaired with respect to switching into a novel extracellular tachyzoite state. PLoS One* 5:e14463. Generally, intracellular parasites favor expression of genes involved in metabolism and DNA replication, while *Toxoplasma* in the extracellular environment activate genes focused on invasion, motility and signal transduction.

Coincident with the reprogramming of the transcriptome, extracellular parasites form a novel plant-like vacuole/vacuolar compartment (PLV/VAC). The PLV/VAC may protect parasites from osmotic or ionic stresses encountered outside host cells, or mediate the proteolytic maturation of proproteins targeted to micronemes, a cellular compartment important for the parasite invasion into host cells. Francia, M. E., 2011. Several studies have also shown that extracellular parasites undergo a metabolic shift from oxidative phosphorylation to glycolysis in order to generate the ATP required for gliding motility and invasion. Lin, S. S., M. Blume, N. von Ahsen, U. Gross, and W. Bohne. 2011. *Extracellular Toxoplasma gondii tachyzoites do not require carbon source uptake for ATP maintenance, gliding motility and invasion in the first hour of their extracellular life. International journal for parasitology*. Collectively, these studies suggest that tachyzoites undergo extensive changes in their morphology, metabolism, and transcriptome when transitioning to the extracellular environment.

Translational control through TgIF2α phosphorylation provides an additional mechanism that can modulate *Toxoplasma* gene expression that is designed to facilitate extracellular survival. The data discussed herein support this model, illustrating that parasites lacking the GCN2-like TgIF2K-D are significantly impaired in their ability to survive outside of host cells. In addition to TgIF2K-D, *Toxoplasma* is suggested to express three other eIF2α kinases that are each proposed to respond to unique stress arrangements or environmental cues. TgIF2K-A resides in the parasite endoplasmic reticulum and is suggested to function analogous to mammalian PEK/PERK TgIF2K-B is a parasite-specific eIF2α kinase likely to respond to a cytosolic stress. Narasimhan, J., B. R. Joyce, A. Naguleswaran, A. T Smith, M R. Livingston, S. E. Dixon, I. Coppens, R. C. Wek, and W. J. Sullivan, Jr. 2008. *Translation Regulation by Eukaryotic Initiation Factor*-2 *Kinases in the Development of Latent Cysts in Toxoplasma gondii. J Biol Chem* 283:16591-16601. Finally, TgIF2K-C is another GCN2-like protein kinase present in the *Toxoplasma* genome. However, this putative eIF2α kinase appears to lack an RWD that was reported to be essential for Gcn2 activity in the yeast model system. The data presented herein clearly demonstrates that deletion of TgIF2K-D alone is sufficient to disrupt the translational control required for the parasite to cope with the extracellular environment. Accordingly, TgIF2K-D and the eIF2α kinase stress response pathway is clearly a therapeutic target.

The tandem arrangement of GCN2-related eIF2α kinases is also found in the related parasite, *Plasmodium falciparum*. Conservation of multiple GCN2-related kinases may indicate that each phosphorylates eIF2α in response to distinct stress conditions. The *P. falciparum* PF14_0264 product is most closely related to TgIF2K-D and contains an RWD domain, while PfeIK1 appears to lack an RWD domain and has recently been reported to respond to amino acid starvation during the intraerythrocyte ring stage. This observation suggests that the RWD/GCN1 regulatory network may not be essential for invoking translational control during certain nutritional deficiencies.

GCN2-like protein kinases lacking the RWD domain are not restricted to Apicomplexa. Three GCN2-related kinases have been described in *Dictyostelium* (IFKA through C) but only IFKC possesses a RWD domain. *Dictyostelium* is capable of developing a fruiting body, a process that is induced upon nutrient starvation. Although involved in regulating *Dictyostelium* development, neither IFKA nor IFKB appear to represent the initial sensor for this stress, supporting the idea that different GCN2 isoforms sense distinct stress conditions. The role of IFKC in this process has not yet been studied.

MATERIALS AND METHODS

Allelic Replacement Vector for TgIF2α-S71A

To generate the allelic replacement construct, two fragments (−2600 bp to −1411 bp and −1238 bp to +440 bp) were amplified and inserted on opposing ends of the CAT minigene cassette within the pminCAT/HXGPRT+ vector, as illustrated in FIG. 1A (Roos et al., 1994). The ~1.2 kb 5' TgIF2α flanking sequence (−2600 bp to −1411 bp) was inserted between the NotI and BamHI sites using the oligonucleotides "5'S71A for+NotI" and "5'S71A rev+BamHI". Sequences for all primers used for this study are listed in Table 3. The 3' TgIF2α flanking fragment (−1238 bp to +440 bp), which includes the entire first exon of TgIF2α as well as ~1.2 kb of upstream sequence, was inserted into the BclI site of the construct described above. A point substitution was generated to change Ser71 to Ala71 using the QuikChange XL mutagenesis kit (Stratagene) and the oligonucleotides "TgIF2α S71A quikchange 1F" and "TgIF2α S71A quikchange 1R".

TABLE 3

List of some of the primers used in this study

| SEQ ID NO. | Primer Name | Sequence |
|---|---|---|
| SEQ ID NO. 1 | 5' S71A for + NotI | gcgcgcggccgcGCCGGGTCGTTTTGTATAG |
| SEQ ID NO. 2 | 5' S71A rev + BamHI | ggcgggatccCGCTTCACCTGTCGGTTTCC |
| SEQ ID NO. 3 | 3' S71A for + BclI | gcgctgatcaCTCACCGCCTCGTCGCTGTGT |
| SEQ ID NO. 4 | 3' S71A rev + BclI | gcgctgatcaGGTGTCGGATGTCAGGTGGCGG |
| SEQ ID NO. 5 | TgIF2α S71A quikchange 1F | TCTCATGAGTGAACTGGCCAAACGGCGGTTCCGC |
| SEQ ID NO. 6 | TgIF2α S71A quikchange 1R | GCGGAACCGCCGTTTGGCCAGTTCACTCATGAGA |
| SEQ ID NO. 7 | S71A screen for | CCTGCGCGAGTCTGTGAG |
| SEQ ID NO. 8 | S71A screen rev | GGTGTCGGATGTCAGGTGGCGG |
| SEQ ID NO. 9 | TgIF2α Taqman for | CAACAACATGGAAGGCATGATT |
| SEQ ID NO. 10 | TgIF2α Taqman rev | GATCGACGCGGAGAACCA |
| SEQ ID NO. 11 | FAM-WT TgIF2α | FAM-CATGAGTGAACTGAGCA |
| SEQ ID NO. 12 | VIC-TgIF2α-S71A | VIC-ATGAGTGAACTGGCCAA |

Generation of TgIF2α-S71A Mutant Parasites

Twenty-five micrograms of the TgIF2α-S71A allelic replacement vector was linearized with NotI and transfected into RH strain ΔKu80 parasites (Fox et al., 2009; Huynh and Carruthers, 2009) as previously described (Roos et al., 1994). Parasites were cultivated in confluent monolayers of human foreskin fibroblasts (HFF) under standard conditions (DMEM plus 1% FBS (Invitrogen) in a humidified incubator at 37° C. with 5% $CO_2$). Transgenic parasites were selected in 20 μM chloramphenicol and cloned by limiting dilution in 96-well plates. Parasite clones were screened by immunoblot analysis of the phosphorylation status of TgIF2α phosphorylation following stress with 10 μM tunicamycin for 1 hour (Narasimhan et al., 2008b). Positive clones were confirmed independently using a PCR-based approach: replacement of the Ser71-encoding nucleotides with those that encode Ala71 creates a unique restriction site, MscI (FIG. 1A). Genomic DNA was isolated from parasite clones using the Qiagen DNeasy kit, and the designated portion of the TgIF2α genomic locus was amplified by PCR using oligonucleotides "S71A screen for" and "S71A screen rev" (FIG. 1A). The resulting amplicon was gel-purified and digested with MscI. Clones with the S71A substitution yield two bands of 340 and 220 bp, whereas the parental strain yields a single 560 bp band.

TgIF2α Phosyphorylation Detection and Protein Radiolabelling

Phosphorylation of TgIF2α was monitored by Western blotting performed in accordance with standard methods. Intracellular parasites were released from HFF host cells by physical disruption (scraping and/or syringe passage) and purified by filtration through 3 micron polycarbonate filters (Roos et al., 1994). The purified extracellular parasites were incubated in DMEM containing 1% FBS at 37° C. under 5% $CO_2$ for the designated length of time. Fifty μg of protein lysates were separated by electrophoresis using a 10% Bis-Tris acrylamide gel (Invitrogen). Proteins were transferred to nitrocellulose membranes and probed with either rabbit anti-TgIF2α antibody (diluted 1:10,000) or phospho-specific (Ser71) TgIF2α antibody (diluted 1:500) followed by an anti-rabbit IgG-horseradish peroxidase conjugate (GE Healthcare) (Narasimhan et al., 2008b; Sullivan Jr. et al., 2004b). Total and phospho-TgIF2α was visualized using an ECL Western blotting substrate (Pierce).

In experiments in which parasites were radiolabeled, equal numbers of extracellular tachyzoites were resuspended in labeling media, Dulbecco's modified Eagle's medium without L-methionine, L-cysteine, L-glutamine, or sodium pyruvate (Invitrogen #21013-024) supplemented with 5% fetal-bovine serum, 1 mM L-glutamine, 0.5 mM sodium pyruvate. 0.145 mCi of Express Protein Label Mix containing [$^{35}$S]methionine and [$^{35}$S]cysteine (PerkinElmer Life Sciences) was added to the sample and incubated for 1 h. Samples were washed twice in PBS, and a portion was counted to determine similar uptake of the radiolabel. Parasites were resuspended in lysis buffer and sonicated. Equal amounts of total protein from each lysate preparation were separated by SDS/PAGE, and radiolabeled proteins were visualized by autoradiography. Results are presented as means S.E. that were derived from three independent experiments. The Student's t test was used to determine the statistical significance.

Competitive Parasite Fitness Assay Using TaqMan Probes

The comparative fitness assay was based on a protocol outlined in (Fohl and Roos, 2003). Following filter-purification, $5\times10^5$ parental ΔKu80 (referred to as wild-type, or WT) and TgIF2α-S71A mutant parasites were mixed in 10 ml DMEM+1% FBS and added to a T-25 $cm^2$ flask containing a monolayer of HFF host cells. A sample of the mixed parasites was collected every 72 hours for a total of 9 days. At each time point, $10^5$ parasites were used to infect a fresh HFF monolayer. Genomic DNA was isolated from each parasite sample using the DNeasy kit (Qiagen). TaqMan-based allelic discrimination assay was performed using a forward and reverse oligonucleotides "TgIF2α TaqMan for" and "TgIF2α TaqMan rev" and a combination of probes used to identify the WT or mutant allele ("FAM-WT TgIF2α" and "VIC-TgIF2α-S71A", respectively). PCR reactions were performed in triplicate using the 7500 Real-time PCR system and analyzed with relative quantification software (SDS software Version 1.2.1, Applied Biosystems).

Parasite Growth Assays

*Toxoplasma* doubling assays were performed as previously described (Fichera et al., 1995). Intracellular ΔKu80 and TgIF2α-S71A parasites were physically removed from host cells by syringe passage. $10^5$ of each were immediately applied to a fresh monolayer of HFFs grown on coverslips (0 hr), or incubated in culture media at 37° C. with 5% $CO_2$ in absence of host cells for 4 or 8 hours prior to infection. The number of parasites per vacuole was visualized every 8 hours by immunofluorescence assay (IFA) using the DNA intercalator 4',6-diamidino-2-phenylindole (DAPI). Experiments were carried out in triplicate using separate biological samples. *Toxoplasma* growth in culture was also evaluated by a standard plaque assay (Roos et al., 1994). 500 ΔKu80 or TgIF2α-S71A mutant parasites were allowed to infect a HFF monolayer; the degree of host cell lysis was evaluated on day 5-7 using Coomassie Brilliant Blue staining. The area of clearing representing the degree of monolayer disruption was determined using Alpha Innotech Imaging system. Experiments were carried out in triplicate using separate biological replicates. Results from a single representative experiment are shown.

*Toxoplasma* Adhesion and Invasion Assay

The red/green adhesion and invasion assay was carried out as previously described (Huynh et al., 2003). Immediately following egress, $1\times10^7$ ΔKu80 or TgIF2α-S71A parasites were allowed to adhere/invade a confluent monolayer of HFF cells cultured on glass coverslips in 12-well plates. Prior to permeabilization, the infected cells were incubated with a mouse anti-Sag1 immune serum (Meridian Life Sciences) to visualize adhered parasites. The infected cells were then washed with PBS, permeabilized with 0.2% Triton X-100 in PBS and incubated with a second primary immune serum, rabbit anti-Sag1 (a generous gift from John Boothroyd, Stanford). A combination of anti-mouse Alexa fluor 488 and anti-rabbit Alexa fluor 594 was applied to the infected cells to distinguish between adhered versus invaded parasites. In the merged images, the adhered parasites appear yellow and the invaded parasites are red. The numbers of adhered and invaded parasites were counted for a minimum of 6 different microscope fields. The standard error and Student's t test was applied as described above.

*Toxoplasma* Motility Assay $10^6$ ΔKu80 or TgIF2α-S71A parasites were allowed to adhere and glide along a poly-L lysine coated coverslip for 30 min in DMEM containing 1% FBS. The adhered parasites and surface protein "trails" were detected with a mouse anti-Sag1 immune serum as previously described (Dobrowolski and Sibley, 1996). The number of ΔKu80 or TgIF2α-S71A parasites with trails was recorded from a minimum of 6 independent microscope fields.

*Toxoplasma* Egress Assay

Parasite egress assays were performed as previously described (Black et al., 2000). Briefly, $10^6$ ΔKu80 or TgIF2α-S71A parasites were cultivated in HFFs at 37° C., 5% $CO_2$ overnight. To induce egress of the tachyzoites, infected monolayers were exposed to 2 A23187 for 0, 0.5, 1, 2, 3, or 4 min. At each time interval, the parasites were fixed with cold methanol and the percentage of parasite egress was recorded from 10 random microscope fields.

Animal Studies

Female BALB/c mice (18-20 grams) were injected intraperitoneally with 10 or $10^2$ ΔKu80 or TgIF2α-S71A parasites (10 mice per group) harvested immediately after egress from HFF cells. Animals were monitored twice daily until significant illness was observed at which time the moribund animals were euthanized. Time to moribund state was recorded for each infected mouse.

Parasite Culture

*Toxoplasma* tachyzoites were maintained in human foreskin fibroblasts (HFF) in Dulbecco Modified Eagle's Media (DMEM) containing 25 mM glucose and 4 mM glutamine (Invitrogen) supplemented with 1% heat inactivated fetal bovine serum (Gibco/Invitrogen) at 37° C. and 5% $CO_2$.

Cloning of the TgIF2K-D cDNA

Tachyzoite mRNA was used to generate a cDNA library (Omniscript, Qiagen) for the amplification of the TgIF2K-D open reading frame (ORF). This PCR amplification employed primers specific to the TgIF2K-D gene that was annotated in the *Toxoplasma* database (www.toxodb.org, TgME49_119610). Tachyzoite mRNA was reverse transcribed using SuperScript One-Step RT-PCR kit (Invitrogen) with random and oligo-dT primers according to the manufacturer's recommendations. All PCRs were carried out with Phusion DNA-polymerase (Finnzymes) using the provided GC buffer. The GeneRacer Kit (Invitrogen) was used for the 5'- and 3'-rapid amplification of cDNA ends (RACE) of the TgIF2K-D gene.

Generation of TgIF2K-D Knockout Parasites

In order to generate TgIF2K-D knockout parasites (ΔIF2K-D), ~1.5 kb DNA fragments upstream and downstream of the start and stop codons encoded in the TgIF2K-D locus were amplified. Referring now to Table 2, oligonucleotide primers used to amplify the 5' flanking sequence were designated #1 and #2, and the primers used to amplify the 3' flanking sequence were #3 and #4. The amplified DNA was inserted into the pDHFR*-TSc3 vector, such that these fragments flanked opposing ends of a modified dihydrofolate reductase-thymidylate synthase (DHFR*-TS) minigene, which confers resistance to pyrimethamine. Hinnebusch, A. G. 2005. The resulting knockout vector was designated ΔTgIF2K-D::DHFR*. Fifty μg of the ΔTgIF2K-D::DHFR* knockout vector was linearized with NotI and transfected into RH strain parasites lacking Ku80. Fox, B. A., J. G. Ristuccia, J. P. Gigley, and D. J. Bzik. 2009. *Efficient gene replacements in Toxoplasma gondii strains deficient for nonhomologous*

*end joining. Eukaryot Cell* 8:520-529. Transfected parasites were grown in HFF cells in the above defined DMEM supplemented with 1 μM pyrimethamine and cloned by limiting dilutions. Individual parasite clones were screened by PCR to confirm the replacement of the TgIF2K-D genomic locus with the DHFR*-TS minigene.

To confirm that the correct insertion occurred at the TgIF2K-D locus, primers complementary to the 3'-UTR of the DHFR* minigene (#10) and upstream of the insertion site (#9) were used in a PCR assay with genomic DNAs purified from the candidate knockout parasites. PCR assays using primers #5 and #6, which are complementary to exon III, and #7 and #8 that were used to generate the genetic tagging vector (see below) were carried out to verify the absence of the complete TgIF2K-D genomic locus. Loss of TgIF2K-D mRNA expression was verified by RT-PCR using primers complementary to sequences upstream (#11) and downstream (#12) of the encoded protein kinase domain. As control, a portion of *Toxoplasma* actin (TgME49_009030) mRNA was amplified by RT-PCR using primers #13 and #14. Genetic Tagging of TgIF2K-D For the expression of TgIF2K-D tagged with hemagglutinin (HA) at its C-terminus, a 1.2-kb DNA fragment containing exon XVIII was amplified using *Toxoplasma* genomic DNA as the template and primers #7 and #8. The amplified DNA segment was then inserted into the vector 3xHA-LIC-DHFR-TS using the ligation-independent cloning method (40). LIC-HA3x-DHFR-Ts is a derivative of pYFP-LIC-DHFR in which the YFP coding fragment had been replaced with three contiguous HA tags. Huynh, M. H., and V. B. Carruthers. 2009. *Tagging of endogenous genes in a Toxoplasma gondii strain lacking Ku*80. *Eukaryot Cell* 8:530-539. Fifty μg of the TgIF2K-D-HA3× plasmid was linearized with the restriction enzyme AscI and then transfected into RHΔKu80 parasites. Following limiting dilutions, positive clones were identified using a monoclonal antibody that specifically recognizes the HA tag (Roche).

The 1.2-kb DNA fragment containing exon XVIII (amplified with primers #7 and #8) was also ligated into a LIC-HA2X-DD-DHFR-TS vector to generate a TgIF2K-D fusion with 2×HA and a Shield-regulated destabilization domain (DD) at the C-terminus (2×DD). Huynh, M. H., 2009. Following transfection of this linearized plasmid, individual parasite clones were screened for the stabilization of TgIF2K-$D_{2\times DD}$ in the presence of Shield-1 (500 nM, Clontech) using the anti-HA monoclonal antibody.

Comparative Fitness Assay

The comparative fitness assay was carried out as described previously by Joyce et al. (16), with the exception that SYBR green-based quantitative real-time PCR (qPCR) was performed using primers that specifically delineated between parental ΔKu80, referred to as wild-type (WT), and ΔIF2K-D parasites. In brief, equal numbers of filter-purified parental and ΔIF2K-D parasites ($5\times10^5$) were co-cultured in the same flask of HFF host cells. At 72 hours post-infection, $10^5$ parasites of the mixed population were isolated from the lysed culture and then transferred to a fresh HFF monolayer for an additional 72 hours. This resulted in a total of 6 days of HFF infection by using two serial passages. Genomic DNA (gDNA) from the parasite samples was isolated using the DNeasy Kit (Qiagen) and used in qPCR assays. Primers used to distinguish between WT from ΔIF2K-D parasites included #15 and #16, and #17 and #18, as indicated. qPCR measurements were normalized by amplifying the 5'-UTR of TgIF2K-D, which is present in both WT and ΔIF2K-D parasites (primers #19 and #20). 25 ng of gDNA was used in the qPCR assays, which were performed in triplicate using the 7500 Real-Time PCR System (Applied Biosystems). Relative quantification software (SDS software, version 1.2.1) was used for the analysis. As a specificity control, SYBR green assays employing gDNA purified from either WT or ΔIF2K-D parasites were carried out to verify the specificity of primers in the qPCR assay (data not shown).

Parasite Proliferation Assays

*Toxoplasma* recovery from extracellular stress was analyzed using standard doubling and plaque assays. Parental ΔKu80 (WT), ΔIF2K-D, and TgIF2α-S71A parasites were physically released from host cells by syringe passage and then filter purified to remove host cell debris. $10^6$ parasites were subjected to an extracellular stress assay for 0, 8, or 10 hours in culture medium at 37° C. and 5% $CO_2$ without host cells prior to infecting HFF host cells. Parasites were quantitated using a standard counting assay with counts performed every 8 hours post-infection. Parasite counting assays were carried out in triplicate using separate biological samples and a representative experiment is shown. In the plaque assays, 500 WT, ΔIF2K-D, TgIF2α-S71A, or TgIF2K-$D_{2\times DD}$ parasites were used to infect HFF monolayers in 12-well plates following extracellular incubation for up to 10 hours, as indicated. The degree of host cell lysis at 7 days post-infection was determined by crystal violet staining of methanol fixed cells. Measurements of the lysed areas were determined using an Alpha Innotech Imaging system, and a representative experiment of three independent experiments presented.

Western Blotting

Western blot analyses of TgIF2α phosphorylation were carried out as previously described. To analyze the stabilization of the TgIF2K-$D_{2\times DD}$ protein, intracellular parasites were grown for up to 24 hours in medium supplemented with 500 nM Shield-1 prior to physical release from the host cells. HA-tagged proteins were detected by western blot analyses after resolving parasite lysate on a 3-8% Tris-acetate polyacrylamide gradient gel. Rat monoclonal antibody that specifically recognizes the HA tag (Roche) was used as a primary antibody and an anti-rat IgG antibody conjugated with horseradish peroxidase (GE Healthcare) was used as a secondary antibody. HA-tagged proteins were visualized using a chemiluminescence western blotting substrate (Pierce).

Measurements of Protein Synthesis.

Intracellular parasites were mechanically released from host cells as described above and $2.5\times10^7$/ml tachyzoites were transferred into *Toxoplasma* culture medium lacking methionine and cysteine. Labeling was initiated by adding [$^{35}$5]-Met/Cys-label (ICN) to a final concentration of 200 μCi/ml. After 1 hour incubation in DMEM at 37° C. and 5% $CO_2$, samples were immediately put on ice. Parasites were harvested by centrifugation at 4° C., cell pellets were washed twice with ice cold PBS and then lysed in 100 μl RIPA buffer. Uptake of the $^{35}$S during the 1 hour pulse radiolabeling was similar between the WT and mutant parasites. For each sample, equal amounts of proteins were precipitated by adding trichloroacetic acid (TCA) to a final concentration of 10%. After incubating on ice for 30 min, samples were collected by centrifugation 10,000×g for 30 min at 4° C. The TCA precipitates were washed twice with acetone and resuspended in an equal volume of PBS. Incorporation of the radiolabeled amino acids was determined using a scintillation counter. All radiolabeling experiments were presented as an average of three independent samples, with p-values and standard errors determined using analysis of variance (ANOVA).

Immunofluorescence Assays.

HFF monolayers were grown on coverslips, infected for 24 hours, and then fixed in 3% paraformaldehyde. Immunofluorescence analyses using a rat monoclonal antibody that recognizes the HA tag (Roche) followed by goat anti-rat AlexaFluor488 as the secondary antibody (Invitrogen) was performed as previously described.

REFERENCES

Balaji, S., Babu, M. M., Iyer, L. M., and Aravind, L. (2005). Discovery of the principal specific transcription factors of Apicomplexa and their implication for the evolution of the AP2-integrase DNA binding domains. Nucleic Acids Res 33, 3994-4006.

Black, M. W., Arrizabalaga, G., and Boothroyd, J. C. (2000). Ionophore-resistant mutants of *Toxoplasma gondii* reveal host cell permeabilization as an early event in egress. Mol Cell Biol 20, 9399-9408.

Black, M. W., and Boothroyd, J. C. (2000). Lytic cycle of *Toxoplasma gondii*. Microbiol Mol Biol Rev 64, 607-623.

Dever, T. E., Feng, L., Wek, R. C., Cigan, A. M., Donahue, T. F., and Hinnebusch, A. G. (1992). Phosphorylation of initiation factor 2 alpha by protein kinase GCN2 mediates gene-specific translational control of GCN4 in yeast. Cell 68, 585-596.

Dobrowolski, J. M., and Sibley, L. D. (1996). *Toxoplasma* invasion of mammalian cells is powered by the actin cytoskeleton of the parasite. Cell 84, 933-939.

Fennell, C., Babbitt, S., Russo, I., Wilkes, J., Ranford-Cartwright, L., Goldberg, D. E., and Doerig, C. (2009). PfeIK1, a eukaryotic initiation factor 2alpha kinase of the human malaria parasite *Plasmodium falciparum*, regulates stress-response to amino-acid starvation. Malar J 8, 99.

Fichera, M. E., Bhopale, M. K., and Roos, D. S. (1995). In vitro assays elucidate peculiar kinetics of clindamycin action against *Toxoplasma gondii*. Antimicrob Agents Chemother 39, 1530-1537.

Finn, R. D., J. Mistry, J. Tate, P. Coggill, A. Heger, J. E. Pollington, O. L. Gavin, P. Gunasekaran, G. Ceric, K. Forslund, L. Holm, E. L. Sonnhammer, S. R. Eddy, and A. Bateman. 2010. The Pfam protein families database. Nucleic acids research 38:D211-222.

Fohl, L. M., and Roos, D. S. (2003). Fitness effects of DHFR-TS mutations associated with pyrimethamine resistance in apicomplexan parasites. Mol Microbiol 50, 1319-1327.

Fox, B. A., Ristuccia, J. G., Gigley, J. P., and Bzik, D. J. (2009). Efficient gene replacements in *Toxoplasma gondii* strains deficient for nonhomologous end joining Eukaryot Cell 8, 520-529.

Francia, M. E., S. Wicher, D. A. Pace, J. Sullivan, S. N. Moreno, and G. Arrizabalaga. 2011. A *Toxoplasma gondii* protein with homology to intracellular type Na(+)/H(+) exchangers is important for osmoregulation and invasion. Exp Cell Res.

Hill, D. E., Chirukandoth, S., and Dubey, J. P. (2005). Biology and epidemiology of *Toxoplasma gondii* in man and animals. Anim Health Res Rev 6, 41-61.

Hinnebusch, A. G. (2005). Translational regulation of GCN4 and the general amino acid control of yeast. Annu Rev Microbiol 59, 407-450.

Huynh, M. H., and Carruthers, V. B. (2009). Tagging of endogenous genes in a *Toxoplasma gondii* strain lacking Ku80. Eukaryot Cell 8, 530-539.

Huynh, M. H., Rabenau, K. E., Harper, J. M., Beatty, W. L., Sibley, L. D., and Carruthers, V. B. (2003). Rapid invasion of host cells by *Toxoplasma* requires secretion of the MIC2-M2AP adhesive protein complex. EMBO J 22, 2082-2090.

Joyce, B. R., S. F. Queener, R. C. Wek, and W. J. Sullivan, Jr. 2010. Phosphorylation of eukaryotic initiation factor-2 {alpha} promotes the extracellular survival of obligate intracellular parasite *Toxoplasma gondii*. Proc Natl Acad Sci USA 107:17200-17205.

Khan, A., Behnke, M. S., Dunay, I. R., White, M. W., and Sibley, L. D. (2009). Phenotypic and gene expression changes among clonal type I strains of *Toxoplasma gondii*. Eukaryot Cell 8, 1828-1836.

Lin, S. S., M. Blume, N. von Ahsen, U. Gross, and W. Bohne. 2011. Extracellular *Toxoplasma gondii* tachyzoites do not require carbon source uptake for ATP maintenance, gliding motility and invasion in the first hour of their extracellular life. International journal for parasitology.

Mohrle, J. J., Zhao, Y., Wernli, B., Franklin, R. M., and Kappes, B. (1997). Molecular cloning, characterization and localization of PfPK4, an eIF-2alpha kinase-related enzyme from the malarial parasite *Plasmodium falciparum*. Biochem J 328 (Pt 2), 677-687.

Moraes, M. C., Jesus, T. C., Hashimoto, N. N., Dey, M., Schwartz, K. J., Alves, V. S., Avila, C. C., Bangs, J. D., Dever, T. E., Schenkman, S., et al. (2007). Novel Membrane-Bound eIF2 {alpha} Kinase in the Flagellar Pocket of *Trypanosoma brucei*. Eukaryot Cell 6, 1979-1991.

Narasimhan, J., Joyce, B. R., Naguleswaran, A., Smith, A. T., Livingston, M. R., Dixon, S. E., Coppens, I., Wek, R. C., and Sullivan, W. J., Jr. (2008a). Translation regulation by eukaryotic initiation factor-2 kinases in the development of latent cysts in *Toxoplasma gondii*. J Biol Chem 283, 16591-16601.

Narasimhan, J., Joyce, B. R., Naguleswaran, A., Smith, A. T., Livingston, M. R., Dixon, S. E., Coppens, I., Wek, R. C., and Sullivan, W. J., Jr. (2008b). Translation Regulation by Eukaryotic Initiation Factor-2 Kinases in the Development of Latent Cysts in *Toxoplasma gondii*. J Biol Chem 283, 16591-16601.

Roos, D. S., Donald, R. G., Morrissette, N. S., and Moulton, A. L. (1994). Molecular tools for genetic dissection of the protozoan parasite *Toxoplasma gondii*. Methods Cell Biol 45, 27-63.

Scheuner, D., Song, B., McEwen, E., Liu, C., Laybutt, R., Gillespie, P., Saunders, T., Bonner-Weir, S., and Kaufman, R. J. (2001). Translational control is required for the unfolded protein response and in vivo glucose homeostasis. Molecular Cell 7, 1165-1176.

Schroder, M., and Kaufman, R. J. (2005a). ER stress and the unfolded protein response. Mutat Res 569, 29-63.

Schroder, M., and Kaufman, R. J. (2005b). The mammalian unfolded protein response. Annu Rev Biochem 74, 739-789.

Sonenberg, N., and Hinnebusch, A. G. (2009). Regulation of translation initiation in eukaryotes: mechanisms and biological targets. Cell 136, 731-745.

Sullivan Jr., W. J., Narasimhan, J., Bhatti, M. M., and Wek, R. C. (2004a). Parasite-specific eukaryotic initiation factor-2 (eIF2) kinase required for stress-induced translation control. Biochem J 380, 523-531.

Wek, R. C., and Cavener, D. R. (2007a). Translational control and the unfolded protein response. Antioxid Redox Signal 9, 2357-2371.

Wek, R. C., Jiang, H. Y., and Anthony, T. G. (2006). Coping with stress: eIF2 kinases and translational control. Biochem Soc Trans 34, 7-11.

While the novel technology has been illustrated and described in detail in the figures and foregoing description, the same is to be considered as illustrative and not restrictive in character, it being understood that only the preferred embodiments have been shown and described and that all changes and modifications that come within the spirit of the novel technology are desired to be protected. As well, while the novel technology was illustrated using specific examples, theoretical arguments, accounts, and illustrations, these illustrations and the accompanying discussion should by no means be interpreted as limiting the technology. All patents, patent applications, and references to texts, scientific treatises, publications, and the like referenced in this application are incorporated herein by reference in their entirety.

We claim:

1. A method of identifying a compound, comprising the steps of: providing at least one translation initiation factor identified in a single celled eukaryotic parasite, wherein the translation initiation factor is phosphorylated by a TgIF2K-D kinase having at least 90% identity to SEQ ID NO: 13; contacting the TgIF2k-D kinase of SEQ ID NO: 13 with at least one compound; measuring the activity of the TgIF2K-D kinase of SEQ ID NO: 13 in the presence of the at least one compound; and identifying the at least one compound as an inhibitor of TgIF2K-D kinase of SEQ ID NO: 13 if the at least one compound reduces the activity of the TgIF2K-D kinase of SEQ ID NO: 13.

2. The method according to claim 1, wherein the single celled parasite is selected from the group of genera consisting of *Toxoplasma, Plasmodium* and *Cryptosporidium.*

* * * * *

SEQUENCE LISTING

```
<160> NUMBER OF SEQ ID NOS: 70

<210> SEQ ID NO 1
<211> LENGTH: 31
<212> TYPE: DNA
<213> ORGANISM: Artificial Sequence
<220> FEATURE:
<223> OTHER INFORMATION: Primer

<400> SEQUENCE: 1

gcgcgcggcc gcgccgggtc gttttgtata g                                     31


<210> SEQ ID NO 2
<211> LENGTH: 30
<212> TYPE: DNA
<213> ORGANISM: Artificial Sequence
<220> FEATURE:
<223> OTHER INFORMATION: Primer

<400> SEQUENCE: 2

ggcgggatcc cgcttcacct gtcggtttcc                                       30


<210> SEQ ID NO 3
<211> LENGTH: 31
<212> TYPE: DNA
<213> ORGANISM: Artificial Sequence
<220> FEATURE:
<223> OTHER INFORMATION: Primer

<400> SEQUENCE: 3

gcgctgatca ctcaccgcct cgtcgctgtg t                                     31


<210> SEQ ID NO 4
<211> LENGTH: 32
<212> TYPE: DNA
<213> ORGANISM: Artificial Sequence
<220> FEATURE:
<223> OTHER INFORMATION: Primer

<400> SEQUENCE: 4

gcgctgatca ggtgtcggat gtcaggtggc gg                                    32


<210> SEQ ID NO 5
<211> LENGTH: 34
<212> TYPE: DNA
<213> ORGANISM: Artificial Sequence
<220> FEATURE:
<223> OTHER INFORMATION: Primer

<400> SEQUENCE: 5

tctcatgagt gaactggcca aacggcggtt ccgc                                  34


<210> SEQ ID NO 6
<211> LENGTH: 34
<212> TYPE: DNA
<213> ORGANISM: Artificial Sequence
<220> FEATURE:
<223> OTHER INFORMATION: Primer

<400> SEQUENCE: 6

gcggaaccgc cgtttggcca gttcactcat gaga                                  34
```

-continued

<210> SEQ ID NO 7
<211> LENGTH: 18
<212> TYPE: DNA
<213> ORGANISM: Artificial Sequence
<220> FEATURE:
<223> OTHER INFORMATION: Primer

<400> SEQUENCE: 7
cctgcgcgag tctgtgag 18

<210> SEQ ID NO 8
<211> LENGTH: 22
<212> TYPE: DNA
<213> ORGANISM: Artificial Sequence
<220> FEATURE:
<223> OTHER INFORMATION: Primer

<400> SEQUENCE: 8
ggtgtcggat gtcaggtggc gg 22

<210> SEQ ID NO 9
<211> LENGTH: 22
<212> TYPE: DNA
<213> ORGANISM: Artificial Sequence
<220> FEATURE:
<223> OTHER INFORMATION: Primer

<400> SEQUENCE: 9
caacaacatg gaaggcatga tt 22

<210> SEQ ID NO 10
<211> LENGTH: 18
<212> TYPE: DNA
<213> ORGANISM: Artificial Sequence
<220> FEATURE:
<223> OTHER INFORMATION: Primer

<400> SEQUENCE: 10
gatcgacgcg gagaacca 18

<210> SEQ ID NO 11
<211> LENGTH: 17
<212> TYPE: DNA
<213> ORGANISM: Artificial Sequence
<220> FEATURE:
<223> OTHER INFORMATION: Probe

<400> SEQUENCE: 11
catgagtgaa ctgagca 17

<210> SEQ ID NO 12
<211> LENGTH: 17
<212> TYPE: DNA
<213> ORGANISM: Artificial Sequence
<220> FEATURE:
<223> OTHER INFORMATION: Probe

<400> SEQUENCE: 12
atgagtgaac tggccaa 17

<210> SEQ ID NO 13
<211> LENGTH: 11361
<212> TYPE: DNA
<213> ORGANISM: Toxoplasma gondii

<400> SEQUENCE: 13
aacgattcct ctgtgccctc tgtcttcttc attgatttga ctttccccca gctctgcaga 60
atgtccacat tttaccaccg tgtcagctgc ctccaaggtc gaccgtgttt gtgtcgccga 120
aagtgaaaac agtccacctc tcggtgattc tagccgtcag ttctcttttc tccgggggaa 180
acgttcacct ttctctctga ctttctgtct gtcctcgctg actgggggtc tttacttcgg 240
catggacgtt tgccaggtcc ctcgctcgac ttctccgccg cttgttccac agtttcgttg 300
ctctcttggt gtgcagaact ccttttcaaa cgaaagtcct gtgtagagcc gtaggatcgc 360
cgttttccgc ctcccagagt gtcccgatac gctgcgtctg cctcccttgt cggctgtgcg 420
ctcctcgcct gtgcagcgct tcagagggaa cgcctgaacg cgcttttcgc gaagtccggt 480
tctttgtcac tgaccaatga gctttggttt ccacgcacaa tgtccagtaa agaaacaggc 540
gagctgggtc cggaaaacag ccttgttaag aggtgaaact tgctccgggg cagcatggat 600
gcgtctgcca ctcggttcgt gtgctttctt tcgtccgttc ttgacaatcg acactcccct 660
ggcccttcac tctttcgcag ctgacccaac gaacatatcg gcatcgtaac aacgcgctcg 720
cccctcattc tccgtttgtc tcatttggat ttttctacgt ctttccatcc acgcgtcaga 780
ctccccgtct gttgtagtgg cgtcacggct ggtggtatac ggcaaccaag caaaccgtag 840
tagaagccta ggaaacaggt gcattcgcgc gttctccttc ctcgccatct ctgtgggaga 900
tgcagcactg aagcggcaga ggccttcgag gcgtctcggt cttgagagcc tcttggccgt 960
tcagactgcg acgaaaccgc tcttgcgcgt ttctcctttc ccccgagatt tgctctgttt 1020
ccgcacacag tgaactgaac ggccgaggga ggcggcctgc aagacgacag cagatcttgg 1080
atcgacactg aggaggacaa aggcgatttc gggggagtga aacggggccc ctcgaggctc 1140
cagagaagag agacagagag gaggagaaga tccacgattt ccggtggctt ttccgttcat 1200
ccagaggaag agaaacggac ggagctggag cctgacgagg aagagaagaa agacaagtgt 1260
actcgatgct ggaggaacag agtgagtgag tgagcactcc gcgcctgtca accgggtgct 1320
tctgacgcga caaggatgcc tgggtctctg acagtaaccc agtccacgag tttcgtcgct 1380
gagtcgaatg cctggaaaga gctgcggttt ccgacttcgc tcgacgggca ccgaggagac 1440
tctctgttct cccattttcg ttacgccctg agcgagaact gtcgcatgtc tgtctgaccg 1500
cgtagacggt tcactcgcct cccagacact ggacagctcg tccacatccc gctccttgag 1560
ctgctctctc tggagagcga aagtgaatcc gcgagaatcc gagaatcgct tcttccttcg 1620
ccgcatgtag aggcgttcgt ttccactctt cccctccttc ccacctggcg ccacggttca 1680
cagacagcgt ttcgtaagcc agagggccgg aagcgactgc cgtctgtaca ccgcacatta 1740
ccgaaacgga acggctgtct ttcgccatgc gcgttgtggg catctgttga agcagtaggc 1800
gccccgtctg gtgttcctcc cggtgaagac caggtttttg tgaagcttct tcttcgactc 1860
gcccggcggc tccgacagct tgtgggctac agagtctcac gcgtatcctt tggcggatgc 1920
gcctgaagct ccggttcttc aacagggccg tacgagaacg ttggtctgcc gcctctgtat 1980
ctgcttaacg ggtacggcgt ttactcactc ttgtccccgt cctctgtagg gctggttccc 2040
ttccgaactc tcctcccttc gttcttgtcc tttatttctt cccatttagc tgcctcgctt 2100
gtctccaatt atgcatacgc tggattaacc gctcataagg acaggcccac gatgcggatt 2160
ggcacagaga cgcccccgggg gggaacgcga gctgcgagcg aagaggacgg agacgatgga 2220
tcttggacac tggtggcgtc gaaacgacgc aggcctcctc ctcgcacccc tccgggcctg 2280
gcgtcagctt cgcaggctcg ctcggcgcgg ggacgcgccg cggcgtctct ctccaaccgc 2340

-continued gcccgtagga gtctttcgca gcgctcgcgt cgccctcggc aggaggcgcg tccgcacggt 2400
tcaccgccgt gtgccttgag tgcttcggcg gctgcgggat ccgcagagac agttggagcg 2460
agtggggagg acgaggacgc aggccttcga gggggcgcgc aggagcaggg gacagcgcga 2520
gacctgcgag agcagtggcc agagttggcc gctgctgccc aagcaggctg gggcgagagc 2580
gccccccgc gcgcgacctc cagttgggcg acagtcgcgg caggaagctg cgggtccgcg 2640
cgggcgcctc tggggcaggc tctgcgaccg tgtctctcga cgcccacagg ccgcgaggcc 2700
cccccagcga acgtcccggg gcaggcgccc tgcggtgtgg cggagccgcg gaggccgggg 2760
gcgaaggcca gtgcgccgtc agggagttcg cggcgccagg agatgccacg ggaggttcca 2820
acgcgaccgc aaaccgcgcg agggcctgca gaggccgcga cggccagtgg tttggtcctg 2880
gggcggagtc cgaaaggtcc gcgcggaggc gaaacagagg ggagacggag gagcttgggc 2940
gaggagagga gagagtcgga tgggaaggct gaagggaaag gatcgcggaa gcctcaactc 3000
gacagagctg gcggcaagac ccagcaccgg ggatctcctg aggaggggcg agagaaggca 3060
gggggcctcg tggagacgaa cggcgaagct gcagaagcaa agcgaggccc ctcgaagaag 3120
gagcaccctg acaaggttgc ggaagaggcc aggatgcagg aagaaagcaa gggaacacaa 3180
ggcgggaagc aagacagaca acctggaaga aaactctctg gcgagaagaa acgagtcgag 3240
acctcccaca cagaaccggc gggggctgcg ggcctcccgt cgacggctgg gatacgccaa 3300
aaagctcctt ccggtcaccg gacatccgct gacgaggccc tcaaaccccg ccgcgctgtt 3360
tcatcttcgg cgctggcgtc tcctttgagc tccatgtccc ctacaggtcc ggcagcacag 3420
tctcctttgc cggcttctag cagaggcacg acaagcgcga agccgcccgt gggggccccc 3480
atgtctgtct ctgcgcctcg gccgaagctc gtgagcgaca aagaccttcg agcgaccttg 3540
gaagacaccg agaaagccgt gagcgcatct acaccccgtg gcgcaggggg cgcggggccg 3600
gagcgcgaga cagacgctgc gtgccgcgcg agtgctgcct gcggagaggc tgaaaaggtt 3660
tcgtctgacg agcaaagaga cggagcgaag gcgctcggga agggcgggaa gaaggccgaa 3720
gtgaagacga atgcgcgtgg aaaagaagca aagacagcag acgggggcga ggcggagggc 3780
tctggaaaga cccaggaaaa gagagagaga tctgcactga ggccgacaga aaggcctggc 3840
aaagtgccgg agacccaagg agaggaaggc gagcgggggga ctctgagcgg aggccgagaa 3900
gaagaaggag aagcacttgc atcttttaca gaagaggaaa aaaagaatca gtctcaagaa 3960
ccttccgccg cggggctgcg cttcctgtgc cagtgcgaac agggcgacag cgctaccgag 4020
gagcaagagg aagatgaagt tcgagccatg gatgccatgt acaccccggt gaagattctg 4080
caacctgggt ttctctccgc gacctttctc gctgagctcc acgaccctct gctggacttc 4140
tgtccgccgt cgcctcacgc gccggcgctc ccggaccgcg acagggggag cgcggagcca 4200
gcggggtcga cggacgacct actgcttgcc ctgccagcgg acttcctctc tggaaagaac 4260
cagtctgtgt cgcctgtgtt gacgcggcgg ctctcacgcg ctggcgtcgc ggatcagggc 4320
gcgccgcacc cgaaggcgga gactccagag gtttttaatc tgcgagcctg cccgtggctg 4380
ctcagactca gtgtgtctgg gtgcggcttc tgcgcccttt ctggggaaga gagcgaggaa 4440
gaagagacag aggagaacga cgcgaaaggc gagaaggagt cccgaaactg cgcgtcgcct 4500
tcacgctcgt ctccagagct ctcgcagtcg cctcgcccag gtgccctcaa tgctgctgcc 4560
ggcgcgtccc cctccacgga gcccccctgcg tctgccgtct tggacaaaga acaaacgcat 4620
gcttcttgga cagatccgat tccgactcgg gagcctttct tgcactcgtc gccgtccacc 4680

-continued

```
acagctgaca tcttcccct cgacgcccaa ggatcgtctg ggcgtctgtc tccttcctcg   4740
actctcacgc cctccggccc cgtttccgcg ccgagcaggt ctcctgtctc ctcgccctcg   4800
cccgatggga ccgcgacgca ggagacgcga gacgccgggg caacagcaga ggccgccctc   4860
tctcagcggt gtcagctgtg ctcgggggag tgcgacgtgg agtgtgtacg ctatttattt   4920
cgagttctga gtgaaactca gcgggcgttc ttcgcagtcg tcgatgtgct cctgcccaga   4980
aattaccccg caggcccgcc gtacgttgca gtgggtctct ctcacgccgt cccccgaacg   5040
gaagtccaga ggcttctgcg cgacttgaga gaagagttcg aggcctccaa aggcgaggtt   5100
gtcttgtacc gactctgtct ccaactccag tcgttcatgg cggagctgtc gagcacctct   5160
tgcttcagca atttgtggga ggaaatgcat ttcaaggagc gtcagagacg gcacttgctg   5220
ctgcgcgagc agcatatgat tcaccagagt ctgaaggctc ggcaaggcct tctgtcgcat   5280
ccgttcgggc atttggccgg gcgcctcaac gacgagcgac gagccgctcc cctcgggtct   5340
tcagagacgc gccacagcta ccgcccatcg ctgcagtact cccggagtgt cgcctgggcc   5400
gccgacgacg aggcttcgtt ttactgggag gacgaggacg acgaagaggt ttctgacttc   5460
cttgatctcg aagaggacta tgtcgatatt cagtcgagct tctacgcctc gccctcgaac   5520
tcgcggagac gggcctcgca ccggcgctgg atctctcaat ttcggcgctg ccgctcggct   5580
gtcacgtcgc agccgtctcc gatctccggc gccttcggcc tcgaggtgga gccccagaaa   5640
aaatcagagg gcccgccgag tcccgcgcgc gactccgagg tcccagcggc ctcgcaggcg   5700
ctctcaggcg tcgtcgcagg ggcgcgcgcc gccccagtgg gcgctgtgcc agacgaaaag   5760
ggaggcggag acagcgaacc gggggtgctc gagaaagaaa gtgcgcaagc gctgtcgggg   5820
caggcgggcg ttccctcgtc cccgctcgcc ggcaaaacgc cggaggcgaa gaaacagagc   5880
gacagcggtg ctggagccca agccggttcg ggcgcgctgg gctgcacggg tgcccgtgac   5940
ggcgccgcgg ctggcgacgc ggagacaacg gcgcccccga gcggcctctc cgagagcctc   6000
tgcgtcgcgg gggcggcggg ccgagaggaa aggcgccgcg gggcagggag tttccgatcg   6060
cttctcctca gctcacaaag gacgacgaga taccaaagag atttcattca actcgaggta   6120
ctgggcagcc gcgagcggta ccgcattgct ctcgtttacc acatcatcga caagcacaag   6180
tacatcgtga agcaaatctt cattccctgc ggtccagtgt ctctgttggc ccgtctctcg   6240
ccaggcacag aagctggacg gagacgcaag caacttcagg gcctcgaact cgttgaaagc   6300
gctcttcgtc aagtgacgct cctctgtgct cttcaacatc cctacatcat gcggtaccac   6360
caagcgtgga cgcagtacca caccgccgct gcgctcgccg ccaccagcgg cgaaggcggg   6420
gacccccccca acgcgatgcc tctgtcggat ctaggcgacg cgccagagag cggcgaggag   6480
ccttgcattg gagtgtacgt acagatggag ttctgcgagc gcagtctcga agacgaaatc   6540
gagaaacgca cagtgctgca ctgggactct cagcaaatct ggacgctgtt tcgacagacg   6600
ctggaagctc tggtgtacat acaccgcaac cgggtgtgtc acctgtctct gaagccgtcg   6660
aacgtatttc ttgagcctga cgcttacggc tacaatgtca agctgggcga cttcggcatc   6720
acttcacttt tttcgattgt tcacaacgtg cactcgccca tttcgcgact ctacacggcg   6780
ccggaactcc tcggcgcagc ggacaggaaa ttcgcttctc tgacgatgcg cgacgcagac   6840
aaggcagaca tgtactctct cggcgtcctc tttgcggaga tgtggggtcg acacgaaatg   6900
ttcggacgct cctgcagtcg gatcgagttt ttaacttctc tcgtgaaaga acggaatctg   6960
cagcagctga acgttccttc agcggccgtc aaaatcatca agcacctgct gtctccgaat   7020
cctggagatc gtccttcgtc aatgactttg ctgcagtctt cgctgcttcc accagctgtc   7080
```

-continued

```
gaggaggatc tgttcaaagc ctttcttctt cggctgcgta cgcaggtcca gagtcgctct   7140

gcgacaccgc ctcttcggga ctcttcgctc tcgcctgcga gcagaaagaa aacagatccg   7200

cggaaaaaaa atctggacaa aggccgaagt tctctcgctt ccaccgctca gactgaaggc   7260

ctgcaatccc acactccaca cggagccccg ggcctggcag gcgaagtcct caaaatcttt   7320

tttcgtcgac aattcgattc tgcatctgcg actctcttct ttagtgattt ccttagaaga   7380

tccagcacgg cgcccgagcc tgaaatgcgg tgtctcgtac aacggtccct tgccgacttc   7440

tttgctcgat gcggcgcaga cgaaattcaa atccctctcc ttgttcccct gacgaaaggc   7500

ctggcgaaat gtgaagaggc cttgaaacac tcaccgacgt atgcgtcgat tcctctctcc   7560

gagtctctgt ctctgctgga ccacagaaat gtacttctga ctctcccgcg gttcttcacc   7620

tctgcgctct gtgcctgcgg agacgcgggc gccttgccag actctctcca ctctgcgtcg   7680

ctcgcgccat ctccggaggc ggctctccag gcgctgctgt ctcctgtctc ctcgcgcctg   7740

tcgacctgtc ccttctgtgg ggaactgtct ccttcggctt ccgtgtctcc tcgctcgtcg   7800

ctctcgtccg cctcctgctt tgcccatgct gcgctcctct cggcgcctgt gggcagagct   7860

tacgctgggc tcctcgaaga ctcagagaga ggaaaagaga aaacagaaga ctctgaaatt   7920

tcgagtgcag gatgcgaata ccgacgcttc tgcgtgggcc attgttacac agctccaacg   7980

gtctcgttcc tcgcgagcta cggtcaccct cttccatact tttccgcctg ctaccagctt   8040

ctcttccctg ctggccccga gccgccttgt ccctcctcaa catccccgct ctgtcgcaaa   8100

tccagtaagc ctgccgctgc gacggaggca tctcctcctt ctcttcccca ctcttcttct   8160

cctttctcgc cgtcgtcaca tctcgcgctc tcggcggagg agcagcggac agctctttta   8220

gaggctgaag ttctgtcggt ctgcggaggc gcgatgagga ctgtgcaagc gagtctcggc   8280

ctcgctcttg gctggcgagt ctcttggtct ctcggcagcc tcttgcctgc aattctcaga   8340

gaatctttct tggtcccgct ctcagagctg ccgcatgcaa tggcgctgct ccggcaagtg   8400

cgaccgtcgg agacgggcca agtgccaaga gacgcccttc agaaggctgt ggagagactc   8460

ctcgatgttc actctcgcct ccaccgacgc atgcagagcg acgcggtcct ctccagactg   8520

tgtctgcttc tcgcccaccg acctctcgcg cctcgtcctc ttctgctgca gctcctctcc   8580

tcttcgtcgc tcgctctcgg cggcgcatgc cagccgggag gtgaccgggg cagagacgcc   8640

gaaaggcgcg tagagacagg tcactcgcag ggaacagaag ggcaagacaa gggaggcagc   8700

gctgccgagc agtcgctggc cgacgccttc ctcgcaggcg aggtggggag acatctgatg   8760

agagctctct acatcgagag gagtctggcg aagacggagg aagagtgccg gaacttcctc   8820

tttcgcgtct tcctcccagg cgacttcaga tccttcgatc ccatgggtct gctcttccaa   8880

gcctccgtcg gaacgtcctg ccccgacaag tcttcctctt cttcctcttc ctcttcttcc   8940

tcgtcttctt cttcctcttc tcccttcgaa gggattcctg ttggagacgg ggggactttg   9000

ttagcgtggg cgtggagtgg tgaggagcct cgcggcggcc gagtgtatcg gcaggcctct   9060

tctgtttcgt ttccttctct ctctgctctg agtcaccggt cggcgagtgt ctcgctgagg   9120

cgacgggaag agaagctctc ttcgtctccc gccgtctctc cagccgcact ccagacgctg   9180

agcttcgaac tggctctcga gcgcgtcctc tccttctctt ccctcctgag acgtctccgc   9240

gaaaatcctg ctctttgtca gttcggcgca ggcccgctgc ctctcccttc gttcgtcttg   9300

ccgctggtgt tctctgcaga agcgaacgcg gcggcgctgc gcctggccac tgccctcgtc   9360

aaacagacag cgcctcccgc cgacgagaca gagtcgttct tcggagccgg aggggacggc   9420
```

```
gcgaacagcg cgtctgagct cggagacgtc gcagcgctcg actactcact tccccaggtc   9480

gtcgtcacgg cgcagagcgc aaagcaactt ccgctcggct tttctctcgt ctgcagactt   9540

ctccgaaggg gcattcgcgc tgagcttcgc gtcactccgg tggttgagac ttcttacttc   9600

cagcgcttgc ttcgtcgttc gcgccgcatt ctctaccacg ttcaaatcca gcatcaccgc   9660

gcgtccgtcg ctgcccatgc gacgctgacg gtctccccgg agtcgtgcgt ctctgcgctc   9720

gccagcggtg cctcgtatgc ctctctcctc accctgacg cgctgcccgc ggcgctctcc   9780

ttcctcccag gcggcgcgcc caccagcggc gttctaagca gccgagaagc cgcggcgtct   9840

ctgctgcggg gcgagcacag cgcccaggga tttgccgcgt ctttcaaggc gagggaggag   9900

gcgtccctgc cttcctccgc gccccagagc ggcgccgcgg ccgcggggat cggcggacct   9960

gctggtcctg gaggagcggc ctttgccggc cctccccaca atttcctggt gccgggcgcg  10020

ggtggcgccc agagtctccg aaccgccgct ggaggggcct gtctcccctc gctcgcctcg  10080

ctgcccgccg cgtacgtcat tgaggcgctg catgcgggtg ctggcggcgc gcgagacctt  10140

gcgtcggcgt ttttccccga gcgcaagaaa cagaaagtct tcagtgaggc tgcggcgatt  10200

cacctcctct gctccgccct tgtcgaaggc tacgaaggcg agaaaggaag cggcggcaga  10260

aaaaccaaga agggaggcgc agccgagcgc ggagagtccg actgtgcaaa gccaggcaga  10320

ggtggaagag accgacgctg aacgcagcgc agtgcagtga aggaaaacgc ttcaaacgga  10380

gaggctcggc atgcgagggc cgcgaggaga gaggagatga gacaccgaga agaaatcgcg  10440

agacagagcg acaacaggaa gcagcatctc gaagggagag agagacgaga gaggacgcag  10500

caagcagaag gaaccaggag gagagagagg gagcaacgag gaggaagcga gagtgatgtt  10560

gagagagaag cctgtcgcac tctctctctc ctattgatgc acttcccgcg cctgttccct  10620

ccggtgattc ttctctcttc tgcggtctgt cggccgcatt ggcattcgac tggaaacatg  10680

gggtggacgc ttgcggcggt ggcttctgtc ggtctgtgag cccccgcgtt tttctctgca  10740

caggcgaccg tcccctctct gttcctctgc cgctgtctcg gcggctcgcc tcctcttctg  10800

cggtcgcctt cggcgccttg tgaacagagt tgcttggctg tgcatttctg tcgcgcgttt  10860

ctctccgtcc cttcctgtga gaaaagatct ccccaacgaa gaattatgct ggtgttcaca  10920

tgttttttat cgagacgcca ctgagcgtct tccggtctga aaggttctgt gcgtcctcgc  10980

tgcatgcttc tttgtctcag ttcttccagc ttcagttctt cctgtcaccc caacgcacca  11040

caggcgtctt cagttttttg ttcgcttgtc ttgaagtctc tccttttttc gacctttga   11100

ggctcgggac tccgtttcag cctcacactt cctcgttttt tcggtttttt gtttcgggat  11160

gcccccgcga gacgccagcg tagatgtctc gcgacagtgt ggctttgtct ttgcggcttc  11220

tccgtttttc ttgtcctcgt tagagcggcg cgcgttcccc gttcttccaa tctccctaag  11280

tgatcgcaga actgcttcca gacgcttgac tccagagact ctttcgcaac gctccccatt  11340

gaaaaaaaaa aaaaaaaaa a                                             11361
```

<210> SEQ ID NO 14
<211> LENGTH: 404
<212> TYPE: PRT
<213> ORGANISM: Toxoplasma gondii
<220> FEATURE:
<221> NAME/KEY: MISC_FEATURE
<223> OTHER INFORMATION: X represents amino acid locations having low or
      no homology to other poly peptides listed herein
<220> FEATURE:
<221> NAME/KEY: misc_feature
<222> LOCATION: (31)..(34)
<223> OTHER INFORMATION: Xaa can be any naturally occurring amino acid
<220> FEATURE:
<221> NAME/KEY: misc_feature
<222> LOCATION: (48)..(72)
<223> OTHER INFORMATION: Xaa can be any naturally occurring amino acid
<220> FEATURE:
<221> NAME/KEY: misc_feature
<222> LOCATION: (101)..(139)
<223> OTHER INFORMATION: Xaa can be any naturally occurring amino acid
<220> FEATURE:
<221> NAME/KEY: misc_feature
<222> LOCATION: (150)..(151)
<223> OTHER INFORMATION: Xaa can be any naturally occurring amino acid
<220> FEATURE:
<221> NAME/KEY: misc_feature
<222> LOCATION: (164)..(180)
<223> OTHER INFORMATION: Xaa can be any naturally occurring amino acid
<220> FEATURE:
<221> NAME/KEY: misc_feature
<222> LOCATION: (227)..(231)
<223> OTHER INFORMATION: Xaa can be any naturally occurring amino acid
<220> FEATURE:
<221> NAME/KEY: misc_feature
<222> LOCATION: (247)..(276)
<223> OTHER INFORMATION: Xaa can be any naturally occurring amino acid
<220> FEATURE:
<221> NAME/KEY: misc_feature
<222> LOCATION: (294)..(294)
<223> OTHER INFORMATION: Xaa can be any naturally occurring amino acid
<220> FEATURE:
<221> NAME/KEY: misc_feature
<222> LOCATION: (352)..(362)
<223> OTHER INFORMATION: Xaa can be any naturally occurring amino acid

<400> SEQUENCE: 14

Arg Tyr Gln Arg Asp Phe Ile Gln Leu Glu Val Leu Gly Ser Arg Glu
1 5 10 15

Arg Tyr Arg Ile Ala Leu Val Tyr His Ile Ile Asp Lys His Xaa Xaa
20 25 30

Xaa Xaa Lys Tyr Ile Val Lys Gln Ile Phe Ile Pro Cys Gly Pro Xaa
35 40 45

Xaa Xaa Xaa Xaa Xaa Xaa Xaa Xaa Xaa Xaa Xaa Xaa Xaa Xaa Xaa Xaa
50 55 60

Xaa Xaa Xaa Xaa Xaa Xaa Xaa Xaa Val Glu Ser Ala Leu Arg Gln Val
65 70 75 80

Thr Leu Leu Cys Ala Leu Gln His Pro Tyr Ile Met Arg Tyr His Gln
85 90 95

Ala Trp Thr Gln Xaa Xaa Xaa Xaa Xaa Xaa Xaa Xaa Xaa Xaa Xaa Xaa
100 105 110

Xaa Xaa Xaa Xaa Xaa Xaa Xaa Xaa Xaa Xaa Xaa Xaa Xaa Xaa Xaa Xaa
115 120 125

Xaa Xaa Xaa Xaa Xaa Xaa Xaa Xaa Xaa Xaa Xaa Val Tyr Val Gln Met
130 135 140

Glu Phe Cys Glu Arg Xaa Xaa Ser Leu Glu Asp Glu Ile Glu Lys Arg
145 150 155 160

Thr Val Leu Xaa Xaa Xaa Xaa Xaa Xaa Xaa Xaa Xaa Xaa Xaa Xaa Xaa
165 170 175

Xaa Xaa Xaa Xaa His Trp Asp Ser Gln Gln Ile Trp Thr Leu Phe Arg
180 185 190

Gln Thr Leu Glu Ala Leu Val Tyr Ile His Arg Asn Arg Val Cys His
195 200 205

Leu Ser Leu Lys Pro Ser Asn Val Phe Leu Glu Pro Asp Ala Tyr Gly
210 215 220

Tyr Asn Xaa Xaa Xaa Xaa Xaa Val Lys Leu Gly Asp Phe Gly Ile Thr
225 230 235 240

```
Ser Leu Phe Ser Ile Val Xaa Xaa Xaa Xaa Xaa Xaa Xaa Xaa Xaa Xaa
                245                 250                 255

Xaa Xaa Xaa Xaa Xaa Xaa Xaa Xaa Xaa Xaa Xaa Xaa Xaa Xaa Xaa Xaa
            260                 265                 270

Xaa Xaa Xaa Xaa His Asn Val His Ser Pro Ile Ser Arg Leu Tyr Thr
        275                 280                 285

Ala Pro Glu Leu Leu Xaa Gly Ala Ala Asp Arg Lys Phe Ala Ser Leu
    290                 295                 300

Thr Met Arg Asp Ala Asp Lys Ala Asp Met Tyr Ser Leu Gly Val Leu
305                 310                 315                 320

Phe Ala Glu Met Trp Gly Arg His Glu Met Phe Gly Arg Ser Cys Ser
                325                 330                 335

Arg Ile Glu Phe Leu Thr Ser Leu Val Lys Glu Arg Asn Leu Gln Xaa
            340                 345                 350

Xaa Xaa Xaa Xaa Xaa Xaa Xaa Xaa Xaa Xaa Gln Leu Asn Val Pro Ser
        355                 360                 365

Ala Ala Val Lys Ile Ile Lys His Leu Leu Ser Pro Asn Pro Gly Asp
    370                 375                 380

Arg Pro Ser Ser Met Thr Leu Leu Gln Ser Ser Leu Leu Pro Pro Ala
385                 390                 395                 400

Val Glu Glu Asp


<210> SEQ ID NO 15
<211> LENGTH: 707
<212> TYPE: PRT
<213> ORGANISM: Toxoplasma gondii
<220> FEATURE:
<221> NAME/KEY: MISC_FEATURE
<223> OTHER INFORMATION: X represents amino acid locations having low or
      no homology to other poly peptides listed herein
<220> FEATURE:
<221> NAME/KEY: misc_feature
<222> LOCATION: (31)..(34)
<223> OTHER INFORMATION: Xaa can be any naturally occurring amino acid
<220> FEATURE:
<221> NAME/KEY: misc_feature
<222> LOCATION: (48)..(152)
<223> OTHER INFORMATION: Xaa can be any naturally occurring amino acid
<220> FEATURE:
<221> NAME/KEY: misc_feature
<222> LOCATION: (181)..(204)
<223> OTHER INFORMATION: Xaa can be any naturally occurring amino acid
<220> FEATURE:
<221> NAME/KEY: misc_feature
<222> LOCATION: (214)..(214)
<223> OTHER INFORMATION: Xaa can be any naturally occurring amino acid
<220> FEATURE:
<221> NAME/KEY: misc_feature
<222> LOCATION: (242)..(339)
<223> OTHER INFORMATION: Xaa can be any naturally occurring amino acid
<220> FEATURE:
<221> NAME/KEY: misc_feature
<222> LOCATION: (386)..(390)
<223> OTHER INFORMATION: Xaa can be any naturally occurring amino acid
<220> FEATURE:
<221> NAME/KEY: misc_feature
<222> LOCATION: (416)..(473)
<223> OTHER INFORMATION: Xaa can be any naturally occurring amino acid
<220> FEATURE:
<221> NAME/KEY: misc_feature
<222> LOCATION: (511)..(520)
<223> OTHER INFORMATION: Xaa can be any naturally occurring amino acid
<220> FEATURE:
<221> NAME/KEY: misc_feature
<222> LOCATION: (541)..(542)
<223> OTHER INFORMATION: Xaa can be any naturally occurring amino acid
<220> FEATURE:
```

<221> NAME/KEY: misc_feature
<222> LOCATION: (573)..(666)
<223> OTHER INFORMATION: Xaa can be any naturally occurring amino acid

<400> SEQUENCE: 15

```
Arg Tyr His Thr Glu Phe Ile Glu Leu Gln Gln Leu Gly Ser Gly Gly
1               5                   10                  15

Phe Gly Ser Val Thr Lys Val Arg Gln Arg Gln Gly Gly Gly Xaa Xaa
            20                  25                  30

Xaa Xaa Ile Phe Ala Val Lys Cys Ile Pro Leu Arg Pro Ala Arg Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Ala Val Gly Tyr Met Glu Glu Ala
145                 150                 155                 160

Thr Met Leu Ala Lys Leu Asn His Lys His Ile Val Arg Tyr Tyr Asp
                165                 170                 175

Ala Trp Leu Glu Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Leu Phe Ile Leu
        195                 200                 205

Met Glu Tyr Cys Pro Xaa Gly Arg Thr Leu Arg Glu Ala Ile Asp Ser
    210                 215                 220

Gly Leu Leu Gln Leu Pro Pro Ala Ser Phe Arg Gln Thr Leu Arg Arg
225                 230                 235                 240

Arg Xaa Xaa Xaa Xaa Xaa Xaa Xaa Xaa Xaa Xaa Xaa Xaa Xaa Xaa Xaa
                245                 250                 255

Xaa Xaa Xaa Xaa Xaa Xaa Xaa Xaa Xaa Xaa Xaa Xaa Xaa Xaa Xaa Xaa
            260                 265                 270

Xaa Xaa Xaa Xaa Xaa Xaa Xaa Xaa Xaa Xaa Xaa Xaa Xaa Xaa Xaa Xaa
        275                 280                 285

Xaa Xaa Xaa Xaa Xaa Xaa Xaa Xaa Xaa Xaa Xaa Xaa Xaa Xaa Xaa Xaa
    290                 295                 300

Xaa Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Xaa Xaa Xaa Xaa Xaa Xaa Xaa Xaa
                325                 330                 335

Xaa Xaa Xaa Met Gly Leu Arg Ala Leu Lys Trp Arg Leu Thr Arg Asp
            340                 345                 350

Leu Val Gly Gly Val Ala Tyr Met His Ser Phe Gly Val Ile His Arg
        355                 360                 365

Asp Leu Lys Pro Ser Asn Ile Phe Leu Lys Val Asp Gln Asp Arg Leu
    370                 375                 380

Cys Xaa Xaa Xaa Xaa Xaa Val Lys Ile Gly Asp Phe Gly Leu Thr Thr
```

-continued

```
385                 390                 395                 400

Thr Val Leu Lys Gly Lys Pro Gly Gly Ser Gln Ala Ala Gly Arg Xaa
                405                 410                 415

Xaa Xaa Xaa Xaa Xaa Xaa Xaa Xaa Xaa Xaa Xaa Xaa Xaa Xaa Xaa Xaa
            420                 425                 430

Xaa Xaa Xaa Xaa Xaa Xaa Xaa Xaa Xaa Xaa Xaa Xaa Xaa Xaa Xaa Xaa
        435                 440                 445

Xaa Xaa Xaa Xaa Xaa Xaa Xaa Xaa Xaa Xaa Xaa Xaa Xaa Xaa Xaa Xaa
    450                 455                 460

Xaa Xaa Xaa Xaa Xaa Xaa Xaa Xaa Xaa Pro Leu Ser Ser Phe Pro Gly
465                 470                 475                 480

Ser His Pro Ser Asp Thr Pro Ser Leu Arg Leu Ser Ala Gly Val Gly
                485                 490                 495

Thr Val Tyr Tyr Met Ala Pro Glu Gln Ala Thr Gly Ser Arg Xaa Xaa
            500                 505                 510

Xaa Xaa Xaa Xaa Xaa Xaa Xaa Xaa Tyr Asp Gln Lys Ala Asp Ile Phe
        515                 520                 525

Ser Leu Gly Val Val Leu Phe Glu Met Trp Ala Pro Xaa Xaa Pro Phe
    530                 535                 540

Thr Thr Ala Met Glu Arg Ala Ser Val Leu Gly Gln Leu Thr Leu Asp
545                 550                 555                 560

His Glu Gln Gln Met Arg Arg Leu Leu Pro Arg Gln Xaa Xaa Xaa Xaa
                565                 570                 575

Xaa Xaa Xaa Xaa Xaa Xaa Xaa Xaa Xaa Xaa Xaa Xaa Xaa Xaa Xaa Xaa
            580                 585                 590

Xaa Xaa Xaa Xaa Xaa Xaa Xaa Xaa Xaa Xaa Xaa Xaa Xaa Xaa Xaa Xaa
        595                 600                 605

Xaa Xaa Xaa Xaa Xaa Xaa Xaa Xaa Xaa Xaa Xaa Xaa Xaa Xaa Xaa Xaa
    610                 615                 620

Xaa Xaa Xaa Xaa Xaa Xaa Xaa Xaa Xaa Xaa Xaa Xaa Xaa Xaa Xaa Xaa
625                 630                 635                 640

Xaa Xaa Xaa Xaa Xaa Xaa Xaa Xaa Xaa Xaa Xaa Xaa Xaa Xaa Xaa Xaa
                645                 650                 655

Xaa Xaa Xaa Xaa Xaa Xaa Xaa Xaa Xaa Xaa Gln Tyr Val Pro Ser Glu
            660                 665                 670

Val Ala Pro Leu Ile Leu Ala Met Ile Gln Gln Asp Pro Ala Ser Arg
        675                 680                 685

Pro Ala Ala Asp Ala Leu Leu Val Asp Asp Val Leu Leu Pro Leu Glu
    690                 695                 700

Leu Ser Gln
705


<210> SEQ ID NO 16
<211> LENGTH: 409
<212> TYPE: PRT
<213> ORGANISM: Toxoplasma gondii
<220> FEATURE:
<221> NAME/KEY: MISC_FEATURE
<223> OTHER INFORMATION: Xaa represents amino acid locations having low
      or no homology to other poly peptides listed herein
<220> FEATURE:
<221> NAME/KEY: MISC_FEATURE
<223> OTHER INFORMATION: X represents amino acid locations having low or
      no homology to other poly peptides listed herein
<220> FEATURE:
<221> NAME/KEY: misc_feature
<222> LOCATION: (31)..(34)
<223> OTHER INFORMATION: Xaa can be any naturally occurring amino acid
```

```
<220> FEATURE:
<221> NAME/KEY: misc_feature
<222> LOCATION: (48)..(73)
<223> OTHER INFORMATION: Xaa can be any naturally occurring amino acid
<220> FEATURE:
<221> NAME/KEY: misc_feature
<222> LOCATION: (102)..(144)
<223> OTHER INFORMATION: Xaa can be any naturally occurring amino acid
<220> FEATURE:
<221> NAME/KEY: misc_feature
<222> LOCATION: (155)..(156)
<223> OTHER INFORMATION: Xaa can be any naturally occurring amino acid
<220> FEATURE:
<221> NAME/KEY: misc_feature
<222> LOCATION: (167)..(185)
<223> OTHER INFORMATION: Xaa can be any naturally occurring amino acid
<220> FEATURE:
<221> NAME/KEY: misc_feature
<222> LOCATION: (232)..(236)
<223> OTHER INFORMATION: Xaa can be any naturally occurring amino acid
<220> FEATURE:
<221> NAME/KEY: misc_feature
<222> LOCATION: (252)..(281)
<223> OTHER INFORMATION: Xaa can be any naturally occurring amino acid
<220> FEATURE:
<221> NAME/KEY: misc_feature
<222> LOCATION: (299)..(299)
<223> OTHER INFORMATION: Xaa can be any naturally occurring amino acid
<220> FEATURE:
<221> NAME/KEY: misc_feature
<222> LOCATION: (357)..(367)
<223> OTHER INFORMATION: Xaa can be any naturally occurring amino acid

<400> SEQUENCE: 16

Arg Tyr Gln Arg Asp Phe Ile Gln Leu Glu Val Leu Gly Val Arg Asp
1               5                   10                  15

His Tyr Arg Ile Ala Leu Val Tyr His Ile Ile Asp Lys His Xaa Xaa
            20                  25                  30

Xaa Xaa Lys Tyr Ile Val Lys Gln Val Phe Ile Pro Cys Gly Pro Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Val Glu Ser Ala Leu Gln Gln
65                  70                  75                  80

Val Thr Leu Leu Cys Ala Leu Gln His Pro Tyr Ile Met Arg Tyr His
                85                  90                  95

Gln Ala Trp Thr Gln Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa Xaa
    130                 135                 140

Val Tyr Ile Gln Met Glu Phe Cys Glu Arg Xaa Xaa Ser Leu Glu Asp
145                 150                 155                 160

Glu Ile Glu Lys Arg Thr Xaa Xaa Xaa Xaa Xaa Xaa Xaa Xaa Xaa Xaa
                165                 170                 175

Xaa Xaa Xaa Xaa Xaa Xaa Xaa Xaa Xaa His Trp Asp Ser Gln Gln Ile
            180                 185                 190

Trp Thr Leu Phe Arg Gln Thr Leu Glu Ala Leu Val Tyr Ile His Arg
        195                 200                 205

Asn Arg Val Cys His Val Ser Leu Lys Pro Ser Asn Val Phe Leu Glu
    210                 215                 220

Pro Asp Ala Tyr Gly Tyr Asn Xaa Xaa Xaa Xaa Xaa Val Lys Leu Gly
225                 230                 235                 240
```

```
Asp Phe Gly Val Thr Ser Leu Phe Asp Ile Val Xaa Xaa Xaa Xaa Xaa
                245                 250                 255

Xaa Xaa Xaa Xaa Xaa Xaa Xaa Xaa Xaa Xaa Xaa Xaa Xaa Xaa Xaa Xaa
            260                 265                 270

Xaa Xaa Xaa Xaa Xaa Xaa Xaa Xaa Xaa His Asn Thr His Ser Pro Ile
        275                 280                 285

Ser Arg Leu Tyr Thr Ala Pro Glu Leu Leu Xaa Ser Thr Ala Asp Gly
    290                 295                 300

Lys Ser Ser Ser Leu Thr Met Arg Asp Ala Asp Lys Ala Asp Met Tyr
305                 310                 315                 320

Ser Leu Gly Val Leu Phe Ala Glu Met Trp Gly Arg His Glu Met Phe
                325                 330                 335

Gly Arg Ser Cys Ser Arg Thr Glu Phe Leu Thr Ser Leu Val Lys Glu
            340                 345                 350

Arg Asn Leu Gln Xaa Xaa Xaa Xaa Xaa Xaa Xaa Xaa Xaa Xaa Xaa Gln
        355                 360                 365

Leu Asn Val Pro Ser Ala Ala Val Lys Ile Ile Lys Gln Leu Leu Ser
    370                 375                 380

Pro Asn Pro Ala Asp Arg Pro Ser Ser Met Thr Leu Leu Pro Pro Ala
385                 390                 395                 400

Val Glu Glu Glu Leu Phe Lys Ala Phe
                405


<210> SEQ ID NO 17
<211> LENGTH: 455
<212> TYPE: PRT
<213> ORGANISM: Toxoplasma gondii
<220> FEATURE:
<221> NAME/KEY: MISC_FEATURE
<223> OTHER INFORMATION: X represents amino acid locations having low or
      no homology to other poly peptides listed herein
<220> FEATURE:
<221> NAME/KEY: misc_feature
<222> LOCATION: (31)..(34)
<223> OTHER INFORMATION: Xaa can be any naturally occurring amino acid
<220> FEATURE:
<221> NAME/KEY: misc_feature
<222> LOCATION: (48)..(62)
<223> OTHER INFORMATION: Xaa can be any naturally occurring amino acid
<220> FEATURE:
<221> NAME/KEY: misc_feature
<222> LOCATION: (91)..(190)
<223> OTHER INFORMATION: Xaa can be any naturally occurring amino acid
<220> FEATURE:
<221> NAME/KEY: misc_feature
<222> LOCATION: (200)..(200)
<223> OTHER INFORMATION: Xaa can be any naturally occurring amino acid
<220> FEATURE:
<221> NAME/KEY: misc_feature
<222> LOCATION: (214)..(231)
<223> OTHER INFORMATION: Xaa can be any naturally occurring amino acid
<220> FEATURE:
<221> NAME/KEY: misc_feature
<222> LOCATION: (278)..(282)
<223> OTHER INFORMATION: Xaa can be any naturally occurring amino acid
<220> FEATURE:
<221> NAME/KEY: misc_feature
<222> LOCATION: (296)..(325)
<223> OTHER INFORMATION: Xaa can be any naturally occurring amino acid
<220> FEATURE:
<221> NAME/KEY: misc_feature
<222> LOCATION: (349)..(358)
<223> OTHER INFORMATION: Xaa can be any naturally occurring amino acid
<220> FEATURE:
<221> NAME/KEY: misc_feature
<222> LOCATION: (379)..(380)
<223> OTHER INFORMATION: Xaa can be any naturally occurring amino acid
```

```
<220> FEATURE:
<221> NAME/KEY: misc_feature
<222> LOCATION: (405)..(415)
<223> OTHER INFORMATION: Xaa can be any naturally occurring amino acid

<400> SEQUENCE: 17

Arg Tyr Tyr Arg Asp Phe Phe Glu Glu Lys Ile Leu Gly Cys Gly Gly
1               5                   10                  15

Phe Gly Tyr Val Met Lys Val Lys Asn Lys Lys Phe Asn Ile Xaa Xaa
            20                  25                  30

Xaa Xaa Thr Tyr Ala Leu Lys Ile Ile Arg Leu Ser Asn Ser Lys Xaa
        35                  40                  45

Xaa Xaa Xaa Xaa Xaa Xaa Xaa Xaa Xaa Xaa Xaa Xaa Xaa Xaa Asn Ser
    50                  55                  60

Tyr Ile Met Glu Glu Ala Ile Met Ile Ala Lys Leu Gln His Glu Asn
65                  70                  75                  80

Ile Val Arg Tyr Tyr Asp Ala Trp Val Glu Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Leu Tyr
            180                 185                 190

Ile Leu Met Glu Tyr Cys Pro Xaa Gly Lys Thr Leu Arg Glu Ala Ile
        195                 200                 205

Asp Cys Gly Phe Ile Xaa Xaa Xaa Xaa Xaa Xaa Xaa Xaa Xaa Xaa Xaa
    210                 215                 220

Xaa Xaa Xaa Xaa Xaa Xaa Xaa Cys Arg Asn Glu Lys Leu Ile Trp Glu
225                 230                 235                 240

Leu Ile Lys Gln Ile Leu Lys Gly Ile Ser Tyr Ile His Asp Met Lys
                245                 250                 255

Ile Met His Arg Asp Ile Lys Pro Ser Asn Ile Phe Leu Gln Ile Thr
            260                 265                 270

Asp Asn Ile Leu Ile Xaa Xaa Xaa Xaa Xaa Ala Lys Ile Gly Asp Phe
        275                 280                 285

Gly Leu Thr Thr Arg Ile Gly Xaa Xaa Xaa Xaa Xaa Xaa Xaa Xaa Xaa
    290                 295                 300

Xaa Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Asp Thr Gln Ile Asn Pro Ser Ala Gly Thr Ile
                325                 330                 335

His Tyr Ile Ser Pro Glu Gln Leu Asn Gly Glu Pro Xaa Xaa Xaa Xaa
            340                 345                 350

Xaa Xaa Xaa Xaa Xaa Xaa Phe Asn Glu Lys Ala Asp Ile Phe Ser Leu
        355                 360                 365

Gly Val Val Phe Phe Glu Met Phe His Glu Xaa Xaa Pro Phe Ser Thr
    370                 375                 380
```

Ser Met Glu Arg Ser Ile Thr Leu Ser Asn Leu Leu Lys Gly Ile Tyr
385 390 395 400

Pro Glu Tyr Met Xaa Xaa Xaa Xaa Xaa Xaa Xaa Xaa Xaa Xaa Xaa Lys
405 410 415

Ala Asp Asn Lys Lys Phe Gln Phe Leu Ser Ser Leu Leu Ala Ile Asn
420 425 430

Pro Gln Glu Arg Cys Cys Ala Tyr Asn Leu Leu His Glu Ser Val Leu
435 440 445

Phe Thr Phe Glu Lys Asp Phe
450 455

<210> SEQ ID NO 18
<211> LENGTH: 750
<212> TYPE: PRT
<213> ORGANISM: Toxoplasma gondii
<220> FEATURE:
<221> NAME/KEY: MISC_FEATURE
<223> OTHER INFORMATION: X represents amino acid locations having low or no homology to other poly peptides listed herein
<220> FEATURE:
<221> NAME/KEY: misc_feature
<222> LOCATION: (31)..(45)
<223> OTHER INFORMATION: Xaa can be any naturally occurring amino acid
<220> FEATURE:
<221> NAME/KEY: misc_feature
<222> LOCATION: (59)..(89)
<223> OTHER INFORMATION: Xaa can be any naturally occurring amino acid
<220> FEATURE:
<221> NAME/KEY: misc_feature
<222> LOCATION: (118)..(399)
<223> OTHER INFORMATION: Xaa can be any naturally occurring amino acid
<220> FEATURE:
<221> NAME/KEY: misc_feature
<222> LOCATION: (409)..(409)
<223> OTHER INFORMATION: Xaa can be any naturally occurring amino acid
<220> FEATURE:
<221> NAME/KEY: misc_feature
<222> LOCATION: (423)..(440)
<223> OTHER INFORMATION: Xaa can be any naturally occurring amino acid
<220> FEATURE:
<221> NAME/KEY: misc_feature
<222> LOCATION: (487)..(491)
<223> OTHER INFORMATION: Xaa can be any naturally occurring amino acid
<220> FEATURE:
<221> NAME/KEY: misc_feature
<222> LOCATION: (517)..(554)
<223> OTHER INFORMATION: Xaa can be any naturally occurring amino acid
<220> FEATURE:
<221> NAME/KEY: misc_feature
<222> LOCATION: (595)..(650)
<223> OTHER INFORMATION: Xaa can be any naturally occurring amino acid
<220> FEATURE:
<221> NAME/KEY: misc_feature
<222> LOCATION: (674)..(675)
<223> OTHER INFORMATION: Xaa can be any naturally occurring amino acid
<220> FEATURE:
<221> NAME/KEY: misc_feature
<222> LOCATION: (704)..(711)
<223> OTHER INFORMATION: Xaa can be any naturally occurring amino acid

<400> SEQUENCE: 18

Ser Tyr Phe Leu Thr Phe Phe Phe Asn His Met Val Phe Cys Asn Arg
1 5 10 15

Asp Phe Asn Leu Phe Cys Asn Ile Leu Asn Asp Lys Lys Gly Xaa Xaa
20 25 30

Xaa Xaa Xaa Xaa Xaa Xaa Xaa Xaa Xaa Xaa Xaa Xaa Xaa Glu Tyr Ala
35 40 45

Asn Lys Asn Cys Val Ile Thr Gln Asn Lys Xaa Xaa Xaa Xaa Xaa Xaa
50 55 60

-continued

```
Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Ile Lys Lys Ile Ile Cys Glu
                85                  90                  95

Leu Ala Lys Leu Thr Lys Ile His His Lys Tyr Leu Ala Arg Tyr His
            100                 105                 110

Phe Ser Trp Phe Glu Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa Xaa
    210                 215                 220

Xaa Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa Xaa
                245                 250                 255

Xaa Xaa Xaa Xaa Xaa Xaa Xaa Xaa Xaa Xaa Xaa Xaa Xaa Xaa Xaa Xaa
            260                 265                 270

Xaa Xaa Xaa Xaa Xaa Xaa Xaa Xaa Xaa Xaa Xaa Xaa Xaa Xaa Xaa Xaa
        275                 280                 285

Xaa Xaa Xaa Xaa Xaa Xaa Xaa Xaa Xaa Xaa Xaa Xaa Xaa Xaa Xaa Xaa
    290                 295                 300

Xaa Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Xaa Xaa Xaa Xaa Xaa Xaa Xaa Xaa
                325                 330                 335

Xaa Xaa Xaa Xaa Xaa Xaa Xaa Xaa Xaa Xaa Xaa Xaa Xaa Xaa Xaa Xaa
            340                 345                 350

Xaa Xaa Xaa Xaa Xaa Xaa Xaa Xaa Xaa Xaa Xaa Xaa Xaa Xaa Xaa Xaa
        355                 360                 365

Xaa Xaa Xaa Xaa Xaa Xaa Xaa Xaa Xaa Xaa Xaa Xaa Xaa Xaa Xaa Xaa
    370                 375                 380

Xaa Xaa Xaa Xaa Xaa Xaa Xaa Xaa Xaa Xaa Xaa Xaa Xaa Xaa Xaa Leu
385                 390                 395                 400

Tyr Ile Gln Cys Glu His Cys Lys Xaa Gly Gln Ser Leu Glu Lys Glu
                405                 410                 415

Ile Glu Asn Asn Phe Phe Xaa Xaa Xaa Xaa Xaa Xaa Xaa Xaa Xaa Xaa
            420                 425                 430

Xaa Xaa Xaa Xaa Xaa Xaa Xaa Xaa Gln Lys Asn Lys Tyr Leu Ile Trp
        435                 440                 445

Asn Ile Phe Arg Gln Val Leu Glu Ser Leu Ser Tyr Leu His Lys Gln
    450                 455                 460

Lys Ile Tyr Ile Lys Asn Leu Asn Ser Gln Asn Ile Tyr Leu Asp Asn
465                 470                 475                 480

Asp Lys Tyr Gly Ala His Xaa Xaa Xaa Xaa Xaa Ile Lys Ile Ile Asn
```

-continued

```
                485                 490                 495

Tyr Ser Ile Cys Asn Met Ile Asp Tyr Phe Tyr Phe Tyr His Tyr Ser
            500                 505                 510

Tyr Lys Asn Asn Xaa Xaa Xaa Xaa Xaa Xaa Xaa Xaa Xaa Xaa Xaa Xaa
        515                 520                 525

Xaa Xaa Xaa Xaa Xaa Xaa Xaa Xaa Xaa Xaa Xaa Xaa Xaa Xaa Xaa Xaa
    530                 535                 540

Xaa Xaa Xaa Xaa Xaa Xaa Xaa Xaa Xaa Xaa Lys Glu Ser Lys Glu Glu
545                 550                 555                 560

Asp Ile Phe Val Lys Lys Cys Asn Ser Phe Glu Ile Lys Asn Asp Ser
                565                 570                 575

Ser Cys Lys Glu Tyr Ile Asn Asp Glu Lys Ile Asn Lys Glu Lys Asn
            580                 585                 590

Val Pro Xaa Xaa Xaa Xaa Xaa Xaa Xaa Xaa Xaa Xaa Xaa Xaa Xaa Xaa
        595                 600                 605

Xaa Xaa Xaa Xaa Xaa Xaa Xaa Xaa Xaa Xaa Xaa Xaa Xaa Xaa Xaa Xaa
    610                 615                 620

Xaa Xaa Xaa Xaa Xaa Xaa Xaa Xaa Xaa Xaa Xaa Xaa Xaa Xaa Xaa Xaa
625                 630                 635                 640

Xaa Xaa Xaa Xaa Xaa Xaa Xaa Xaa Xaa Xaa Lys Lys Tyr Asp Tyr Glu
                645                 650                 655

Glu Leu Asp Leu Phe Ser Leu Gly Leu Leu Leu Tyr Glu Leu Trp His
            660                 665                 670

Thr Xaa Xaa Pro Phe Lys Ser Lys Glu Glu Lys Leu Ile Asn Ile Thr
        675                 680                 685

Thr Met Ile Lys Glu Lys Thr Phe Ser Glu Ser Phe Ile Lys Asn Xaa
    690                 695                 700

Xaa Xaa Xaa Xaa Xaa Xaa Xaa Ile Asp Asn Asp Ser Leu Lys Val Leu
705                 710                 715                 720

Lys Phe Ile Leu Ile Ser Thr Ile Asn Tyr Asp Thr Asn Glu Lys Lys
                725                 730                 735

Ile Thr Lys Leu Glu Tyr Val Asp Ile Leu Asn Leu Asn Ile
            740                 745                 750
```

<210> SEQ ID NO 19
<211> LENGTH: 428
<212> TYPE: PRT
<213> ORGANISM: Toxoplasma gondii
<220> FEATURE:
<221> NAME/KEY: MISC_FEATURE
<223> OTHER INFORMATION: X represents amino acid locations having low or no homology to other poly peptides listed herein
<220> FEATURE:
<221> NAME/KEY: misc_feature
<222> LOCATION: (31)..(34)
<223> OTHER INFORMATION: Xaa can be any naturally occurring amino acid
<220> FEATURE:
<221> NAME/KEY: misc_feature
<222> LOCATION: (48)..(79)
<223> OTHER INFORMATION: Xaa can be any naturally occurring amino acid
<220> FEATURE:
<221> NAME/KEY: misc_feature
<222> LOCATION: (108)..(164)
<223> OTHER INFORMATION: Xaa can be any naturally occurring amino acid
<220> FEATURE:
<221> NAME/KEY: misc_feature
<222> LOCATION: (174)..(174)
<223> OTHER INFORMATION: Xaa can be any naturally occurring amino acid
<220> FEATURE:
<221> NAME/KEY: misc_feature
<222> LOCATION: (188)..(205)
<223> OTHER INFORMATION: Xaa can be any naturally occurring amino acid -continued
<220> FEATURE:
<221> NAME/KEY: misc_feature
<222> LOCATION: (252)..(256)
<223> OTHER INFORMATION: Xaa can be any naturally occurring amino acid
<220> FEATURE:
<221> NAME/KEY: misc_feature
<222> LOCATION: (269)..(298)
<223> OTHER INFORMATION: Xaa can be any naturally occurring amino acid
<220> FEATURE:
<221> NAME/KEY: misc_feature
<222> LOCATION: (322)..(331)
<223> OTHER INFORMATION: Xaa can be any naturally occurring amino acid
<220> FEATURE:
<221> NAME/KEY: misc_feature
<222> LOCATION: (352)..(353)
<223> OTHER INFORMATION: Xaa can be any naturally occurring amino acid
<220> FEATURE:
<221> NAME/KEY: misc_feature
<222> LOCATION: (378)..(388)
<223> OTHER INFORMATION: Xaa can be any naturally occurring amino acid

<400> SEQUENCE: 19

Arg Tyr Tyr Arg Asp Phe Ser Glu Glu Ser Val Leu Gly Cys Gly Gly
1 5 10 15

Phe Gly Tyr Val Met Lys Val Lys Asn Lys Lys Phe Asn Ile Xaa Xaa
20 25 30

Xaa Xaa Ala Tyr Ala Val Lys Lys Ile Thr Leu Ser Ile Asn Lys Xaa
35 40 45

Xaa Xaa Xaa Xaa Xaa Xaa Xaa Xaa Xaa Xaa Xaa Xaa Xaa Xaa Xaa Xaa
50 55 60

Xaa Xaa Xaa Xaa Xaa Xaa Xaa Xaa Xaa Xaa Xaa Xaa Xaa Xaa Xaa Asn
65 70 75 80

Ser Leu Ile Met Glu Glu Val Ile Met Ile Ala Lys Leu Gln His Glu
85 90 95

Asn Ile Val Arg Tyr Tyr Asp Ala Trp Val Glu Xaa Xaa Xaa Xaa Xaa
100 105 110

Xaa Xaa Xaa Xaa Xaa Xaa Xaa Xaa Xaa Xaa Xaa Xaa Xaa Xaa Xaa Xaa
115 120 125

Xaa Xaa Xaa Xaa Xaa Xaa Xaa Xaa Xaa Xaa Xaa Xaa Xaa Xaa Xaa Xaa
130 135 140

Xaa Xaa Xaa Xaa Xaa Xaa Xaa Xaa Xaa Xaa Xaa Xaa Xaa Xaa Xaa Xaa
145 150 155 160

Xaa Xaa Xaa Xaa Leu Tyr Ile Leu Met Glu Tyr Cys Pro Xaa Gly Lys
165 170 175

Thr Leu Arg Glu Ala Ile Asp Cys Gly Phe Ile Xaa Xaa Xaa Xaa Xaa
180 185 190

Xaa Xaa Xaa Xaa Xaa Xaa Xaa Xaa Xaa Xaa Xaa Xaa Xaa Tyr Lys Asn
195 200 205

Glu Lys Leu Ile Trp Glu Leu Ile Lys Gln Ile Leu Lys Gly Ile Tyr
210 215 220

Tyr Ile His Asp Met Lys Met Met His Arg Asp Ile Lys Pro Ser Asn
225 230 235 240

Ile Phe Leu Gln Ile Asn Asp Asp Ile Leu Ser Xaa Xaa Xaa Xaa Xaa
245 250 255

Ala Lys Ile Gly Asp Phe Gly Leu Thr Thr Lys Ile Xaa Xaa Xaa Xaa
260 265 270

Xaa Xaa Xaa Xaa Xaa Xaa Xaa Xaa Xaa Xaa Xaa Xaa Xaa Xaa Xaa Xaa
275 280 285

Xaa Xaa Xaa Xaa Xaa Xaa Xaa Xaa Xaa Xaa Asn Thr Gln Ile Asn Pro
290 295 300

```
Ser Ala Gly Thr Val Asn Tyr Met Ser Pro Glu Gln Leu Asn Gly Glu
305                 310                 315                 320

His Xaa Xaa Xaa Xaa Xaa Xaa Xaa Xaa Xaa Xaa Phe Asp Gln Lys Ala
                325                 330                 335

Asp Ile Phe Ser Leu Gly Val Val Phe Phe Glu Met Phe His Glu Xaa
            340                 345                 350

Xaa Pro Phe Ser Thr Ser Met Glu Arg Ser Ile Val Leu Ser Asn Leu
        355                 360                 365

Leu Lys Cys Ile Tyr Pro Glu Ser Ile Xaa Xaa Xaa Xaa Xaa Xaa Xaa
    370                 375                 380

Xaa Xaa Xaa Xaa Arg Ser Asp Asn Lys Ile Phe Gln Phe Leu Leu Ser
385                 390                 395                 400

Leu Leu Glu Ile Asp Pro Gln Asn Arg Leu Ser Ala Tyr Ser Leu Leu
                405                 410                 415

His Glu Asn Phe Phe Phe Ser Tyr Glu Lys Asn Phe
            420                 425


<210> SEQ ID NO 20
<211> LENGTH: 445
<212> TYPE: PRT
<213> ORGANISM: Toxoplasma gondii
<220> FEATURE:
<221> NAME/KEY: MISC_FEATURE
<223> OTHER INFORMATION: X represents amino acid locations having low or
      no homology to other poly peptides listed herein
<220> FEATURE:
<221> NAME/KEY: misc_feature
<222> LOCATION: (31)..(34)
<223> OTHER INFORMATION: Xaa can be any naturally occurring amino acid
<220> FEATURE:
<221> NAME/KEY: misc_feature
<222> LOCATION: (51)..(55)
<223> OTHER INFORMATION: Xaa can be any naturally occurring amino acid
<220> FEATURE:
<221> NAME/KEY: misc_feature
<222> LOCATION: (81)..(180)
<223> OTHER INFORMATION: Xaa can be any naturally occurring amino acid
<220> FEATURE:
<221> NAME/KEY: misc_feature
<222> LOCATION: (191)..(191)
<223> OTHER INFORMATION: Xaa can be any naturally occurring amino acid
<220> FEATURE:
<221> NAME/KEY: misc_feature
<222> LOCATION: (212)..(221)
<223> OTHER INFORMATION: Xaa can be any naturally occurring amino acid
<220> FEATURE:
<221> NAME/KEY: misc_feature
<222> LOCATION: (299)..(305)
<223> OTHER INFORMATION: Xaa can be any naturally occurring amino acid
<220> FEATURE:
<221> NAME/KEY: misc_feature
<222> LOCATION: (339)..(348)
<223> OTHER INFORMATION: Xaa can be any naturally occurring amino acid
<220> FEATURE:
<221> NAME/KEY: misc_feature
<222> LOCATION: (370)..(370)
<223> OTHER INFORMATION: Xaa can be any naturally occurring amino acid
<220> FEATURE:
<221> NAME/KEY: misc_feature
<222> LOCATION: (396)..(404)
<223> OTHER INFORMATION: Xaa can be any naturally occurring amino acid

<400> SEQUENCE: 20

Arg Tyr Arg Ser Glu Phe Ile Glu Gln Cys Leu Leu Gly Ser Gly Gly
1               5                   10                  15

Phe Ala Pro Val Tyr Val Cys Arg Lys Lys Val Asp Gly Arg Xaa Xaa
            20                  25                  30
```

```
Xaa Xaa Leu Tyr Ala Val Lys Lys Ile Ala Ile Arg Lys Asn Glu Ala
        35                  40                  45

Glu Lys Xaa Xaa Xaa Xaa Xaa Ala Leu Arg Glu Val Gln Ser Leu Ala
    50                  55                  60

Ala Leu Ser His Lys His Ile Val Arg Tyr Tyr Asp Ala Trp Ile Glu
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa Xaa
                165                 170                 175

Xaa Xaa Xaa Xaa Leu Tyr Ile Gln Met Glu Leu Cys Ser Lys Xaa His
            180                 185                 190

Ser Leu Arg His Leu Ile Asp Gln Cys Asp Lys Glu Glu Gly Ser Leu
        195                 200                 205

Leu Thr Ala Xaa Xaa Xaa Xaa Xaa Xaa Xaa Xaa Xaa Xaa Gly Asn Gly
    210                 215                 220

Asp Lys Val Ala Thr Lys Ile Phe Arg Gln Leu Leu Thr Val Val Ser
225                 230                 235                 240

His Phe His Arg Gln Gly Ile Val His Arg Asp Leu Lys Pro Asp Asn
                245                 250                 255

Ile Leu Phe Glu Met Gln Ser Ser Val Ser Ser Asp Asp Val Gly Thr
            260                 265                 270

Ile Arg Val Ala Asp Phe Gly Leu Ala Arg Thr Leu His Arg Ser Met
        275                 280                 285

Lys His Ser Pro Ser Asn Val Glu Leu Asn Xaa Xaa Xaa Xaa Xaa Xaa
    290                 295                 300

Xaa Asp Val Arg Pro Leu Asp Glu Leu Glu Val Gly Pro Ser Pro Thr
305                 310                 315                 320

Gly Asn Leu Gly Ser Val Val Tyr Cys Ala Pro Glu Gln Glu Arg Gly
                325                 330                 335

Glu Ser Xaa Xaa Xaa Xaa Xaa Xaa Xaa Xaa Xaa Xaa Tyr Asp Phe Ser
            340                 345                 350

Val Asp Glu Tyr Ser Leu Gly Met Ile Ala Leu Glu Met Trp Leu Ala
        355                 360                 365

Val Xaa Ala Gly Gln Gly Phe Arg Glu Arg Phe Asn Ile Met Thr Asp
    370                 375                 380

Ile Ser Arg Gly Lys Pro Ile Pro Gln Trp Phe Xaa Xaa Xaa Xaa Xaa
385                 390                 395                 400

Xaa Xaa Xaa Xaa Tyr Ala Trp Asn Pro Arg Met Ala Glu Val Ile Ala
                405                 410                 415

Ser Leu Leu Glu Arg Asp Pro Gly Lys Arg Arg Thr Ser Glu Glu Ile
            420                 425                 430

Leu Asn Lys Ala Asp Leu Pro Gly Asp Pro Ala Asp Val
        435                 440                 445
```

```
<210> SEQ ID NO 21
<211> LENGTH: 388
<212> TYPE: PRT
<213> ORGANISM: Toxoplasma gondii
<220> FEATURE:
<221> NAME/KEY: MISC_FEATURE
<223> OTHER INFORMATION: X represents amino acid locations having low or
      no homology to other poly peptides listed herein
<220> FEATURE:
<221> NAME/KEY: misc_feature
<222> LOCATION: (31)..(34)
<223> OTHER INFORMATION: Xaa can be any naturally occurring amino acid
<220> FEATURE:
<221> NAME/KEY: misc_feature
<222> LOCATION: (51)..(52)
<223> OTHER INFORMATION: Xaa can be any naturally occurring amino acid
<220> FEATURE:
<221> NAME/KEY: misc_feature
<222> LOCATION: (81)..(123)
<223> OTHER INFORMATION: Xaa can be any naturally occurring amino acid
<220> FEATURE:
<221> NAME/KEY: misc_feature
<222> LOCATION: (134)..(135)
<223> OTHER INFORMATION: Xaa can be any naturally occurring amino acid
<220> FEATURE:
<221> NAME/KEY: misc_feature
<222> LOCATION: (145)..(145)
<223> OTHER INFORMATION: Xaa can be any naturally occurring amino acid
<220> FEATURE:
<221> NAME/KEY: misc_feature
<222> LOCATION: (147)..(164)
<223> OTHER INFORMATION: Xaa can be any naturally occurring amino acid
<220> FEATURE:
<221> NAME/KEY: misc_feature
<222> LOCATION: (208)..(215)
<223> OTHER INFORMATION: Xaa can be any naturally occurring amino acid
<220> FEATURE:
<221> NAME/KEY: misc_feature
<222> LOCATION: (229)..(254)
<223> OTHER INFORMATION: Xaa can be any naturally occurring amino acid
<220> FEATURE:
<221> NAME/KEY: misc_feature
<222> LOCATION: (283)..(291)
<223> OTHER INFORMATION: Xaa can be any naturally occurring amino acid
<220> FEATURE:
<221> NAME/KEY: misc_feature
<222> LOCATION: (311)..(313)
<223> OTHER INFORMATION: Xaa can be any naturally occurring amino acid
<220> FEATURE:
<221> NAME/KEY: misc_feature
<222> LOCATION: (338)..(346)
<223> OTHER INFORMATION: Xaa can be any naturally occurring amino acid

<400> SEQUENCE: 21

Arg Tyr Leu Asn Asp Phe Glu Glu Leu Lys Pro Leu Gly Gln Gly Gly
1               5                   10                  15

Phe Gly His Val Val Leu Cys Lys Asn Lys Leu Asp Gly Arg Xaa Xaa
            20                  25                  30

Xaa Xaa Gln Tyr Ala Val Lys Lys Ile Arg Leu Lys Asp Lys Glu Ile
        35                  40                  45

Pro Val Xaa Xaa Asn Ser Arg Ile Val Arg Glu Val Ala Thr Leu Ser
    50                  55                  60

Arg Leu Gln His Gln His Val Val Arg Tyr Tyr Gln Ala Trp Phe Glu
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Leu Tyr Ile Gln Met
        115                 120                 125
```

-continued

```
Glu Tyr Cys Pro Arg Xaa Xaa Thr Leu Arg Gln Val Phe Glu Ser Tyr
    130                 135                 140

Xaa Asn Xaa Xaa Xaa Xaa Xaa Xaa Xaa Xaa Xaa Xaa Xaa Xaa Xaa Xaa
145                 150                 155                 160

Xaa Xaa Xaa Xaa His Phe Asp Lys Asp Phe Ala Trp His Leu Ile Arg
                165                 170                 175

Gln Ile Val Glu Gly Leu Ala His Ile His Gly Gln Gly Ile Ile His
            180                 185                 190

Arg Asp Phe Thr Pro Asn Asn Ile Phe Phe Asp Ala Arg Asn Asp Xaa
        195                 200                 205

Xaa Xaa Xaa Xaa Xaa Xaa Xaa Ile Lys Ile Gly Asp Phe Gly Leu Ala
    210                 215                 220

Lys Phe Leu Lys Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Val Ala
                245                 250                 255

Gly Ser Gly Val Asp Ser Thr Gly Gln Ala Gly Thr Tyr Phe Tyr Thr
            260                 265                 270

Ala Pro Glu Ile Glu Gln Asp Trp Pro Lys Xaa Xaa Xaa Xaa Xaa Xaa
        275                 280                 285

Xaa Xaa Xaa Ile Asp Glu Lys Ala Asp Met Tyr Ser Leu Gly Val Val
    290                 295                 300

Phe Phe Glu Leu Trp His Xaa Xaa Xaa Pro Phe Gly Thr Ala Met Glu
305                 310                 315                 320

Arg His Val Ile Leu Thr Asn Leu Lys Leu Lys Gly Glu Leu Pro Leu
                325                 330                 335

Lys Xaa Xaa Xaa Xaa Xaa Xaa Xaa Xaa Xaa Trp Val Asn Glu Phe Pro
            340                 345                 350

Glu Gln Ala Ser Leu Leu Arg Arg Leu Met Ser Pro Ser Pro Ser Asp
        355                 360                 365

Arg Pro Ser Ala Thr Glu Leu Leu Lys His Ala Phe Pro Pro Arg Met
    370                 375                 380

Glu Ser Glu Leu
385
```

<210> SEQ ID NO 22
<211> LENGTH: 449
<212> TYPE: PRT
<213> ORGANISM: Toxoplasma gondii
<220> FEATURE:
<221> NAME/KEY: MISC_FEATURE
<223> OTHER INFORMATION: X represents amino acid locations having low or
no homology to other poly peptides listed herein
<220> FEATURE:
<221> NAME/KEY: misc_feature
<222> LOCATION: (31)..(34)
<223> OTHER INFORMATION: Xaa can be any naturally occurring amino acid
<220> FEATURE:
<221> NAME/KEY: misc_feature
<222> LOCATION: (51)..(52)
<223> OTHER INFORMATION: Xaa can be any naturally occurring amino acid
<220> FEATURE:
<221> NAME/KEY: misc_feature
<222> LOCATION: (81)..(182)
<223> OTHER INFORMATION: Xaa can be any naturally occurring amino acid
<220> FEATURE:
<221> NAME/KEY: misc_feature
<222> LOCATION: (193)..(193)
<223> OTHER INFORMATION: Xaa can be any naturally occurring amino acid
<220> FEATURE:
<221> NAME/KEY: misc_feature
<222> LOCATION: (204)..(204)

<223> OTHER INFORMATION: Xaa can be any naturally occurring amino acid
<220> FEATURE:
<221> NAME/KEY: misc_feature
<222> LOCATION: (206)..(225)
<223> OTHER INFORMATION: Xaa can be any naturally occurring amino acid
<220> FEATURE:
<221> NAME/KEY: misc_feature
<222> LOCATION: (269)..(276)
<223> OTHER INFORMATION: Xaa can be any naturally occurring amino acid
<220> FEATURE:
<221> NAME/KEY: misc_feature
<222> LOCATION: (292)..(314)
<223> OTHER INFORMATION: Xaa can be any naturally occurring amino acid
<220> FEATURE:
<221> NAME/KEY: misc_feature
<222> LOCATION: (346)..(352)
<223> OTHER INFORMATION: Xaa can be any naturally occurring amino acid
<220> FEATURE:
<221> NAME/KEY: misc_feature
<222> LOCATION: (373)..(374)
<223> OTHER INFORMATION: Xaa can be any naturally occurring amino acid
<220> FEATURE:
<221> NAME/KEY: misc_feature
<222> LOCATION: (399)..(404)
<223> OTHER INFORMATION: Xaa can be any naturally occurring amino acid

<400> SEQUENCE: 22

```
Arg Leu Arg Thr Glu Phe Glu Val Leu Met Tyr Leu Gly Lys Gly Ala
1               5                   10                  15

Phe Gly Asp Val Leu Lys Val Arg Asn Ile Leu Asp Asn Arg Xaa Xaa
            20                  25                  30

Xaa Xaa Glu Tyr Ala Ile Lys Arg Ile Pro Leu Pro Ala Arg Ser Arg
        35                  40                  45

Gln Leu Xaa Xaa Tyr Lys Lys Met Thr Arg Glu Val Glu Leu Leu Ser
    50                  55                  60

Arg Leu Asn His Glu Asn Val Val Arg Tyr Phe Asn Ser Trp Ile Glu
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Met Tyr Ile Gln Met Glu Phe Cys Glu Lys
            180                 185                 190

Xaa Cys Thr Leu Arg Thr Ala Ile Asp Asp Asn Xaa Leu Xaa Xaa Xaa
        195                 200                 205

Xaa Xaa Xaa Xaa Xaa Xaa Xaa Xaa Xaa Xaa Xaa Xaa Xaa Xaa Xaa Xaa
    210                 215                 220

Xaa Phe Asn Asp Thr Asp Arg Leu Trp Arg Leu Phe Arg Glu Ile Ala
225                 230                 235                 240

Glu Gly Leu Ala His Ile His Gln Gln Gly Ile Ile His Arg Asp Leu
                245                 250                 255

Lys Pro Val Asn Ile Phe Leu Asp Ser His Asp Gln Xaa Xaa Xaa Xaa
            260                 265                 270
```

```
Xaa Xaa Xaa Xaa Ile Lys Ile Gly Asp Phe Gly Leu Ala Thr Thr Ser
        275                 280                 285

Phe Leu Ala Xaa Xaa Xaa Xaa Xaa Xaa Xaa Xaa Xaa Xaa Xaa Xaa Xaa
    290                 295                 300

Xaa Xaa Xaa Xaa Xaa Xaa Xaa Xaa Xaa Xaa Ile Thr Ser Ala Glu Asp
305                 310                 315                 320

Gly Thr Gly Thr Gly Lys Val Gly Thr Thr Leu Tyr Val Ala Pro Glu
                325                 330                 335

Leu Thr Gly Asn Ala Ser Lys Ser Val Xaa Xaa Xaa Xaa Xaa Xaa Xaa
            340                 345                 350

Tyr Asn Gln Lys Val Asp Met Tyr Thr Leu Gly Ile Ile Leu Phe Glu
        355                 360                 365

Met Cys Gln Pro Xaa Xaa Pro Phe Asp Thr Ser Met Glu Arg Ala Gln
    370                 375                 380

Thr Ile Met Ala Leu Arg Asn Val Ser Ile Asn Ile Pro Asp Xaa Xaa
385                 390                 395                 400

Xaa Xaa Xaa Xaa Ala Met Leu Lys Asp Pro Lys Tyr Glu Lys Thr Val
                405                 410                 415

Lys Met Leu Gln Trp Leu Leu Asn His Asp Pro Ala Gln Arg Pro Thr
            420                 425                 430

Ala Glu Glu Leu Leu Ile Ser Asp Leu Val Pro Pro Ala Gln Leu Glu
        435                 440                 445

Ala


<210> SEQ ID NO 23
<211> LENGTH: 464
<212> TYPE: PRT
<213> ORGANISM: Toxoplasma gondii
<220> FEATURE:
<221> NAME/KEY: MISC_FEATURE
<223> OTHER INFORMATION: X represents amino acid locations having low or
      no homology to other poly peptides listed herein
<220> FEATURE:
<221> NAME/KEY: misc_feature
<222> LOCATION: (31)..(34)
<223> OTHER INFORMATION: Xaa can be any naturally occurring amino acid
<220> FEATURE:
<221> NAME/KEY: misc_feature
<222> LOCATION: (51)..(55)
<223> OTHER INFORMATION: Xaa can be any naturally occurring amino acid
<220> FEATURE:
<221> NAME/KEY: misc_feature
<222> LOCATION: (81)..(199)
<223> OTHER INFORMATION: Xaa can be any naturally occurring amino acid
<220> FEATURE:
<221> NAME/KEY: misc_feature
<222> LOCATION: (210)..(210)
<223> OTHER INFORMATION: Xaa can be any naturally occurring amino acid
<220> FEATURE:
<221> NAME/KEY: misc_feature
<222> LOCATION: (223)..(240)
<223> OTHER INFORMATION: Xaa can be any naturally occurring amino acid
<220> FEATURE:
<221> NAME/KEY: misc_feature
<222> LOCATION: (284)..(291)
<223> OTHER INFORMATION: Xaa can be any naturally occurring amino acid
<220> FEATURE:
<221> NAME/KEY: misc_feature
<222> LOCATION: (317)..(330)
<223> OTHER INFORMATION: Xaa can be any naturally occurring amino acid
<220> FEATURE:
<221> NAME/KEY: misc_feature
<222> LOCATION: (359)..(367)
<223> OTHER INFORMATION: Xaa can be any naturally occurring amino acid
<220> FEATURE:
<221> NAME/KEY: misc_feature
<222> LOCATION: (387)..(389)
```

-continued

<223> OTHER INFORMATION: Xaa can be any naturally occurring amino acid
<220> FEATURE:
<221> NAME/KEY: misc_feature
<222> LOCATION: (407)..(407)
<223> OTHER INFORMATION: Xaa can be any naturally occurring amino acid
<220> FEATURE:
<221> NAME/KEY: misc_feature
<222> LOCATION: (415)..(420)
<223> OTHER INFORMATION: Xaa can be any naturally occurring amino acid

<400> SEQUENCE: 23

Arg Tyr Ala Ser Asp Phe Glu Glu Ile Ala Val Leu Gly Gln Gly Ala
1 5 10 15

Phe Gly Gln Val Val Lys Ala Arg Asn Ala Leu Asp Ser Arg Xaa Xaa
20 25 30

Xaa Xaa Tyr Tyr Ala Ile Lys Lys Ile Arg His Thr Glu Glu Lys Leu
35 40 45

Ser Thr Xaa Xaa Xaa Xaa Xaa Ile Leu Ser Glu Val Met Leu Leu Ala
50 55 60

Ser Leu Asn His Gln Tyr Val Val Arg Tyr Tyr Ala Ala Trp Leu Glu
65 70 75 80

Xaa Xaa Xaa Xaa Xaa Xaa Xaa Xaa Xaa Xaa Xaa Xaa Xaa Xaa Xaa Xaa
85 90 95

Xaa Xaa Xaa Xaa Xaa Xaa Xaa Xaa Xaa Xaa Xaa Xaa Xaa Xaa Xaa Xaa
100 105 110

Xaa Xaa Xaa Xaa Xaa Xaa Xaa Xaa Xaa Xaa Xaa Xaa Xaa Xaa Xaa Xaa
115 120 125

Xaa Xaa Xaa Xaa Xaa Xaa Xaa Xaa Xaa Xaa Xaa Xaa Xaa Xaa Xaa Xaa
130 135 140

Xaa Xaa Xaa Xaa Xaa Xaa Xaa Xaa Xaa Xaa Xaa Xaa Xaa Xaa Xaa Xaa
145 150 155 160

Xaa Xaa Xaa Xaa Xaa Xaa Xaa Xaa Xaa Xaa Xaa Xaa Xaa Xaa Xaa Xaa
165 170 175

Xaa Xaa Xaa Xaa Xaa Xaa Xaa Xaa Xaa Xaa Xaa Xaa Xaa Xaa Xaa Xaa
180 185 190

Xaa Xaa Xaa Xaa Xaa Xaa Xaa Leu Phe Ile Gln Met Glu Tyr Cys Glu
195 200 205

Asn Xaa Arg Thr Leu Tyr Asp Leu Ile His Ser Glu Asn Leu Xaa Xaa
210 215 220

Xaa Xaa Xaa Xaa Xaa Xaa Xaa Xaa Xaa Xaa Xaa Xaa Xaa Xaa Xaa Xaa
225 230 235 240

Asn Gln Gln Arg Asp Glu Tyr Trp Arg Leu Phe Arg Gln Ile Leu Glu
245 250 255

Ala Leu Ser Tyr Ile His Ser Gln Gly Ile Ile His Arg Asp Leu Lys
260 265 270

Pro Met Asn Ile Phe Ile Asp Glu Ser Arg Asn Xaa Xaa Xaa Xaa Xaa
275 280 285

Xaa Xaa Xaa Val Lys Ile Gly Asp Phe Gly Leu Ala Lys Asn Val His
290 295 300

Arg Ser Leu Asp Ile Leu Lys Leu Asp Ser Gln Asn Xaa Xaa Xaa Xaa
305 310 315 320

Xaa Xaa Xaa Xaa Xaa Xaa Xaa Xaa Xaa Xaa Leu Pro Gly Ser Ser Asp
325 330 335

Asn Leu Thr Ser Ala Ile Gly Thr Ala Met Tyr Val Ala Thr Glu Val
340 345 350

Leu Asp Gly Thr Gly His Xaa Xaa Xaa Xaa Xaa Xaa Xaa Xaa Xaa Tyr

```
        355                 360                 365

Asn Glu Lys Ile Asp Met Tyr Ser Leu Gly Ile Ile Phe Phe Glu Met
    370                 375                 380

Ile Tyr Xaa Xaa Xaa Pro Phe Ser Thr Gly Met Glu Arg Val Asn Ile
385                 390                 395                 400

Leu Lys Lys Leu Arg Ser Xaa Val Ser Ile Glu Phe Pro Pro Xaa Xaa
                405                 410                 415

Xaa Xaa Xaa Xaa Asp Phe Asp Asp Asn Lys Met Lys Val Glu Lys Lys
            420                 425                 430

Ile Ile Arg Leu Leu Ile Asp His Asp Pro Asn Lys Arg Pro Gly Ala
        435                 440                 445

Arg Thr Leu Leu Asn Ser Gly Trp Leu Pro Val Lys His Gln Asp Glu
    450                 455                 460


<210> SEQ ID NO 24
<211> LENGTH: 484
<212> TYPE: PRT
<213> ORGANISM: Toxoplasma gondii
<220> FEATURE:
<221> NAME/KEY: MISC_FEATURE
<223> OTHER INFORMATION: X represents amino acid locations having low or
      no homology to other poly peptides listed herein
<220> FEATURE:
<221> NAME/KEY: misc_feature
<222> LOCATION: (31)..(34)
<223> OTHER INFORMATION: Xaa can be any naturally occurring amino acid
<220> FEATURE:
<221> NAME/KEY: misc_feature
<222> LOCATION: (50)..(52)
<223> OTHER INFORMATION: Xaa can be any naturally occurring amino acid
<220> FEATURE:
<221> NAME/KEY: misc_feature
<222> LOCATION: (81)..(219)
<223> OTHER INFORMATION: Xaa can be any naturally occurring amino acid
<220> FEATURE:
<221> NAME/KEY: misc_feature
<222> LOCATION: (231)..(231)
<223> OTHER INFORMATION: Xaa can be any naturally occurring amino acid
<220> FEATURE:
<221> NAME/KEY: misc_feature
<222> LOCATION: (241)..(241)
<223> OTHER INFORMATION: Xaa can be any naturally occurring amino acid
<220> FEATURE:
<221> NAME/KEY: misc_feature
<222> LOCATION: (243)..(260)
<223> OTHER INFORMATION: Xaa can be any naturally occurring amino acid
<220> FEATURE:
<221> NAME/KEY: misc_feature
<222> LOCATION: (304)..(311)
<223> OTHER INFORMATION: Xaa can be any naturally occurring amino acid
<220> FEATURE:
<221> NAME/KEY: misc_feature
<222> LOCATION: (337)..(345)
<223> OTHER INFORMATION: Xaa can be any naturally occurring amino acid
<220> FEATURE:
<221> NAME/KEY: misc_feature
<222> LOCATION: (373)..(373)
<223> OTHER INFORMATION: Xaa can be any naturally occurring amino acid
<220> FEATURE:
<221> NAME/KEY: misc_feature
<222> LOCATION: (381)..(387)
<223> OTHER INFORMATION: Xaa can be any naturally occurring amino acid
<220> FEATURE:
<221> NAME/KEY: misc_feature
<222> LOCATION: (408)..(409)
<223> OTHER INFORMATION: Xaa can be any naturally occurring amino acid
<220> FEATURE:
<221> NAME/KEY: misc_feature
<222> LOCATION: (434)..(439)
<223> OTHER INFORMATION: Xaa can be any naturally occurring amino acid

<400> SEQUENCE: 24
```

-continued

```
Arg Tyr Phe Ile Glu Phe Glu Glu Leu Gln Leu Leu Gly Lys Gly Ala
1               5                   10                  15

Phe Gly Ala Val Ile Lys Val Gln Asn Lys Leu Asp Gly Cys Xaa Xaa
            20                  25                  30

Xaa Xaa Cys Tyr Ala Val Lys Arg Ile Pro Ile Asn Pro Ala Ser Arg
        35                  40                  45

His Xaa Xaa Xaa Phe Arg Arg Ile Lys Gly Glu Val Thr Leu Leu Ser
    50                  55                  60

Arg Leu His His Glu Asn Ile Val Arg Tyr Tyr Asn Ala Trp Ile Glu
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Leu Tyr Ile Gln Met
    210                 215                 220

Glu Tyr Cys Glu Lys Ser Xaa Thr Leu Arg Asp Thr Ile Asp Gln Gly
225                 230                 235                 240

Xaa Leu Xaa Xaa Xaa Xaa Xaa Xaa Xaa Xaa Xaa Xaa Xaa Xaa Xaa Xaa
                245                 250                 255

Xaa Xaa Xaa Xaa Phe Arg Asp Thr Ser Arg Leu Trp Arg Leu Phe Arg
            260                 265                 270

Glu Ile Leu Asp Gly Leu Ala Tyr Ile His Glu Lys Gly Met Ile His
        275                 280                 285

Arg Asp Leu Lys Pro Val Asn Ile Phe Leu Asp Ser Asp Asp His Xaa
    290                 295                 300

Xaa Xaa Xaa Xaa Xaa Xaa Xaa Val Lys Ile Gly Asp Phe Gly Leu Ala
305                 310                 315                 320

Thr Asp His Leu Ala Phe Thr Ala Glu Gly Lys Gln Asp Asp Gln Ala
                325                 330                 335

Xaa Xaa Xaa Xaa Xaa Xaa Xaa Xaa Xaa Gly Asp Gly Val Ile Lys Ser
            340                 345                 350

Asp Pro Ser Gly His Leu Thr Gly Met Val Gly Thr Ala Leu Tyr Val
        355                 360                 365

Ser Pro Glu Val Xaa Gln Gly Ser Thr Lys Ser Ala Xaa Xaa Xaa Xaa
    370                 375                 380

Xaa Xaa Xaa Tyr Asn Gln Lys Val Asp Leu Phe Ser Leu Gly Ile Ile
385                 390                 395                 400

Phe Phe Glu Met Ser Tyr His Xaa Xaa Pro Met Val Thr Ala Ser Glu
                405                 410                 415
```

```
Arg Ile Phe Val Leu Asn Gln Leu Arg Asp Pro Thr Ser Pro Lys Phe
            420                 425                 430

Pro Xaa Xaa Xaa Xaa Xaa Xaa Asp Asp Phe Asp Asp Gly Glu His Thr
        435                 440                 445

Lys Gln Lys Ser Val Ile Ser Trp Leu Leu Asn His Asp Pro Ala Lys
    450                 455                 460

Arg Pro Thr Ala Met Glu Leu Leu Lys Ser Glu Leu Leu Pro Pro Pro
465                 470                 475                 480

Gln Met Glu Glu


<210> SEQ ID NO 25
<211> LENGTH: 491
<212> TYPE: PRT
<213> ORGANISM: Toxoplasma gondii
<220> FEATURE:
<221> NAME/KEY: MISC_FEATURE
<223> OTHER INFORMATION: X represents amino acid locations having low or
      no homology to other poly peptides listed herein
<220> FEATURE:
<221> NAME/KEY: misc_feature
<222> LOCATION: (31)..(34)
<223> OTHER INFORMATION: Xaa can be any naturally occurring amino acid
<220> FEATURE:
<221> NAME/KEY: misc_feature
<222> LOCATION: (50)..(52)
<223> OTHER INFORMATION: Xaa can be any naturally occurring amino acid
<220> FEATURE:
<221> NAME/KEY: misc_feature
<222> LOCATION: (81)..(226)
<223> OTHER INFORMATION: Xaa can be any naturally occurring amino acid
<220> FEATURE:
<221> NAME/KEY: misc_feature
<222> LOCATION: (238)..(238)
<223> OTHER INFORMATION: Xaa can be any naturally occurring amino acid
<220> FEATURE:
<221> NAME/KEY: misc_feature
<222> LOCATION: (248)..(248)
<223> OTHER INFORMATION: Xaa can be any naturally occurring amino acid
<220> FEATURE:
<221> NAME/KEY: misc_feature
<222> LOCATION: (250)..(267)
<223> OTHER INFORMATION: Xaa can be any naturally occurring amino acid
<220> FEATURE:
<221> NAME/KEY: misc_feature
<222> LOCATION: (311)..(318)
<223> OTHER INFORMATION: Xaa can be any naturally occurring amino acid
<220> FEATURE:
<221> NAME/KEY: misc_feature
<222> LOCATION: (344)..(352)
<223> OTHER INFORMATION: Xaa can be any naturally occurring amino acid
<220> FEATURE:
<221> NAME/KEY: misc_feature
<222> LOCATION: (355)..(355)
<223> OTHER INFORMATION: Xaa can be any naturally occurring amino acid
<220> FEATURE:
<221> NAME/KEY: misc_feature
<222> LOCATION: (380)..(380)
<223> OTHER INFORMATION: Xaa can be any naturally occurring amino acid
<220> FEATURE:
<221> NAME/KEY: misc_feature
<222> LOCATION: (388)..(394)
<223> OTHER INFORMATION: Xaa can be any naturally occurring amino acid
<220> FEATURE:
<221> NAME/KEY: misc_feature
<222> LOCATION: (415)..(416)
<223> OTHER INFORMATION: Xaa can be any naturally occurring amino acid
<220> FEATURE:
<221> NAME/KEY: misc_feature
<222> LOCATION: (442)..(447)
<223> OTHER INFORMATION: Xaa can be any naturally occurring amino acid

<400> SEQUENCE: 25

Arg Tyr Phe Ile Glu Phe Glu Glu Leu Gln Leu Leu Gly Lys Gly Ala
```

-continued

```
1               5                   10                  15

Phe Gly Ala Val Ile Lys Val Gln Asn Lys Leu Asp Gly Cys Xaa Xaa
            20                  25                  30

Xaa Xaa Cys Tyr Ala Val Lys Arg Ile Pro Ile Asn Pro Ala Ser Arg
        35                  40                  45

Gln Xaa Xaa Xaa Phe Arg Arg Ile Lys Gly Glu Val Thr Leu Leu Ser
    50                  55                  60

Arg Leu His His Glu Asn Ile Val Arg Tyr Tyr Asn Ala Trp Ile Glu
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa Xaa
    210                 215                 220

Xaa Xaa Leu Tyr Ile Gln Met Glu Tyr Cys Glu Lys Ser Xaa Thr Leu
225                 230                 235                 240

Arg Asp Thr Ile Asp Gln Gly Xaa Leu Xaa Xaa Xaa Xaa Xaa Xaa Xaa
                245                 250                 255

Xaa Xaa Xaa Xaa Xaa Xaa Xaa Xaa Xaa Xaa Xaa Tyr Arg Asp Thr Val
            260                 265                 270

Arg Leu Trp Arg Leu Phe Arg Glu Ile Leu Asp Gly Leu Ala Tyr Ile
        275                 280                 285

His Glu Lys Gly Met Ile His Arg Asp Leu Lys Pro Val Asn Ile Phe
    290                 295                 300

Leu Asp Ser Asp Asp His Xaa Xaa Xaa Xaa Xaa Xaa Xaa Xaa Val Lys
305                 310                 315                 320

Ile Gly Asp Phe Gly Leu Ala Thr Asp His Leu Ala Phe Ser Ala Asp
                325                 330                 335

Ser Lys Gln Asp Asp Gln Thr Xaa Xaa Xaa Xaa Xaa Xaa Xaa Xaa Xaa
            340                 345                 350

Gly Asp Xaa Leu Ile Lys Ser Asp Pro Ser Gly His Leu Thr Gly Met
        355                 360                 365

Val Gly Thr Ala Leu Tyr Val Ser Pro Glu Val Xaa Gln Gly Ser Thr
    370                 375                 380

Lys Ser Ala Xaa Xaa Xaa Xaa Xaa Xaa Xaa Tyr Asn Gln Lys Val Asp
385                 390                 395                 400

Leu Phe Ser Leu Gly Ile Ile Phe Phe Glu Met Ser Tyr His Xaa Xaa
                405                 410                 415

Pro Met Val Thr Ala Ser Glu Arg Ile Phe Val Leu Asn Gln Leu Arg
            420                 425                 430
```

```
Asp Pro Thr Ser Pro Lys Phe Pro Glu Xaa Xaa Xaa Xaa Xaa Xaa Asp
        435                 440                 445

Phe Asp Asp Gly Glu His Ala Lys Gln Lys Ser Val Ile Ser Trp Leu
    450                 455                 460

Leu Asn His Asp Pro Ala Lys Arg Pro Thr Ala Thr Glu Leu Leu Lys
465                 470                 475                 480

Ser Glu Leu Leu Pro Pro Pro Gln Met Glu Glu
                485                 490


<210> SEQ ID NO 26
<211> LENGTH: 240
<212> TYPE: PRT
<213> ORGANISM: Toxoplasma gondii
<220> FEATURE:
<221> NAME/KEY: MISC_FEATURE
<223> OTHER INFORMATION: X represents amino acid locations having low or
      no homology to other poly peptides listed herein
<220> FEATURE:
<221> NAME/KEY: misc_feature
<222> LOCATION: (1)..(7)
<223> OTHER INFORMATION: Xaa can be any naturally occurring amino acid
<220> FEATURE:
<221> NAME/KEY: misc_feature
<222> LOCATION: (51)..(55)
<223> OTHER INFORMATION: Xaa can be any naturally occurring amino acid
<220> FEATURE:
<221> NAME/KEY: misc_feature
<222> LOCATION: (81)..(92)
<223> OTHER INFORMATION: Xaa can be any naturally occurring amino acid
<220> FEATURE:
<221> NAME/KEY: misc_feature
<222> LOCATION: (101)..(109)
<223> OTHER INFORMATION: Xaa can be any naturally occurring amino acid
<220> FEATURE:
<221> NAME/KEY: misc_feature
<222> LOCATION: (114)..(114)
<223> OTHER INFORMATION: Xaa can be any naturally occurring amino acid
<220> FEATURE:
<221> NAME/KEY: misc_feature
<222> LOCATION: (218)..(220)
<223> OTHER INFORMATION: Xaa can be any naturally occurring amino acid
<220> FEATURE:
<221> NAME/KEY: misc_feature
<222> LOCATION: (239)..(240)
<223> OTHER INFORMATION: Xaa can be any naturally occurring amino acid

<400> SEQUENCE: 26

Xaa Xaa Xaa Xaa Xaa Xaa Xaa Ala Asp Ile Phe Pro Leu Asp Ala Gln
1               5                   10                  15

Gly Ser Ser Gly Arg Leu Ser Pro Ser Ser Thr Leu Thr Pro Ser Gly
            20                  25                  30

Pro Val Ser Ala Pro Ser Arg Ser Pro Val Ser Ser Pro Ser Pro Asp
        35                  40                  45

Gly Thr Xaa Xaa Xaa Xaa Xaa Ala Thr Gln Glu Thr Arg Asp Ala Gly
    50                  55                  60

Ala Thr Ala Glu Ala Ala Leu Ser Gln Arg Cys Gln Leu Cys Ser Gly
65                  70                  75                  80

Xaa Xaa Xaa Xaa Xaa Xaa Xaa Xaa Xaa Xaa Xaa Xaa Glu Cys Asp Val
                85                  90                  95

Glu Cys Val Arg Xaa Xaa Xaa Xaa Xaa Xaa Xaa Xaa Xaa Tyr Leu Phe
            100                 105                 110

Arg Xaa Val Leu Ser Glu Thr Gln Arg Ala Phe Phe Ala Val Val Asp
        115                 120                 125

Val Leu Leu Pro Arg Asn Tyr Pro Ala Gly Pro Pro Tyr Val Ala Val
    130                 135                 140
```

Gly Leu Ser His Ala Val Pro Arg Thr Glu Val Gln Arg Leu Leu Arg
145 150 155 160

Asp Leu Arg Glu Glu Phe Glu Ala Ser Lys Gly Glu Val Val Leu Tyr
165 170 175

Arg Leu Cys Leu Gln Leu Gln Ser Phe Met Ala Glu Leu Ser Ser Thr
180 185 190

Ser Cys Phe Ser Asn Leu Trp Glu Glu Met His Phe Lys Glu Arg Gln
195 200 205

Arg Arg His Leu Leu Leu Arg Glu Gln Xaa Xaa Xaa His Met Ile His
210 215 220

Gln Ser Leu Lys Ala Arg Gln Gly Leu Leu Ser His Pro Phe Xaa Xaa
225 230 235 240

<210> SEQ ID NO 27
<211> LENGTH: 240
<212> TYPE: PRT
<213> ORGANISM: Toxoplasma gondii
<220> FEATURE:
<221> NAME/KEY: MISC_FEATURE
<223> OTHER INFORMATION: X represents amino acid locations having low or no homology to other poly peptides listed herein
<220> FEATURE:
<221> NAME/KEY: misc_feature
<222> LOCATION: (1)..(32)
<223> OTHER INFORMATION: Xaa can be any naturally occurring amino acid
<220> FEATURE:
<221> NAME/KEY: misc_feature
<222> LOCATION: (62)..(63)
<223> OTHER INFORMATION: Xaa can be any naturally occurring amino acid
<220> FEATURE:
<221> NAME/KEY: misc_feature
<222> LOCATION: (81)..(92)
<223> OTHER INFORMATION: Xaa can be any naturally occurring amino acid
<220> FEATURE:
<221> NAME/KEY: misc_feature
<222> LOCATION: (101)..(109)
<223> OTHER INFORMATION: Xaa can be any naturally occurring amino acid
<220> FEATURE:
<221> NAME/KEY: misc_feature
<222> LOCATION: (114)..(114)
<223> OTHER INFORMATION: Xaa can be any naturally occurring amino acid
<220> FEATURE:
<221> NAME/KEY: misc_feature
<222> LOCATION: (218)..(220)
<223> OTHER INFORMATION: Xaa can be any naturally occurring amino acid

<400> SEQUENCE: 27

Xaa Xaa Xaa Xaa Xaa Xaa Xaa Xaa Xaa Xaa Xaa Xaa Xaa Xaa Xaa Xaa
1 5 10 15

Xaa Xaa Xaa Xaa Xaa Xaa Xaa Xaa Xaa Xaa Xaa Xaa Xaa Xaa Xaa Xaa
20 25 30

Ala Ser Ser Ser Ala Ser Arg Ser Pro Val Ser Ser Pro Ala Pro Asp
35 40 45

Gly Pro Pro Ala Ser Cys Leu Ala Ala Gln Glu Thr Arg Xaa Xaa Gly
50 55 60

Pro Arg Asp Pro Glu Ile Pro Arg Pro Arg Cys Gln Leu Cys Leu Gly
65 70 75 80

Xaa Xaa Xaa Xaa Xaa Xaa Xaa Xaa Xaa Xaa Xaa Xaa Asp Cys Asp Val
85 90 95

Glu Cys Val Arg Xaa Xaa Xaa Xaa Xaa Xaa Xaa Xaa Xaa Tyr Leu Phe
100 105 110

Arg Xaa Val Leu Ser Glu Thr Gln Gln Ala Phe Phe Ala Ile Val Asp
115 120 125

```
Val Leu Leu Pro Arg Asn Tyr Pro Ala Ala Pro Pro Tyr Val Ala Val
    130                 135                 140

Gly Leu Ser Ala Ala Val Pro Arg Lys Glu Leu Glu Gln Leu Arg Asn
145                 150                 155                 160

Ser Leu Arg Glu Glu Tyr Glu Ala Ser Arg Gly Glu Val Val Leu Tyr
                165                 170                 175

Arg Leu Cys Leu Gln Leu Gln Ser Phe Met Ala Glu Leu Ser Ser Thr
            180                 185                 190

Leu Cys Phe Ser Asn Leu Trp Glu Glu Met His Phe Lys Glu Arg Gln
        195                 200                 205

Arg Arg His Phe Leu Leu Arg Glu Gln Xaa Xaa Xaa His Met Ile His
    210                 215                 220

Arg Asn Met Lys Ala Arg Gln Gly Leu Leu Ser His Pro Phe Gly Pro
225                 230                 235                 240


<210> SEQ ID NO 28
<211> LENGTH: 239
<212> TYPE: PRT
<213> ORGANISM: Toxoplasma gondii

<400> SEQUENCE: 28

Met Asp Asn Asp Asn Asn Lys Arg Lys Lys Thr Lys Lys Lys Lys Val
1               5                   10                  15

Arg Asn Val Asn Asn Lys Asn Ser Asn Glu Asn Lys Lys Lys Gly Ile
            20                  25                  30

Gln Glu Asn Gln Asp Glu Gln Asn Tyr Thr Glu Gln Tyr Ala Asp Gln
        35                  40                  45

Ile Glu Glu Ile Leu Ala Leu His Asn Ile Phe Phe Pro Met Tyr Val
    50                  55                  60

Asp Asn Pro Gly His Val Lys Lys Ser Asp Leu Pro Lys Asp Leu Met
65                  70                  75                  80

Lys Arg Asn Glu Tyr Ile Lys Asn Ser Lys Asp Leu Ser Glu Asn Ile
                85                  90                  95

Ile Val Asp Ile Asn Asp Glu Ile Asn Lys Asn Thr Cys Leu Thr Phe
            100                 105                 110

Ser Met Phe Leu Asn Ile Asp Asn Ile Met Glu Lys Tyr Lys Val Thr
        115                 120                 125

Phe Met Tyr Glu Lys Ile Tyr Pro Tyr Ser Tyr Pro Asn Val Val Ile
    130                 135                 140

His Met Asn Thr Lys Leu Asn Glu Glu Gln Lys Asn Asp Val Thr Leu
145                 150                 155                 160

Asn Ile Arg Lys Ile Cys Ala Lys Asn Tyr Gly Arg Ile Thr Leu Phe
                165                 170                 175

Glu Ile Cys Leu Phe Ile Asn Glu Tyr Leu Asn Lys Ile Phe Asn Asn
            180                 185                 190

Asp Phe Gln Asn Leu Trp Glu Glu Met Asn Tyr Arg Ile Asp Asp Thr
        195                 200                 205

Ser Phe Lys Lys Asp Arg Asp Asn Glu Ile Tyr Asn Asp Leu His Asn
    210                 215                 220

Glu Ile Glu Asp Gly Arg Lys Leu Asp Asn Tyr Lys Asn Val Gln
225                 230                 235


<210> SEQ ID NO 29
<211> LENGTH: 240
<212> TYPE: PRT
<213> ORGANISM: Toxoplasma gondii
```

<220> FEATURE:
<221> NAME/KEY: MISC_FEATURE
<223> OTHER INFORMATION: X represents amino acid locations having low or no homology to other poly peptides listed herein
<220> FEATURE:
<221> NAME/KEY: misc_feature
<222> LOCATION: (1)..(22)
<223> OTHER INFORMATION: Xaa can be any naturally occurring amino acid
<220> FEATURE:
<221> NAME/KEY: misc_feature
<222> LOCATION: (74)..(92)
<223> OTHER INFORMATION: Xaa can be any naturally occurring amino acid
<220> FEATURE:
<221> NAME/KEY: misc_feature
<222> LOCATION: (101)..(109)
<223> OTHER INFORMATION: Xaa can be any naturally occurring amino acid
<220> FEATURE:
<221> NAME/KEY: misc_feature
<222> LOCATION: (114)..(115)
<223> OTHER INFORMATION: Xaa can be any naturally occurring amino acid
<220> FEATURE:
<221> NAME/KEY: misc_feature
<222> LOCATION: (197)..(197)
<223> OTHER INFORMATION: Xaa can be any naturally occurring amino acid
<220> FEATURE:
<221> NAME/KEY: misc_feature
<222> LOCATION: (218)..(220)
<223> OTHER INFORMATION: Xaa can be any naturally occurring amino acid
<220> FEATURE:
<221> NAME/KEY: misc_feature
<222> LOCATION: (228)..(228)
<223> OTHER INFORMATION: Xaa can be any naturally occurring amino acid
<220> FEATURE:
<221> NAME/KEY: misc_feature
<222> LOCATION: (232)..(232)
<223> OTHER INFORMATION: Xaa can be any naturally occurring amino acid

<400> SEQUENCE: 29

Xaa Xaa Xaa Xaa Xaa Xaa Xaa Xaa Xaa Xaa Xaa Xaa Xaa Xaa Xaa Xaa
1 5 10 15

Xaa Xaa Xaa Xaa Xaa Xaa Met Ala Gly Gly Arg Gly Ala Ser Gly Arg
20 25 30

Gly Arg Ala Glu Pro Gln Glu Ser Tyr Ser Gln Arg Gln Asp His Glu
35 40 45

Leu Gln Ala Leu Glu Ala Ile Tyr Gly Ser Asp Phe Gln Asp Leu Arg
50 55 60

Pro Asp Ala Arg Gly Arg Val Arg Glu Xaa Xaa Xaa Xaa Xaa Xaa Xaa
65 70 75 80

Xaa Xaa Xaa Xaa Xaa Xaa Xaa Xaa Xaa Xaa Xaa Xaa Pro Pro Glu Ile
85 90 95

Asn Leu Val Leu Xaa Xaa Xaa Xaa Xaa Xaa Xaa Xaa Xaa Tyr Pro Gln
100 105 110

Gly Xaa Xaa Leu Ala Gly Glu Glu Val Tyr Val Gln Val Glu Leu Gln
115 120 125

Val Lys Cys Pro Pro Thr Tyr Pro Asp Val Val Pro Glu Ile Glu Leu
130 135 140

Lys Asn Ala Lys Gly Leu Ser Asn Glu Ser Val Asn Leu Leu Lys Ser
145 150 155 160

His Leu Glu Glu Leu Ala Lys Lys Gln Cys Gly Glu Val Met Ile Phe
165 170 175

Glu Leu Ala His His Val Gln Ser Phe Leu Ser Glu His Asn Lys Pro
180 185 190

Pro Pro Lys Ser Xaa Phe His Glu Glu Met Leu Glu Arg Gln Ala Gln
195 200 205

Glu Lys Gln Gln Arg Leu Leu Glu Ala Xaa Xaa Xaa Arg Arg Lys Glu

```
    210                 215                 220

Glu Gln Glu Xaa Gln Arg Glu Xaa Ile Leu His Glu Ile Gln Arg Arg
225                 230                 235                 240
```

<210> SEQ ID NO 30
<211> LENGTH: 240
<212> TYPE: PRT
<213> ORGANISM: Toxoplasma gondii
<220> FEATURE:
<221> NAME/KEY: MISC_FEATURE
<223> OTHER INFORMATION: X represents amino acid locations having low or no homology to other poly peptides listed herein
<220> FEATURE:
<221> NAME/KEY: misc_feature
<222> LOCATION: (1)..(22)
<223> OTHER INFORMATION: Xaa can be any naturally occurring amino acid
<220> FEATURE:
<221> NAME/KEY: misc_feature
<222> LOCATION: (26)..(34)
<223> OTHER INFORMATION: Xaa can be any naturally occurring amino acid
<220> FEATURE:
<221> NAME/KEY: misc_feature
<222> LOCATION: (74)..(92)
<223> OTHER INFORMATION: Xaa can be any naturally occurring amino acid
<220> FEATURE:
<221> NAME/KEY: misc_feature
<222> LOCATION: (101)..(109)
<223> OTHER INFORMATION: Xaa can be any naturally occurring amino acid
<220> FEATURE:
<221> NAME/KEY: misc_feature
<222> LOCATION: (197)..(197)
<223> OTHER INFORMATION: Xaa can be any naturally occurring amino acid
<220> FEATURE:
<221> NAME/KEY: misc_feature
<222> LOCATION: (205)..(205)
<223> OTHER INFORMATION: Xaa can be any naturally occurring amino acid
<220> FEATURE:
<221> NAME/KEY: misc_feature
<222> LOCATION: (218)..(220)
<223> OTHER INFORMATION: Xaa can be any naturally occurring amino acid
<220> FEATURE:
<221> NAME/KEY: misc_feature
<222> LOCATION: (228)..(228)
<223> OTHER INFORMATION: Xaa can be any naturally occurring amino acid

<400> SEQUENCE: 30

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Met Ala Asp Xaa Xaa Xaa Xaa Xaa Xaa Xaa
            20                  25                  30

Xaa Xaa Glu Lys Ala Lys Glu Ser Phe Arg Glu Arg Gln Ala Gln Glu
        35                  40                  45

Leu Glu Val Ile Lys Ser Ile Phe Gly Cys Asp Val Glu Asp Leu Arg
    50                  55                  60

Pro Gln Ala Asn Pro Ser Leu Trp Lys Xaa Xaa Xaa Xaa Xaa Xaa Xaa
65                  70                  75                  80

Xaa Xaa Xaa Xaa Xaa Xaa Xaa Xaa Xaa Xaa Xaa Xaa Pro Thr Asp Ile
                85                  90                  95

Arg Ile Gln Leu Xaa Xaa Xaa Xaa Xaa Xaa Xaa Xaa Xaa Thr Pro Leu
            100                 105                 110

Arg Asp Ser Ser Asn Gly Leu Glu Thr Tyr Val Cys Thr Lys Leu His
        115                 120                 125

Val Thr Cys Pro Ser Lys Tyr Pro Lys Leu Pro Pro Lys Ile Ser Leu
    130                 135                 140

Glu Glu Ser Lys Gly Met Ser Asp Gln Leu Leu Glu Ala Leu Arg Asn
145                 150                 155                 160
```

```
Gln Leu Gln Ala Gln Ser Gln Glu Leu Arg Gly Glu Val Met Ile Tyr
                165                 170                 175

Glu Leu Ala Gln Thr Val Gln Ala Phe Leu Leu Glu His Asn Lys Pro
            180                 185                 190

Pro Lys Gly Ser Xaa Phe Tyr Asp Gln Met Leu Gln Xaa Asp Lys Gln
        195                 200                 205

Lys Arg Asp Gln Glu Leu Gln Asp Ile Xaa Xaa Xaa Gln Arg Gln Arg
    210                 215                 220

Glu Ser Leu Xaa Gln Arg Gln Thr Leu Ile Asp Glu Val Glu Arg Arg
225                 230                 235                 240


<210> SEQ ID NO 31
<211> LENGTH: 240
<212> TYPE: PRT
<213> ORGANISM: Toxoplasma gondii
<220> FEATURE:
<221> NAME/KEY: MISC_FEATURE
<223> OTHER INFORMATION: X represents amino acid locations having low or
      no homology to other poly peptides listed herein
<220> FEATURE:
<221> NAME/KEY: misc_feature
<222> LOCATION: (1)..(30)
<223> OTHER INFORMATION: Xaa can be any naturally occurring amino acid
<220> FEATURE:
<221> NAME/KEY: misc_feature
<222> LOCATION: (74)..(93)
<223> OTHER INFORMATION: Xaa can be any naturally occurring amino acid
<220> FEATURE:
<221> NAME/KEY: misc_feature
<222> LOCATION: (101)..(109)
<223> OTHER INFORMATION: Xaa can be any naturally occurring amino acid
<220> FEATURE:
<221> NAME/KEY: misc_feature
<222> LOCATION: (114)..(115)
<223> OTHER INFORMATION: Xaa can be any naturally occurring amino acid
<220> FEATURE:
<221> NAME/KEY: misc_feature
<222> LOCATION: (218)..(220)
<223> OTHER INFORMATION: Xaa can be any naturally occurring amino acid
<220> FEATURE:
<221> NAME/KEY: misc_feature
<222> LOCATION: (232)..(234)
<223> OTHER INFORMATION: Xaa can be any naturally occurring amino acid

<400> SEQUENCE: 31

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Met Ser
            20                  25                  30

Leu Ser His Leu Thr Leu Asp Gln Tyr Tyr Glu Ile Gln Cys Asn Glu
        35                  40                  45

Leu Glu Ala Ile Arg Ser Ile Tyr Met Asp Asp Phe Thr Asp Leu Thr
    50                  55                  60

Lys Arg Lys Ser Ser Trp Asp Lys Gln Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Pro Gln Ile
                85                  90                  95

Ile Phe Glu Ile Xaa Xaa Xaa Xaa Xaa Xaa Xaa Xaa Xaa Thr Leu Arg
            100                 105                 110

Ser Xaa Xaa Val Asp Lys Glu Pro Val Glu Ser Ser Ile Thr Leu His
        115                 120                 125

Phe Ala Met Thr Pro Met Tyr Pro Tyr Thr Ala Pro Glu Ile Glu Phe
    130                 135                 140

Lys Asn Val Gln Asn Val Met Asp Ser Gln Leu Gln Met Leu Lys Ser
```

```
145                 150                 155                 160

Glu Phe Lys Lys Ile His Asn Thr Ser Arg Gly Gln Glu Ile Ile Phe
                165                 170                 175

Glu Ile Thr Ser Phe Thr Gln Glu Lys Leu Asp Glu Phe Gln Asn Val
            180                 185                 190

Val Asn Thr Gln Ser Leu Glu Asp Asp Arg Leu Gln Arg Ile Lys Glu
        195                 200                 205

Thr Lys Glu Gln Leu Glu Lys Glu Glu Xaa Xaa Xaa Arg Glu Lys Gln
    210                 215                 220

Gln Glu Thr Ile Lys Lys Arg Xaa Xaa Xaa Ser Asp Glu Gln Arg Arg
225                 230                 235                 240


<210> SEQ ID NO 32
<211> LENGTH: 83
<212> TYPE: PRT
<213> ORGANISM: Toxoplasma gondii
<220> FEATURE:
<221> NAME/KEY: MISC_FEATURE
<223> OTHER INFORMATION: X represents amino acid locations having low or
      no homology to other poly peptides listed herein
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (57)..(58)
<223> OTHER INFORMATION: Xaa can be any naturally occurring amino acid
<220> FEATURE:
<221> NAME/KEY: misc_feature
<222> LOCATION: (83)..(83)
<223> OTHER INFORMATION: Xaa can be any naturally occurring amino acid

<400> SEQUENCE: 32

Xaa Xaa Leu Asp Tyr Ser Leu Pro Gln Val Val Val Thr Ala Gln Ser
1               5                   10                  15

Ala Lys Gln Leu Pro Leu Gly Phe Ser Leu Val Cys Arg Leu Leu Arg
            20                  25                  30

Arg Gly Ile Arg Ala Glu Leu Arg Val Thr Pro Val Val Glu Thr Ser
        35                  40                  45

Tyr Phe Gln Arg Leu Leu Arg Arg Xaa Xaa Ser Arg Arg Ile Leu Tyr
    50                  55                  60

His Val Gln Ile Gln His His Arg Ala Ser Val Ala Ala His Ala Thr
65                  70                  75                  80

Leu Thr Xaa


<210> SEQ ID NO 33
<211> LENGTH: 83
<212> TYPE: PRT
<213> ORGANISM: Toxoplasma gondii
<220> FEATURE:
<221> NAME/KEY: MISC_FEATURE
<223> OTHER INFORMATION: X represents amino acid locations having low or
      no homology to other poly peptides listed herein
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (57)..(58)
<223> OTHER INFORMATION: Xaa can be any naturally occurring amino acid
<220> FEATURE:
<221> NAME/KEY: misc_feature
<222> LOCATION: (82)..(83)
<223> OTHER INFORMATION: Xaa can be any naturally occurring amino acid
```

<400> SEQUENCE: 33

```
Xaa Xaa Asp Glu Ala Ala Leu Pro Gln Val Val Val Thr Ala Gln Ser
1               5                   10                  15

Ala Lys His Leu Pro Leu Gly Phe Ser Leu Val Cys Lys Leu Leu Arg
            20                  25                  30

Arg Gly Val Arg Ala Glu Leu Arg Val Ser Pro Val Val Glu Thr Ser
        35                  40                  45

Tyr Phe Gln Arg Leu Leu Arg Arg Xaa Xaa Ser Arg Arg Ile Leu Tyr
    50                  55                  60

His Val Gln Ile Gln His His Arg Ala Ser Val Ser Ser His Ala Ala
65                  70                  75                  80

Ile Xaa Xaa
```

<210> SEQ ID NO 34
<211> LENGTH: 83
<212> TYPE: PRT
<213> ORGANISM: Toxoplasma gondii
<220> FEATURE:
<221> NAME/KEY: MISC_FEATURE
<223> OTHER INFORMATION: X represents amino acid locations having low or no homology to other poly peptides listed herein
<220> FEATURE:
<221> NAME/KEY: misc_feature
<222> LOCATION: (1)..(2)
<223> OTHER INFORMATION: Xaa can be any naturally occurring amino acid

<400> SEQUENCE: 34

```
Xaa Xaa Leu Gln Ser Cys Tyr Pro Lys Val Val Val Val Thr Gln Lys
1               5                   10                  15

Asn Lys Leu Gln Leu Leu Val Leu Ser Leu Ala Arg Gln Leu Trp Leu
            20                  25                  30

Asn Gly Ile Arg Cys Glu Tyr Arg Leu Ala Pro Val Gln Tyr Leu Ser
        35                  40                  45

Ile Phe Val Asp Lys Leu Lys Lys Gly Thr Leu Val Glu Leu Leu Val
    50                  55                  60

Val Val Met Lys Thr Asn Lys Pro Thr Thr Asn Ser Leu Tyr Asn Ala
65                  70                  75                  80

Ser Asn Ile
```

<210> SEQ ID NO 35
<211> LENGTH: 83
<212> TYPE: PRT
<213> ORGANISM: Toxoplasma gondii
<220> FEATURE:
<221> NAME/KEY: MISC_FEATURE
<223> OTHER INFORMATION: X represents amino acid locations having low or no homology to other poly peptides listed herein
<220> FEATURE:
<221> NAME/KEY: misc_feature
<222> LOCATION: (57)..(58)
<223> OTHER INFORMATION: Xaa can be any naturally occurring amino acid

<400> SEQUENCE: 35

```
Leu Leu Ile Asp Phe His Ser Pro Ser Val Val Ile Thr Ala Lys Ala
1               5                   10                  15

Tyr Lys Leu Leu Met Tyr Ala Phe Ser Leu Tyr Asn Ser Leu Ile Gln
            20                  25                  30

Asn Gly Ile Lys Cys Glu Cys Arg Ile Thr Pro Leu Met Glu Thr Ser
        35                  40                  45

Lys Phe Glu Lys Ser Leu Leu Lys Xaa Xaa Tyr Lys Asn Ile Asn Ile
```

```
    50                  55                  60

His Val Gln Ile Asn Gln Lys Ile Ser Ser Ser Thr Ser Ile Asn Ile
65                  70                  75                  80

Glu Asp Tyr


<210> SEQ ID NO 36
<211> LENGTH: 83
<212> TYPE: PRT
<213> ORGANISM: Toxoplasma gondii
<220> FEATURE:
<221> NAME/KEY: MISC_FEATURE
<223> OTHER INFORMATION: X represents amino acid locations having low or
      no homology to other poly peptides listed herein
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (57)..(58)
<223> OTHER INFORMATION: Xaa can be any naturally occurring amino acid
<220> FEATURE:
<221> NAME/KEY: misc_feature
<222> LOCATION: (79)..(79)
<223> OTHER INFORMATION: Xaa can be any naturally occurring amino acid

<400> SEQUENCE: 36

Xaa Phe Ile Asp Phe His Ser Pro Ser Val Val Ile Thr Thr Lys Ala
1               5                   10                  15

Tyr Lys Leu Leu Val Tyr Ala Phe Ser Leu Tyr Asn Ser Leu Ile Gln
            20                  25                  30

Asn Asn Ile Lys Cys Glu Cys Lys Ile Ser Pro Ile Ile Glu Thr Leu
        35                  40                  45

Lys Phe Glu Gln Asn Leu Leu Lys Xaa Xaa Tyr Asn His Ile Asn Met
    50                  55                  60

His Val Gln Ile Asn His Lys Val Asn Ser Asn Pro Thr Val Xaa Cys
65                  70                  75                  80

Ser Asp Tyr


<210> SEQ ID NO 37
<211> LENGTH: 83
<212> TYPE: PRT
<213> ORGANISM: Toxoplasma gondii
<220> FEATURE:
<221> NAME/KEY: MISC_FEATURE
<223> OTHER INFORMATION: X represents amino acid locations having low or
      no homology to other poly peptides listed herein
<220> FEATURE:
<221> NAME/KEY: misc_feature
<222> LOCATION: (57)..(58)
<223> OTHER INFORMATION: Xaa can be any naturally occurring amino acid

<400> SEQUENCE: 37

Met His Ile Asp Phe His Ser Pro Ser Val Val Ile Thr Thr Lys Ala
1               5                   10                  15

Tyr Lys Leu Leu Val Tyr Ala Phe Ser Leu Tyr Asn Asn Leu Ile Gln
            20                  25                  30

Asn Gly Ile Lys Cys Glu Cys Lys Ile Ser Pro Leu Val Glu Thr Ser
        35                  40                  45

Lys Phe Glu Gln Gly Leu Leu Lys Xaa Xaa Tyr Ser Asp Ile Asn Ile
    50                  55                  60

His Val Gln Ile Ile Gln Lys Val Asn Ser Asn Thr Phe Leu Asn Ile
65                  70                  75                  80
```

Glu Asp Tyr

<210> SEQ ID NO 38
<211> LENGTH: 83
<212> TYPE: PRT
<213> ORGANISM: Toxoplasma gondii
<220> FEATURE:
<221> NAME/KEY: MISC_FEATURE
<223> OTHER INFORMATION: X represents amino acid locations having low or no homology to other poly peptides listed herein
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (57)..(58)
<223> OTHER INFORMATION: Xaa can be any naturally occurring amino acid

<400> SEQUENCE: 38

```
Xaa Xaa Ile Asp Phe His Ser Pro Ser Val Val Ile Thr Thr Lys Ala
1               5                   10                  15

Tyr Lys Leu Leu Val Tyr Ala Phe Ser Leu Tyr Asn Ser Leu Ile Gln
            20                  25                  30

Asn Gly Ile Lys Cys Glu Cys Lys Ile Ser Pro Leu Val Glu Thr Ser
        35                  40                  45

Lys Phe Glu Gln Gly Leu Leu Lys Xaa Xaa Tyr Gly Asp Ile Asn Ile
    50                  55                  60

His Val Gln Ile Thr Gln Lys Val Asn Ser Asn Thr Ser Leu Asn Ile
65                  70                  75                  80

Glu Asp Tyr
```

<210> SEQ ID NO 39
<211> LENGTH: 36
<212> TYPE: DNA
<213> ORGANISM: Artificial Sequence
<220> FEATURE:
<223> OTHER INFORMATION: Primer

<400> SEQUENCE: 39
gaaatagcgg ccgcgtcact gaccaatgag ctttgg 36

<210> SEQ ID NO 40
<211> LENGTH: 34
<212> TYPE: DNA
<213> ORGANISM: Artificial Sequence
<220> FEATURE:
<223> OTHER INFORMATION: Primer

<400> SEQUENCE: 40
gaacaaacta gtagaacgaa gggaggagag ttcg 34

<210> SEQ ID NO 41
<211> LENGTH: 34
<212> TYPE: DNA
<213> ORGANISM: Artificial Sequence
<220> FEATURE:
<223> OTHER INFORMATION: Primer

<400> SEQUENCE: 41
gttcaaaagc tttggaagag accgacgctg aacg 34

<210> SEQ ID NO 42
<211> LENGTH: 35
<212> TYPE: DNA

<213> ORGANISM: Artificial Sequence
<220> FEATURE:
<223> OTHER INFORMATION: Primer

<400> SEQUENCE: 42
gtagttgggc ccgcttcgtt gagtgatgtg agacg 35

<210> SEQ ID NO 43
<211> LENGTH: 26
<212> TYPE: DNA
<213> ORGANISM: Artificial Sequence
<220> FEATURE:
<223> OTHER INFORMATION: Primer

<400> SEQUENCE: 43
cttcagcaat ttgtgggagg aaatgc 26

<210> SEQ ID NO 44
<211> LENGTH: 26
<212> TYPE: DNA
<213> ORGANISM: Artificial Sequence
<220> FEATURE:
<223> OTHER INFORMATION: Primer

<400> SEQUENCE: 44
gagcggctcg tcgctcgtcg ttgagg 26

<210> SEQ ID NO 45
<211> LENGTH: 48
<212> TYPE: DNA
<213> ORGANISM: Artificial Sequence
<220> FEATURE:
<223> OTHER INFORMATION: Primer

<400> SEQUENCE: 45
tcctccactt ccaattttag cgcgtcggtc tcttccacct ctgcctgg 48

<210> SEQ ID NO 46
<211> LENGTH: 50
<212> TYPE: DNA
<213> ORGANISM: Artificial Sequence
<220> FEATURE:
<223> OTHER INFORMATION: Primer

<400> SEQUENCE: 46
tacttccaat ccaatttaat gcatgttccg taggcggtga tccctcgtgg 50

<210> SEQ ID NO 47
<211> LENGTH: 23
<212> TYPE: DNA
<213> ORGANISM: Artificial Sequence
<220> FEATURE:
<223> OTHER INFORMATION: Primer

<400> SEQUENCE: 47
ccacagtttc gttgctctct tgg 23

<210> SEQ ID NO 48
<211> LENGTH: 22
<212> TYPE: DNA
<213> ORGANISM: Artificial Sequence
<220> FEATURE:
<223> OTHER INFORMATION: Primer

<400> SEQUENCE: 48
ctgtatgccg ctagagtgct gg 22

-continued

<210> SEQ ID NO 49
<211> LENGTH: 41
<212> TYPE: DNA
<213> ORGANISM: Artificial Sequence
<220> FEATURE:
<223> OTHER INFORMATION: Primer

<400> SEQUENCE: 49
gaaacgggat ccgcgaagaa acagagcgac agcggtgctg g 41

<210> SEQ ID NO 50
<211> LENGTH: 45
<212> TYPE: DNA
<213> ORGANISM: Artificial Sequence
<220> FEATURE:
<223> OTHER INFORMATION: Primer

<400> SEQUENCE: 50
gcagagtcta gatcacgcgg gagagtcaga agtacatttc tgtgg 45

<210> SEQ ID NO 51
<211> LENGTH: 20
<212> TYPE: DNA
<213> ORGANISM: Artificial Sequence
<220> FEATURE:
<223> OTHER INFORMATION: Primer

<400> SEQUENCE: 51
acgtatgatg cgcgagaaaa 20

<210> SEQ ID NO 52
<211> LENGTH: 19
<212> TYPE: DNA
<213> ORGANISM: Artificial Sequence
<220> FEATURE:
<223> OTHER INFORMATION: Primer

<400> SEQUENCE: 52
gggcgtttca tgacctaaa 19

<210> SEQ ID NO 53
<211> LENGTH: 20
<212> TYPE: DNA
<213> ORGANISM: Artificial Sequence
<220> FEATURE:
<223> OTHER INFORMATION: Primer

<400> SEQUENCE: 53
gcttaacggg tacggcgttt 20

<210> SEQ ID NO 54
<211> LENGTH: 20
<212> TYPE: DNA
<213> ORGANISM: Artificial Sequence
<220> FEATURE:
<223> OTHER INFORMATION: Primer

<400> SEQUENCE: 54
gcggttaatc cagcgtatgc 20

<210> SEQ ID NO 55
<211> LENGTH: 19
<212> TYPE: DNA
<213> ORGANISM: Artificial Sequence
<220> FEATURE:

-continued

<223> OTHER INFORMATION: Primer

<400> SEQUENCE: 55
cagggccgta cgagaacgt 19

<210> SEQ ID NO 56
<211> LENGTH: 20
<212> TYPE: DNA
<213> ORGANISM: Artificial Sequence
<220> FEATURE:
<223> OTHER INFORMATION: Primer

<400> SEQUENCE: 56
gcccacgaca gcagacaact 20

<210> SEQ ID NO 57
<211> LENGTH: 21
<212> TYPE: DNA
<213> ORGANISM: Artificial Sequence
<220> FEATURE:
<223> OTHER INFORMATION: Primer

<400> SEQUENCE: 57
cactcggttc gtgtgctttc t 21

<210> SEQ ID NO 58
<211> LENGTH: 20
<212> TYPE: DNA
<213> ORGANISM: Artificial Sequence
<220> FEATURE:
<223> OTHER INFORMATION: Primer

<400> SEQUENCE: 58
ccgtcacgcc actacaacag 20

<210> SEQ ID NO 59
<211> LENGTH: 23
<212> TYPE: DNA
<213> ORGANISM: Artificial Sequence
<220> FEATURE:
<223> OTHER INFORMATION: Primer

<400> SEQUENCE: 59
ctctgcatgc agctggtcgt tgg 23

<210> SEQ ID NO 60
<211> LENGTH: 25
<212> TYPE: DNA
<213> ORGANISM: Artificial Sequence
<220> FEATURE:
<223> OTHER INFORMATION: Primer

<400> SEQUENCE: 60
gcagccgatt gatttcatcg gatgg 25

<210> SEQ ID NO 61
<211> LENGTH: 23
<212> TYPE: DNA
<213> ORGANISM: Artificial Sequence
<220> FEATURE:
<223> OTHER INFORMATION: Primer

<400> SEQUENCE: 61
caccgtgtca gctgcctcca agg 23

-continued

<210> SEQ ID NO 62
<211> LENGTH: 25
<212> TYPE: DNA
<213> ORGANISM: Artificial Sequence
<220> FEATURE:
<223> OTHER INFORMATION: Primer

<400> SEQUENCE: 62
ctttctgtct gtcctcgctg actgg 25

<210> SEQ ID NO 63
<211> LENGTH: 23
<212> TYPE: DNA
<213> ORGANISM: Artificial Sequence
<220> FEATURE:
<223> OTHER INFORMATION: Primer

<400> SEQUENCE: 63
ccaccagtgt ccaagatcca tcg 23

<210> SEQ ID NO 64
<211> LENGTH: 24
<212> TYPE: DNA
<213> ORGANISM: Artificial Sequence
<220> FEATURE:
<223> OTHER INFORMATION: Primer

<400> SEQUENCE: 64
gatccatcgt ctccgtcctc ttcg 24

<210> SEQ ID NO 65
<211> LENGTH: 21
<212> TYPE: DNA
<213> ORGANISM: Artificial Sequence
<220> FEATURE:
<223> OTHER INFORMATION: Primer

<400> SEQUENCE: 65
cactcggttc gtgtgctttc t 21

<210> SEQ ID NO 66
<211> LENGTH: 20
<212> TYPE: DNA
<213> ORGANISM: Artificial Sequence
<220> FEATURE:
<223> OTHER INFORMATION: Primer

<400> SEQUENCE: 66
ccgtgacgcc actacaacag 20

<210> SEQ ID NO 67
<211> LENGTH: 20
<212> TYPE: DNA
<213> ORGANISM: Artificial Sequence
<220> FEATURE:
<223> OTHER INFORMATION: Primer

<400> SEQUENCE: 67
gcttaacggg tacggcgttt 20

<210> SEQ ID NO 68
<211> LENGTH: 20
<212> TYPE: DNA
<213> ORGANISM: Artificial Sequence
<220> FEATURE:
<223> OTHER INFORMATION: Primer -continued

```
<400> SEQUENCE: 68

gcggttaatc cagcgtatgc                                                20


<210> SEQ ID NO 69
<211> LENGTH: 19
<212> TYPE: DNA
<213> ORGANISM: Artificial Sequence
<220> FEATURE:
<223> OTHER INFORMATION: Primer

<400> SEQUENCE: 69

cagggccgta cgagaacgt                                                 19


<210> SEQ ID NO 70
<211> LENGTH: 20
<212> TYPE: DNA
<213> ORGANISM: Artificial Sequence
<220> FEATURE:
<223> OTHER INFORMATION: Primer

<400> SEQUENCE: 70

gcccacgaca gcagacaact                                                20
```